(12) United States Patent
Kelleher et al.

(10) Patent No.: US 12,070,416 B2
(45) Date of Patent: Aug. 27, 2024

(54) SYSTEMS AND METHODS FOR THE TREATMENT OF EYE CONDITIONS

(71) Applicant: Alcon Inc., Fribourg (CH)

(72) Inventors: Brian S. Kelleher, San Diego, CA (US); John Slate, Encinitas, CA (US); Michael Burk, San Marcos, CA (US); Mark Petersen, San Diego, CA (US); David Esbaugh, Valley Center, CA (US); Dan Vance, Valley Center, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/883,178

(22) Filed: Aug. 8, 2022

(65) Prior Publication Data

US 2023/0043137 A1 Feb. 9, 2023

Related U.S. Application Data

(63) Continuation of application No. 16/703,074, filed on Dec. 4, 2019, now abandoned.
(Continued)

(51) Int. Cl.
*A61F 9/007* (2006.01)
*A61F 7/00* (2006.01)
(Continued)

(52) U.S. Cl.
CPC ............ *A61F 9/00718* (2013.01); *A61F 7/00* (2013.01); *A61F 9/00709* (2013.01);
(Continued)

(58) Field of Classification Search
None
See application file for complete search history.

(56) References Cited

U.S. PATENT DOCUMENTS 5,792,049 A * 8/1998 Eppstein ............... G01J 5/02
356/326
8,328,420 B2 * 12/2012 Abreu ............... A61B 5/6898
374/170
(Continued)

FOREIGN PATENT DOCUMENTS

CN 205459330 U 8/2016
CN 107174393 A 9/2017
(Continued)

*Primary Examiner* — Carl H Layno
*Assistant Examiner* — Manolis Pahakis

(57) ABSTRACT

Systems, methods, and devices used to treat eyelids, meibomian glands, ducts, and surrounding tissue are described herein. In some embodiments, an eye treatment device is disclosed, which includes a scleral shield positionable proximate an inner surface of an eyelid, the scleral shield being made of, or coated with, an energy-absorbing material activated by a light energy, and an energy transducer positionable outside of the eyelid, the energy transducer configured to provide light energy at one or more wavelengths, including a first wavelength selected to heat the energy-absorbing material. Wherein, when the eyelid is positioned between the energy transducer and the scleral shield, the light energy from the energy transducer and the heated energy-absorbing material of the scleral shield conductively heats a target tissue region sufficiently to melt meibum within meibomian glands located within or adjacent to the target tissue region.

6 Claims, 54 Drawing Sheets

Related U.S. Application Data

(60) Provisional application No. 62/776,333, filed on Dec. 6, 2018.

(51) Int. Cl.
*A61F 9/008* (2006.01)
*A61F 9/009* (2006.01)
*A61N 5/06* (2006.01)

(52) U.S. Cl.
CPC ............ *A61F 9/0079* (2013.01); *A61F 9/009* (2013.01); *A61N 5/0613* (2013.01); *A61N 5/0625* (2013.01); *A61F 2007/0004* (2013.01); *A61F 2009/00844* (2013.01); *A61F 2009/00861* (2013.01); *A61N 2005/0643* (2013.01); *A61N 2005/0658* (2013.01)

(56) References Cited

U.S. PATENT DOCUMENTS

| | | | | |
|---|---|---|---|---|
| 10,092,449 | B2* | 10/2018 | Kelleher | A61F 9/009 |
| 10,456,298 | B2* | 10/2019 | Kelleher | A61N 5/0624 |
| 10,820,986 | B2* | 11/2020 | Abramson | A61B 5/6821 |
| 10,974,063 | B2* | 4/2021 | Kelleher | A61F 9/00772 |
| 11,166,708 | B2* | 11/2021 | Charles | A61B 90/30 |
| 2002/0049389 | A1* | 4/2002 | Abreu | G02C 7/04 |
| | | | | 600/318 |
| 2003/0109773 | A1* | 6/2003 | Samuels | A61B 5/0059 |
| | | | | 600/315 |
| 2008/0081999 | A1* | 4/2008 | Gravely | A61F 9/00772 |
| | | | | 600/473 |
| 2009/0161827 | A1* | 6/2009 | Gertner | A61N 5/1017 |
| | | | | 378/65 |
| 2009/0163898 | A1* | 6/2009 | Gertner | A61B 3/113 |
| | | | | 606/4 |
| 2009/0182312 | A1* | 7/2009 | Gertner | A61F 9/009 |
| | | | | 606/4 |
| 2015/0005750 | A1* | 1/2015 | Kelleher | A61F 9/0079 |
| | | | | 606/27 |
| 2015/0057701 | A1* | 2/2015 | Kelleher | A61H 23/0245 |
| | | | | 606/204.15 |
| 2018/0001108 | A1* | 1/2018 | Kelleher | A61N 5/0617 |

FOREIGN PATENT DOCUMENTS

| | | |
|---|---|---|
| JP | 2017533074 A | 11/2017 |
| RU | 181572 U1 | 7/2018 |
| WO | 2013114127 A1 | 8/2013 |
| WO | 2016070134 A1 | 5/2016 |
| WO | 2018039729 A1 | 3/2018 |

* cited by examiner

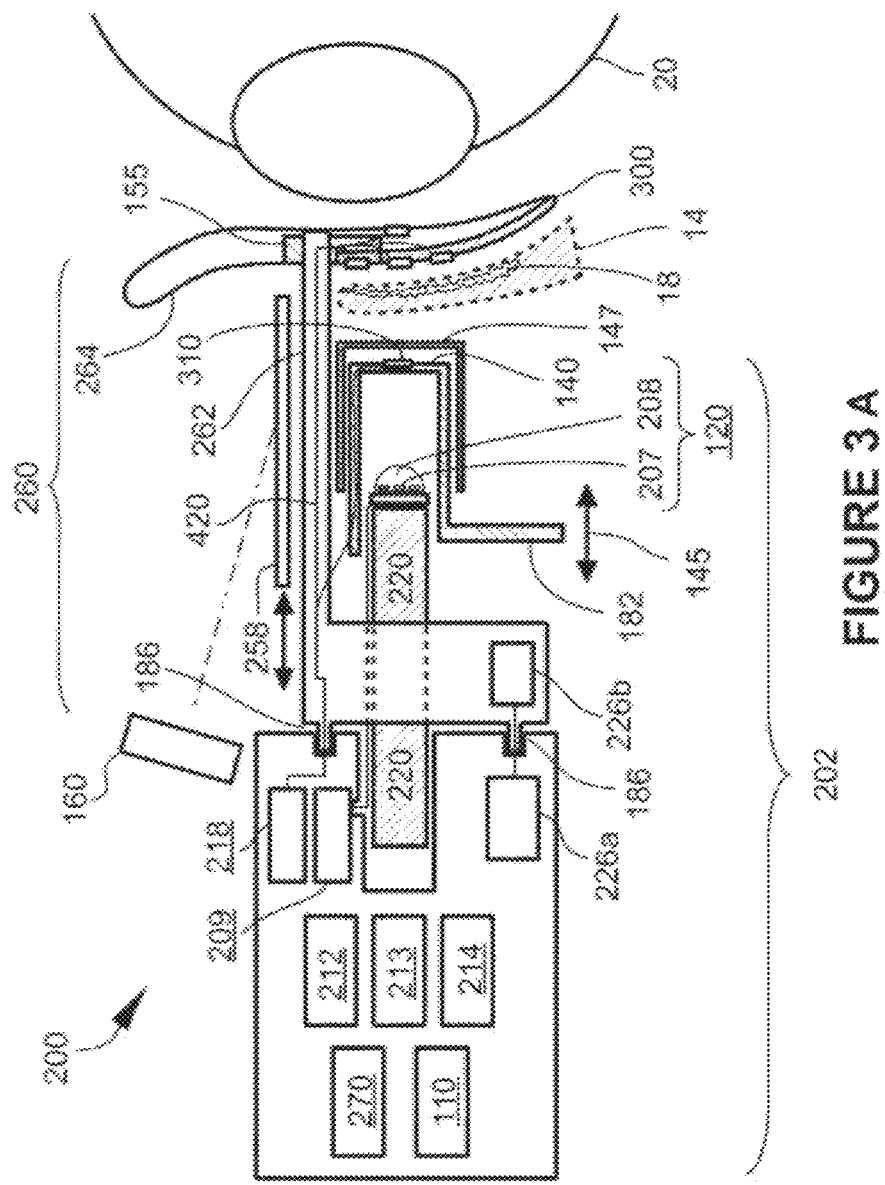

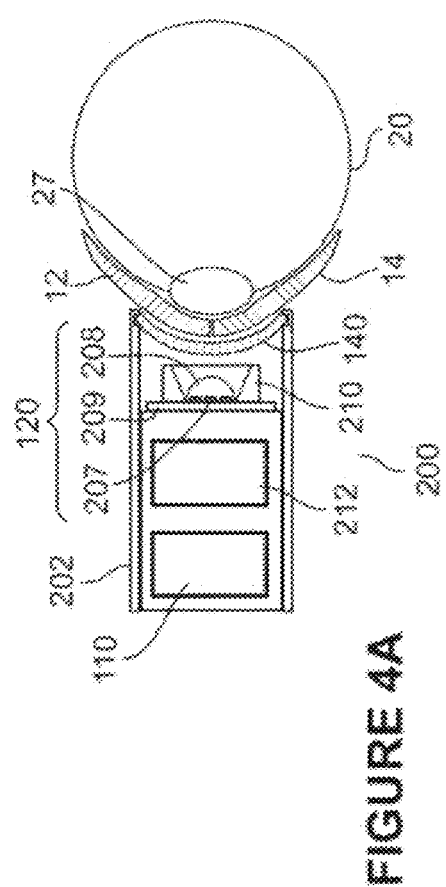
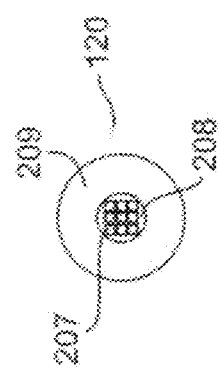
FIGURE 4A
FIGURE 4B

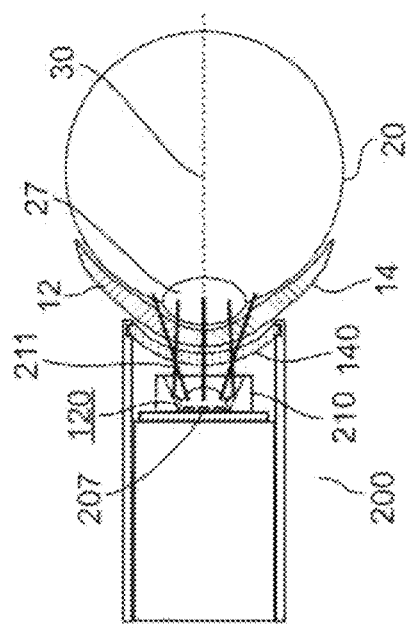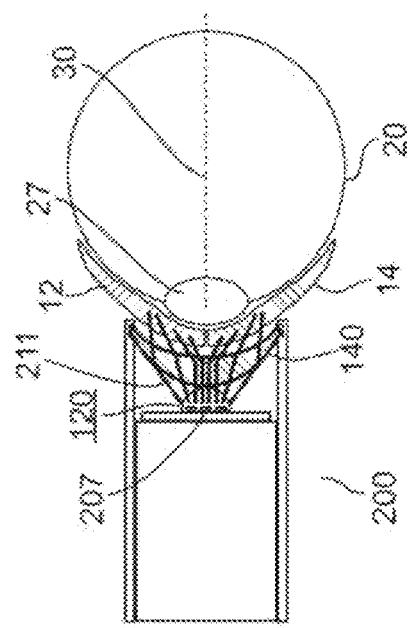
FIGURE 4C
FIGURE 4D

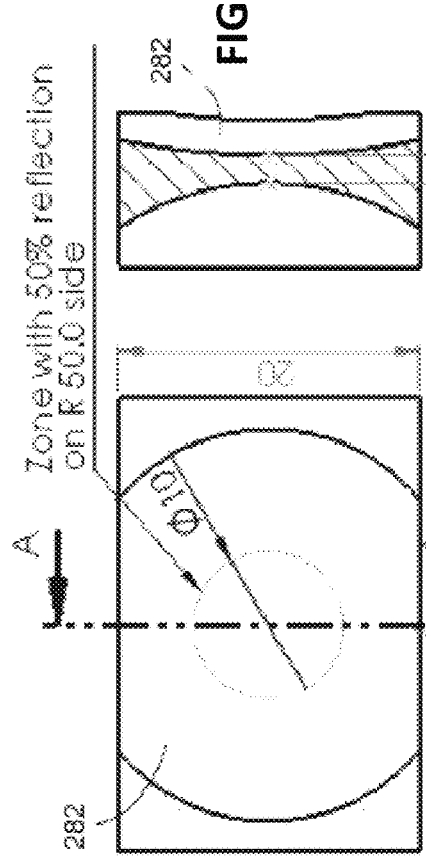
FIGURE 4I
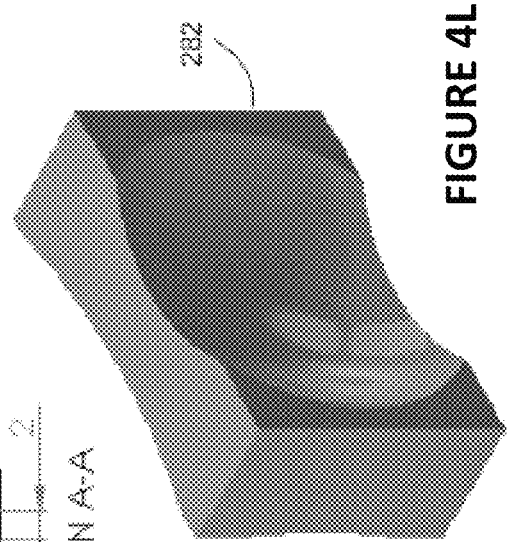
FIGURE 4J
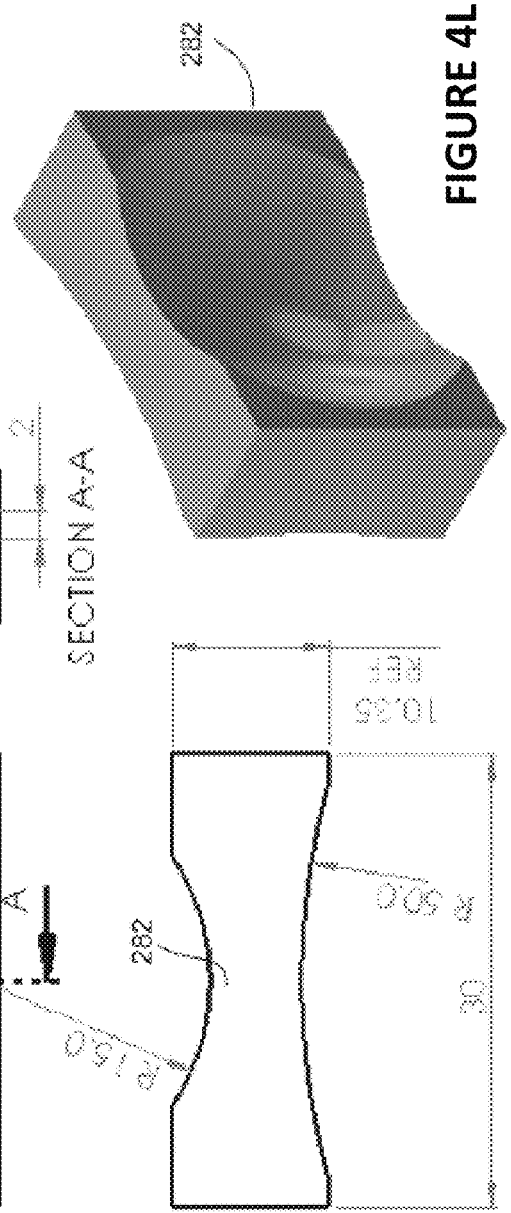
FIGURE 4K
FIGURE 4L

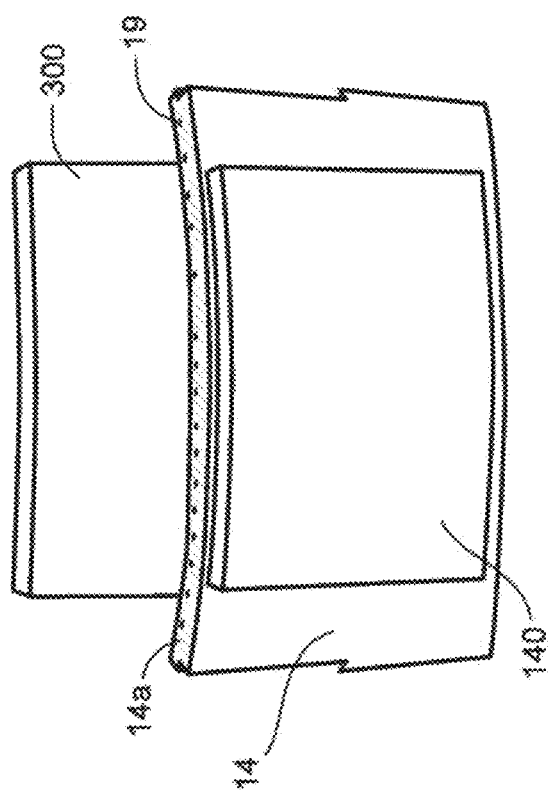

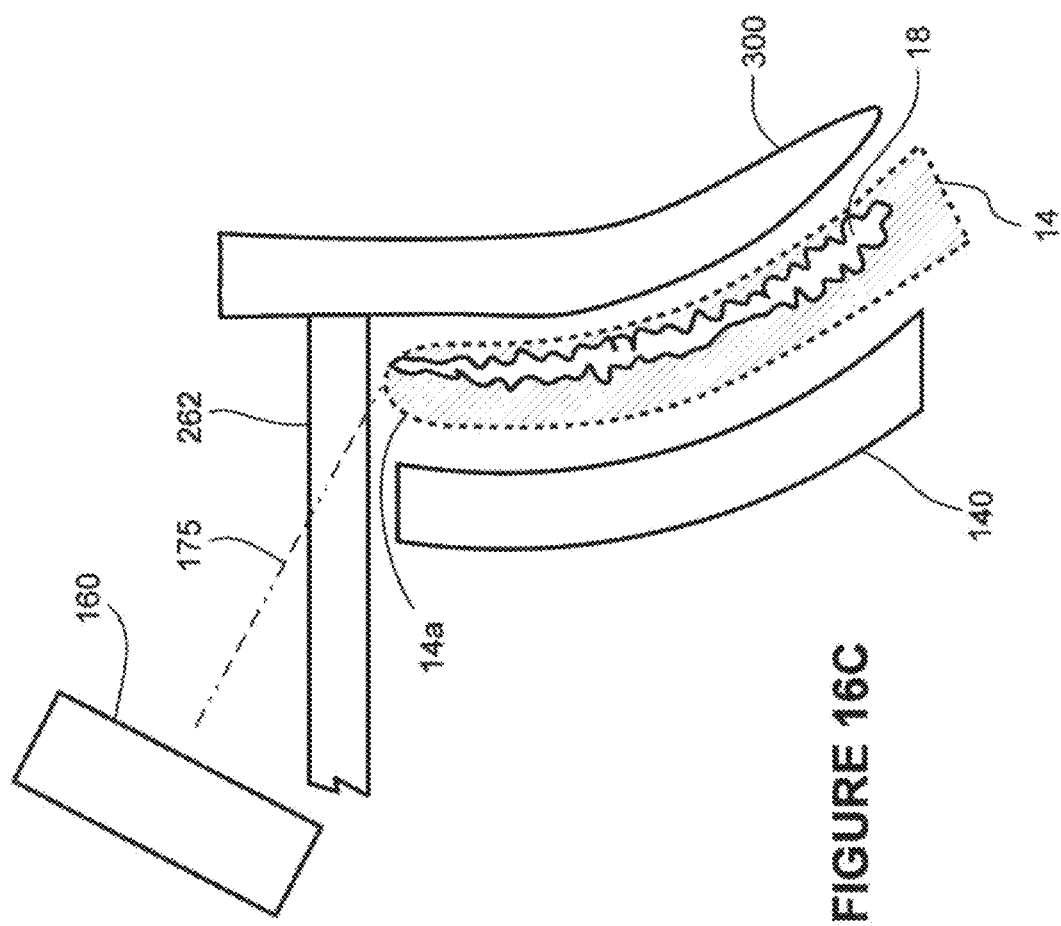

SYSTEMS AND METHODS FOR THE TREATMENT OF EYE CONDITIONS

CROSS-REFERENCES TO RELATED APPLICATIONS

This application is a continuation of U.S. application Ser. No. 16/703,074, filed Dec. 4, 2019, which claims the benefit of U.S. Provisional Application No. 62/776,333, filed Dec. 6, 2018, which is incorporated herein by reference. Priority of the aforementioned filing date is claimed.

BACKGROUND

The present disclosure relates to medical devices and methods of using the same. More particularly, the disclosure relates to systems, methods, and apparatus used to diagnose and treat conditions of the eye such as meibomian gland dysfunction and blepharitis, typically involving eyelids, meibomian glands, ducts, orifices, and surrounding tissue.

Meibomian gland dysfunction (MGD) is thought to be the most common cause of evaporative dry eye disease, with studies showing a prevalence ranging from 20% to 60% in the general population. MGD is associated with a failure of meibomian glands to produce an adequate quantity of normal secretions (called meibum). Meibum is a lipid-rich essential component of a healthy tear film. When sufficient meibum is not present in the tear film, the film readily evaporates, leading to evaporative dry eye disease. In some patients, the viscosity and melting point of the meibum may elevate, resulting in thickened meibum that does not flow easily out of the glands. Further, the channel or duct within the meibomian gland may become hyperkeratinized, leading to excessive cellular debris and contributing to the clogging of the gland over time. Once the glands become chronically clogged (inspissated), they may atrophy, and no longer be able to produce or secrete meibum.

Blepharitis is a common chronic inflammatory condition involving the eyelid and eyelid margin, and is often associated with MGD. Studies show a prevalence of blepharitis in the general population ranging from 12% to 47%, with higher prevalence amongst older individuals. In addition to certain causative factors relating to MGD, blepharitis may be caused in part by an abundance of certain bacteria in and around the eye and eyelid. By-products of the bacteria are thought to be irritating to the eye, leading to further inflammation and discomfort to the patient. In addition, several types of common mites may play a role in adding to the inflammation of the meibomian glands or sebaceous glands in and around the eyes. The inflammation caused by these factors can lead to further constriction of the meibomian gland ducts, limiting the flow of meibum from the glands and aggravating the condition.

Diagnosis of meibomian gland dysfunction can be done in many ways. Typical approaches include measurement of tear break-up time (TBUT), staining of various ocular surfaces, and examination of the meibomian glands and their secretions. One common technique used to examine the glands themselves is to evert the eyelid and to place a light source under the everted lid (on the outer surface of the lid) while examining the "transilluminated" image of the glands created by passing light through the lid. The image may be observed by an unaided eye, through a biomicroscope, or with a camera. Healthy glands appear as long, relatively straight forms, while dysfunctional glands may appear tortuous and swollen, and atrophied glands show a lack of continuity between the gland mass and the duct or orifice. In certain cases, infrared light is projected onto or through the everted lid, and an IR-sensitive camera is used to view the meibomian glands. The disadvantage of these transillumination techniques is that they require the lid to be everted, which is uncomfortable for most patients, and which can be difficult for the clinician to perform on some eyelids.

Another common technique for diagnosing MGD is to apply pressure to the eyelid while observing the meibomian gland ducts or orifices along the lid margin, usually with a magnifying means such as a biomicroscope. Healthy glands produce a clear oily secretion in response to the applied pressure. Glands that are partially dysfunctional produce less oil and/or cloudy oil. Glands that are more severely dysfunctional (inspissated) produce a paste-like secretion, which can only be squeezed out when more significant pressure is applied to the lid. Glands that are completely atrophied or that have had their orifices occluded do not produce any oil, even under high pressure.

MGD and blepharitis are chronic conditions with limited effective treatment. One of the most commonly recommended treatments is the application of a hot compress and massage (using the compress or fingertips) to the eyelid region. The intended goal of hot compress treatment is to heat up inspissated meibomian glands where thickened meibum resides, causing the meibum to soften and thereby more easily be expressed through the ducts. This process is thought to unclog the ducts and thereby allow the ducts to resume normal secretions and maintain a healthier tear film. Patients are generally instructed to apply a hot washcloth or other hot compress to the eyelid for five to ten minutes, multiple times daily. However, the efficacy of such an approach may be limited.

In-office treatment of MGD is often limited to squeezing the affected eyelids in order to express meibum from clogged or inspissated glands. Most clinicians use their fingertip or a cotton swab to apply pressure to the outer lid surface, but sometimes they also use a swab or a flat metal device (sometimes called a Mastrota paddle) on the inner lid while pushing against the outer lid in order to squeeze meibum out. All of these techniques are cumbersome for clinicians and painful for most patients.

Another in-office treatment uses intense pulsed light (IPL) around the eyes and eyelids. Such treatments are said to produce an improvement in dry eye symptoms over multiple sessions, but the mechanism is not understood and the equipment is expensive.

Still another in-office treatment is the TearScience Lipi-Flow(r) system, wherein heating elements are placed underneath the eyelids and an automated external controller maintains the heating elements at a target temperature while applying a predetermined pattern of compression against the outer lids by way of inflatable bladders. This system is expensive and does not allow the clinician to control the treatment such to visually monitor the eyelid margin and meibomian gland ducts and to vary the level of heating and compression during the procedure in a manner that optimizes the treatment outcome. Such clinician control over the treatment may be important and is not present in the Tear-Science system.

Patients may also use saline drops or artificial tears to reduce the discomfort associated with dry eye; however, this approach fails to treat the dysfunctional meibomian glands and underlying inflammation. Additionally or alternatively, antibiotics may be prescribed to reduce the bacterial load in and around the eyelid. Topical and oral antibiotics are available, including oral tetracycline derivatives, which reduce certain bacteria and provide a mild anti-inflammatory effect; however, the administration of antibiotics may cause side effects or adverse allergic reactions, and the approach is often insufficient to provide significant long-term relief of blepharitis and MGD. Corticosteroids may be prescribed to reduce the inflammation; however, prolonged use of such steroids increases the risk of detrimental cortical lens changes, intraocular pressure spikes, and infection due to immunosuppression.

A need therefore exists for improved methods and devices to diagnose and treat meibomian gland dysfunction and blepharitis.

SUMMARY

Embodiments described herein may meet one or more of the needs identified above and may overcome one or more of the shortcomings of current MGD and blepharitis treatment methods. Various implementations of systems, methods, and devices within the scope of the appended claims each have several aspects, no single one of which is solely responsible for the desirable attributes described herein. Without limiting the scope of the appended claims, some prominent features are described herein.

The present application relates generally to treatment systems, methods, and devices used to treat eyelids, meibomian glands, ducts, and surrounding tissue. Details of one or more implementations of the subject matter described in this specification are set forth in the accompanying drawings and the description below. Other features, embodiments, and advantages will become apparent from the description, the drawings, and the claims.

In an aspect, a device for treating a mammalian eye having an eyelid is provided, the device including: an energy transducer having a device that emits light energy at multiple wavelengths, including a first wavelength selected to pass through eyelid and a second wavelength selected to be absorbed by the eyelid for warming; a frontplate positionable proximate an outer surface of the eyelid, the frontplate being made of a clear material that passes the wavelengths of light emitted by the energy transducer, the frontplate further including sensors configured to provide information regarding a position of the eyelid relative to the frontplate; a backplate positionable proximate an inner surface of the eyelid, the backplate being made of or coated with an energy-reflecting material configured to receive the first wavelength of light energy transmitted through the eyelid and reflect it back to the eyelid, the backplate further including sensors configured to provide information regarding a position of the eyelid relative to the frontplate; and wherein when the eyelid is positioned between the frontplate and backplate and the light energy from the energy transducer heats a target tissue region sufficiently to melt meibum within meibomian glands located within or adjacent to the target tissue region.

In embodiments, the device further includes an actuator coupled to the frontplate and backplate configured to cause relative movement between the frontplate and backplate to squeeze the eyelid to express the meibomian glands. In embodiments, the actuator is further configured to control the amount of light energy emitted from the energy transducer at the second wavelength, thereby controlling the heating of the target tissue. In embodiments, the actuator is at least one of a lever, a button, a wheel, a slider, and a switch.

In embodiments, the energy transducer is further configured to provide light energy at a third wavelength selected to treat bacteria. In embodiments, the energy transducer includes at least one of an LED, laser, incandescent lamp, xenon lamp, halogen lamp, luminescent lamp, high-intensity discharge lamp, and gas discharge lamp.

In embodiments, the device further includes a visualization device for viewing the eyelid during treatment. In embodiments, the device further includes one or more components selected from the group consisting of: a display or dashboard configured to display the device status; a temperature measurement device configured to measure various temperatures of the eyelid, including inner and/or outer eyelid surface temperatures; a datalogger; a voice recorder; a battery configured to power the device components; battery charging means; a controller; printed circuit board; and communication circuitry between shield and energy transducer.

In another interrelated aspect, a method for treating an eye condition in a mammal is provided, the method including: positioning a shield proximate an inner surface of an eyelid, the shield being made of, or coated with, an energy-absorbing material, the shield further including sensors configured to provide information regarding a position of the eyelid relative to the shield; positioning an energy transducer outside of an eyelid of the mammal, the energy transducer configured to provide light energy at one or more wavelengths; positioning an energy transmission surface outside the eyelid, the energy transmission surface including sensors configured to provide information regarding a position of the eyelid relative to the energy transmission surface; causing relative movement between the energy transmission surface and the shield so as to modify a spaced relationship between the energy transmission surface and the shield; directing light energy from the energy transducer toward the shield at a first wavelength selected to heat the energy-absorbing material; and heating the energy-absorbing material with the light energy to heat a target tissue region sufficiently to melt meibum within meibomian glands located within or adjacent to the target tissue region.

In embodiments, the method further includes directing light energy from the energy transducer toward an outer surface of the eyelid at a second wavelength selected to heat a target tissue region within the eyelid. In embodiments, the method further includes directing light energy from the energy transducer toward the eye at a third wavelength selected to treat bacteria.

In embodiments, the method further includes compressing the eyelid between the energy transmission surface and the shield. In embodiments, the method further includes focusing the compression on a sty or a pimple to treat a hordeolum. In embodiments, the method further includes focusing the compression on an occluded gland to treat a chalazion.

In embodiments, a safety feature electrically coupled to the energy transducer prevents or interrupts the light energy from occurring if the shield and associated assembly are not properly attached to, and aligned with, the device.

In embodiments, the relative movement between the energy transmission surface and the shield includes movement of the energy transmission surface relative to the shield. In embodiments, the relative movement between the energy transmission surface and the shield includes a sliding movement of the energy transmission surface relative to the shield. In embodiments, causing relative movement between the energy transmission surface and the shield includes actuating an actuator coupled to the energy transmission surface. In embodiments, actuating an actuator includes pressing a button. In embodiments, causing relative movement between the energy transmission surface and the shield includes causing the energy transmission surface to slide relative to the shield.

In embodiments, the position of the eyelid relative to the positions of the shield and the energy transducing surface must be within a predetermined range for the energy transducer to emit light energy.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Throughout the drawings, similar symbols typically identify similar components, unless context dictates otherwise. Note that the relative dimensions of the following figures may not be drawn to scale.

FIG. 3A is a schematic block diagram of an embodiment of an eye diagnostic and treatment device.

FIG. 4A is a schematic side plan view of one embodiment of an eye treatment device.

FIG. 4B is a schematic front plan view of the energy transducer and waveguide modules included in the eye treatment device embodiment of FIG. 4A.

FIG. 4C is a schematic side plan view of the eye treatment device embodiment of FIG. 4A shown in use.

FIG. 4D is a schematic side plan view of another embodiment of an eye treatment device.

FIGS. 4I-L are front, cross-section, side and perspective views of the shaping lens element of FIG. 4E.

DETAILED DESCRIPTION

Figure 1B:
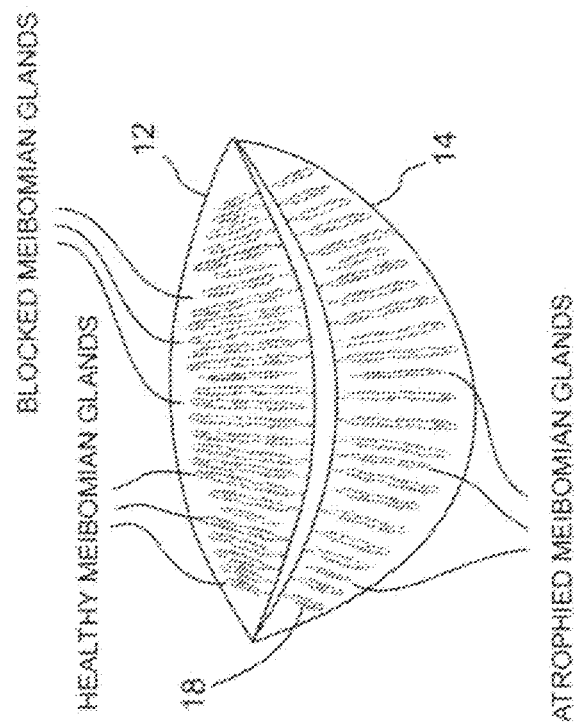
FIG. 1B is a view of the underside surfaces of the upper and lower eyelids showing meibomian glands with healthy, clogged and atrophied glands.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, and designed in a wide variety of different configurations, all of which are explicitly contemplated and form part of this disclosure.

The terminology used herein is for the purpose of describing particular embodiments only and is not intended to be limiting of the disclosure. It will be understood by those within the art that if a specific number of a claim element is intended, such intent will be explicitly recited in the claim, and in the absence of such recitation, no such intent is present. For example, as used herein, the singular forms "a", "an" and "the" are intended to include the plural forms as well, unless the context clearly indicates otherwise. As used herein, the term "and/or" includes any and all combinations of one or more of the associated listed items. It will be further understood that the terms "comprises," "comprising," "have," "having," "includes," and "including," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

To assist in the description of the devices and methods described herein, some relational and directional terms are used. "Connected" and "coupled," and variations thereof, as used herein include direct connections, such as being contiguously formed with, or glued, or otherwise attached directly to, on, within, etc. another element, as well as indirect connections where one or more elements are disposed between the connected elements. "Connected" and "coupled" may refer to a permanent or non-permanent (i.e., removable) connection.

"Secured" and variations thereof as used herein include methods by which an element is directly secured to another element, such as being glued, screwed, or otherwise fastened directly to, on, within, etc. another element, as well as indirect means of securing two elements together where one or more elements are disposed between the secured elements.

"Proximal" and "distal" are relational terms used herein to describe position from the perspective of a medical professional treating a patient. For example, as compared to "distal," the term "proximal" refers to a position that is located more closely to the medical professional, while the distal end is located more closely to the patient during treatment. For example, the distal ends of the devices disclosed herein oppose the proximal ends of the same devices, and the distal end of a device often includes, for example, the end configured for placement against the eyelid of a patient.

"Transducer" is a term used herein to describe an element which receives one form of energy and transforms it into another. For example, a light source may receive electrical energy and produce light energy. Likewise, an ultrasonic transducer may receive electrical energy and produce ultrasonic energy.

"Light" as used herein refers not only to energy in the visible light spectrum, but also to energy in the infrared and ultraviolet portions of the electromagnetic energy spectrum.

"Waveguide" as used herein refers to any means of influencing the propagation, distribution or trajectory of electromagnetic energy such as light, ultrasonic energy and radio frequency energy. As defined herein, an optical elements such as diffractors, refractors, diffusers and the like are included in this broad definition of a waveguide.

"Optical path length" is used herein to describe the length of the path (for example, within a tissue section) through which energy travels.

Embodiments disclosed herein relate to ophthalmic devices, systems, and methods. The devices, systems, and methods disclosed herein can be used to treat meibomian glands, ducts, orifices, and surrounding tissue and are particularly directed to the treatment of MGD, blepharitis and conditions having a physiological relationship with MGD and blepharitis, such as evaporative dry eye disease. FIG. 1A is a cross-sectional diagram of a mammalian eye system 10, which includes an eyeball 20 and surrounding eyelid anatomy. As recited within this disclosure and as identified in FIG. 1A, the "central ocular axis" 30 of the eye is the central axis running through the center of the cornea 22, iris 24, pupil 25, lens 26, and vitreous body 28 of the eyeball 20. Eye system 10 includes an upper eyelid 12, a lower eyelid 14, and eyelashes 16. Within the tissue of each eyelid 12, 14, there are meibomian glands 18 each having an orifice or duct 19. In healthy eye systems 10, the meibomian glands 18 secrete out of ducts 19 a substance called meibum, comprised primarily of lipids and proteins. The meibum forms part of the tear film that covers the surface of the eyeball 20.

Figure 1A:
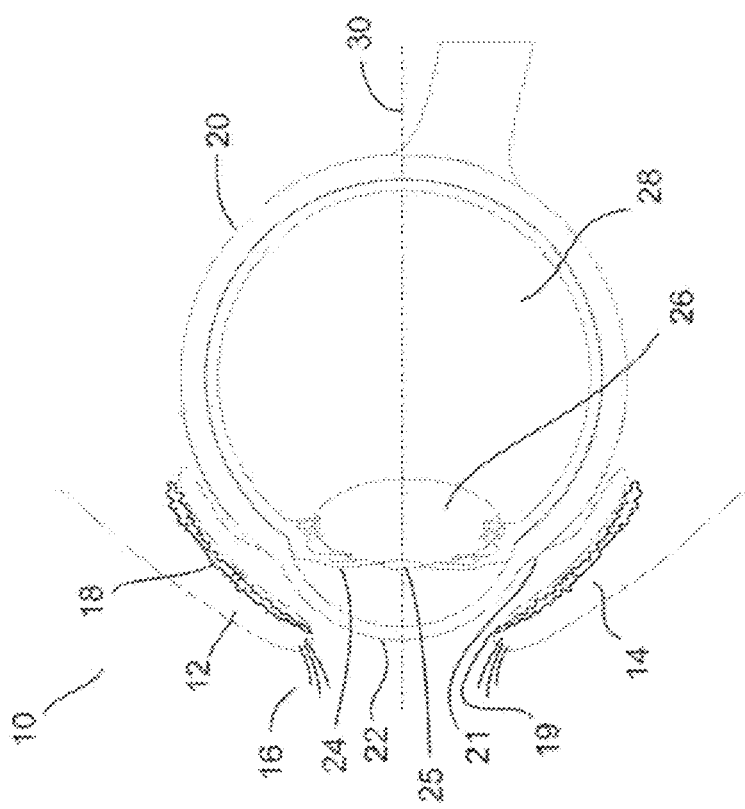
FIG. 1A is a cross-sectional diagram of a mammalian eye system 10.

FIG. 1B is a view of the inner eyelid showing meibomian glands with healthy, clogged and atrophied glands. Chronic blocking of the glands is associated with MGD and some forms of blepharitis, and may lead to capping of the ducts and/or atrophy of the glands. Inflammation associated with MGD or blepharitis may in turn cause a further constriction of gland ducts 19, leading to a reduction of meibomian gland secretion, and accordingly, a decreased amount of lipids in the tear film. Tear film with reduced lipid content may evaporate quickly and lead to evaporative dry eye. A reduced tear film may also be associated with increased levels of bacteria in and around the eye. Such bacteria can aggravate the inflammation by themselves or by certain by-products which are irritating to the eye. It is believed that by periodically clearing our chronically blocked glands, the glands can be spared from becoming permanently atrophied.

Another factor thought to contribute to blepharitis is the presence of *Demodex folliculorum* and *Demodex brevis* mites, which are commonly found on most humans, reported in higher quantities on individuals suffering from blepharitis. The mites may live in the hair follicles of the eyelashes and eyebrows and in meibomian glands and sebaceous glands. Their presence alone may lead to inflammation in certain individuals, but it is also thought that such mites may harbor certain bacteria which can be released into the eyelid region during their lifecycle, leading to further inflammation.

Figure 2B:
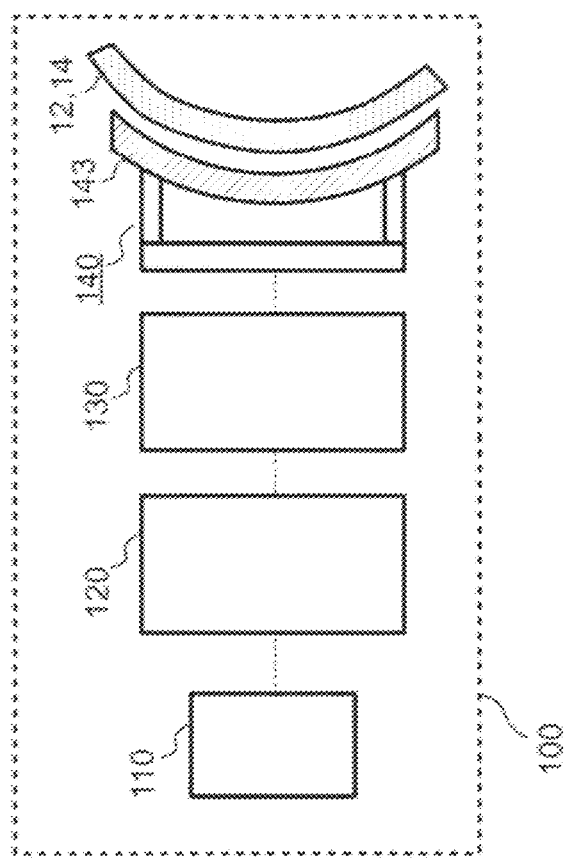
FIG. 2B is a schematic block diagram of another embodiment of an eye treatment device.
Figure 2A:
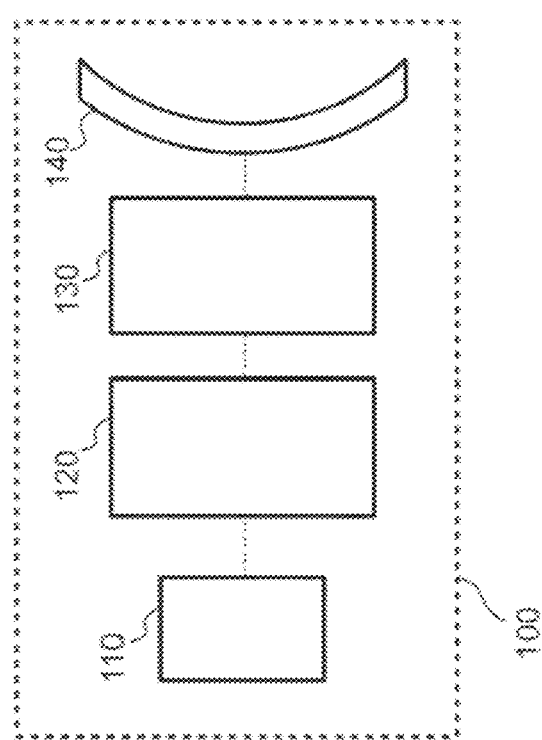
FIG. 2A is a schematic block diagram of one embodiment of an eye treatment device according to some embodiments.

FIG. 2A is a schematic block diagram of an eye treatment device 100 according to various embodiments. As shown in FIG. 2A, the depicted eye treatment device 100 includes a power source module 110, an energy transducer module 120, an energy waveguide module 130, and an energy transmission surface 140 (also referred to as a compression element). In some embodiments, the energy waveguide module 130 may be optional. In other embodiments, the energy transducer module 120 and energy waveguide module 130 may be combined in a single unit.

The power source module 110 of various embodiments provides energy to the energy transducer module 120. The power source module 110 may include any structure configured for delivering power to one or more other components of the eye treatment device 100. In some embodiments, the power source module 110 includes a disposable battery, a rechargeable battery, a solar cell, a power transforming module such as a power supply or power converter, or a power transfer mechanism such as a cord, outlet, or plug configured to receive alternating current or direct current from an external source.

The energy transducer module 120 may include one or more energy transducers configured to emit one or more forms or type of energy. For example, as described in more detail below, in some embodiments, the energy transducers emit photonic, acoustic, radio frequency, electrical, magnetic, electromagnetic, vibrational, infrared or ultrasonic energy. In some embodiments, the energy transducer module 120 generates multiple types of energy simultaneously or in a predetermined order.

The energy waveguide module 130 includes one or more structures configured to control or focus the direction of energy emission from the energy transducers. For example, the energy waveguide module 130 may include one or more reflectors, refractors, diffractors, or diffusers (described in more detail below) configured to focus photonic energy toward a desired region, or other structures for configuring and directing the energy emission, such as ultrasonic horns or fiber optics.

The eye treatment device 100 of FIG. 2A may further advantageously include an energy transmission surface 140 configured to further direct energy generated by the energy transducer module 120 toward a desired region. For example, the energy transmission surface 140 may include one or more lenses configured to focus energy generated by the energy transducer module 120.

In some embodiments, the energy waveguide module 130 and the energy transmission surface 140 may also prevent or limit the transmission of energy generated by the energy transducer module 120 to particular regions of the eye. The energy transmission surface 140 may include regions that are substantially opaque or non-transmissive to the energy produced by the energy transducer module 120 and regions that are translucent or transmissive to the energy produced by the energy transducer module 120. The modules of the eye treatment device 100 are described in further detail below in relation to other embodiments of the disclosure and may include other components.

FIG. 2B is a schematic block diagram of an eye treatment device 100 according to various embodiments. FIG. 2B is similar to FIG. 2A and includes a power source module 110, an energy transducer module 120, an optional energy waveguide module 130, and an energy transmission surface 140. The energy transmission surface 140 may be substantially solid, or it may include elements that are spaced apart from other parts of the energy transmission surface 140 or eye treatment device 100. For example, energy transmission surface 140 may include an extension element that is positioned at a certain distance from the solid portion of energy transmission surface 140. For example, in FIG. 2B, extension element 143 is depicted as a mesh-like structure spaced apart from the main portion of energy transmission surface 140 (if any). Extension element 143 may comprise a surface that is at least partially transparent to the desired energy generated by energy transducer module 120, while keeping a gap between the main portion of the energy transmission surface 140 (if any) or the energy waveguide (if any) or the energy transducer module and the eyelid surface 12, 14. The gap created by extension element 143 may be beneficial in providing a path for forced-air cooling of the eyelid, for example. Additionally, pressing extension element 143 against the eyelid surface may reduce the optical path length for heating the eyelid 12, 14 and/or targeted components within the eyelid. Reducing the optical path length may be advantageous for heating tissue due to improvements in radiant throughput, decreased scattering, refractive index matching, and increased fluence. Extension element 143 may be made of a low thermal mass material, like a thin-wire or plastic mesh or perforated thin metal or plastic surface, and may be structured to conform to the shape of the eyelid while applying pressure to the surface of the eyelid. In one embodiment, extension element 143 may be structured so that when it is pressed against both the upper and lower eyelids, it can distribute the applied pressure either uniformly or non-uniformly across the combined upper and lower outer eyelid surfaces. For example, in one embodiment, extension element 143 may apply less pressure to the central ocular axis 30 and more pressure elsewhere, which may be desirable in cases where pressure applied repeatedly to the eyelids over the central ocular axis may be thought to increase the possibility of developing a complication such as keratoconus. In other embodiment, extension element 143 may be actively heated or cooled.

Figure 2C:
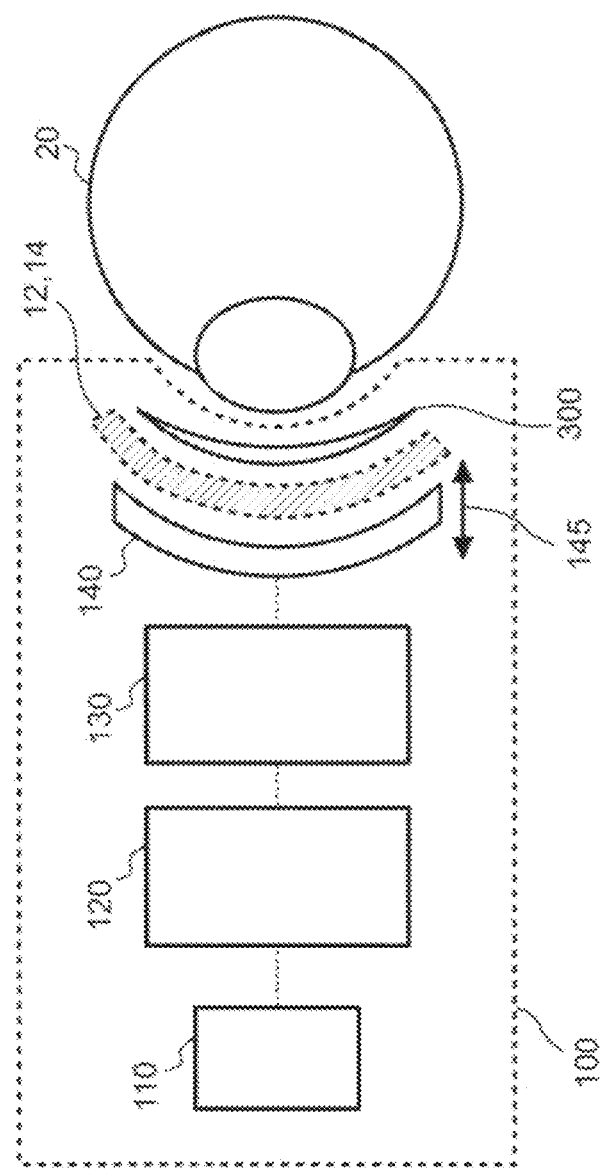
FIG. 2C is a schematic block diagram of another embodiment of an eye treatment device having a scleral shield.

FIG. 2C is a schematic block diagram of another embodiment of an eye treatment device 100 having a power source module 110, an energy transducer module 120, an optional energy waveguide module 130, an energy transmission surface 140 and scleral shield 300 (also referred to as a backplate). In this embodiment, one or more eyelids 12, 14 are positioned between the energy transmission surface 140 and scleral shield 300.

The energy transducer module 120 may include one or more energy transducers configured to emit one or more forms or type of energy. For example, as described in more detail below, in some embodiments, the energy transducers emit photonic, acoustic, radio frequency, electrical, magnetic, electromagnetic, vibrational, infrared or ultrasonic energy. In some embodiments, the energy transducer module 120 generates multiple types of energy simultaneously or in a predetermined order. An optional energy waveguide module may be included to control or focus the direction of energy emission from the energy transducers, as described above.

The eye treatment device 100 of FIG. 2C may further advantageously include an energy transmission surface 140 configured to further direct energy generated by the energy transducer module 120 toward a desired region. The energy transmission surface 140 may include one or more lenses configured to focus energy generated by the energy transducer module 120. The energy transmission surface 140 (and/or extension element 143 shown in FIG. 2B) may be movable along a movement path 145 in order to adjust certain energy transmission properties (such as focus) and/or to contact the surface of the eyelid 12, 14 and/or to apply pressure to the eyelid 12, 14. By applying pressure to the eyelid 12, 14 while keeping scleral shield 300 in a fixed spatial relationship relative to other parts of eye treatment device 100, the eyelid 12, 14 may be compressed, thereby reducing the optical path length for heating the eyelid 12, 14 and/or targeted components within the eyelid. Reducing the optical path length is advantageous for heating tissue due to improvements in radiant throughput, decreased scattering, refractive index matching, and increased fluence. The eyelid may be compressed by the backplate 300 compressing or pushing the eyelid against the compression element. Or the eyelid may be compressed by the compression element compressing or pushing the eyelid against the backplate 300.

In some embodiments, the energy transducer module 120 may generate multiple types of energy simultaneously, such as photonic, acoustic, radio frequency, electrical, magnetic, electromagnetic, vibrational, infrared or ultrasonic energy. For example, a first energy may heat the outer surface of the eyelid while a second energy may penetrate more deeply into the eyelid tissue and/or interact with the scleral shield in modes described in further detail below.

Figure 2D:
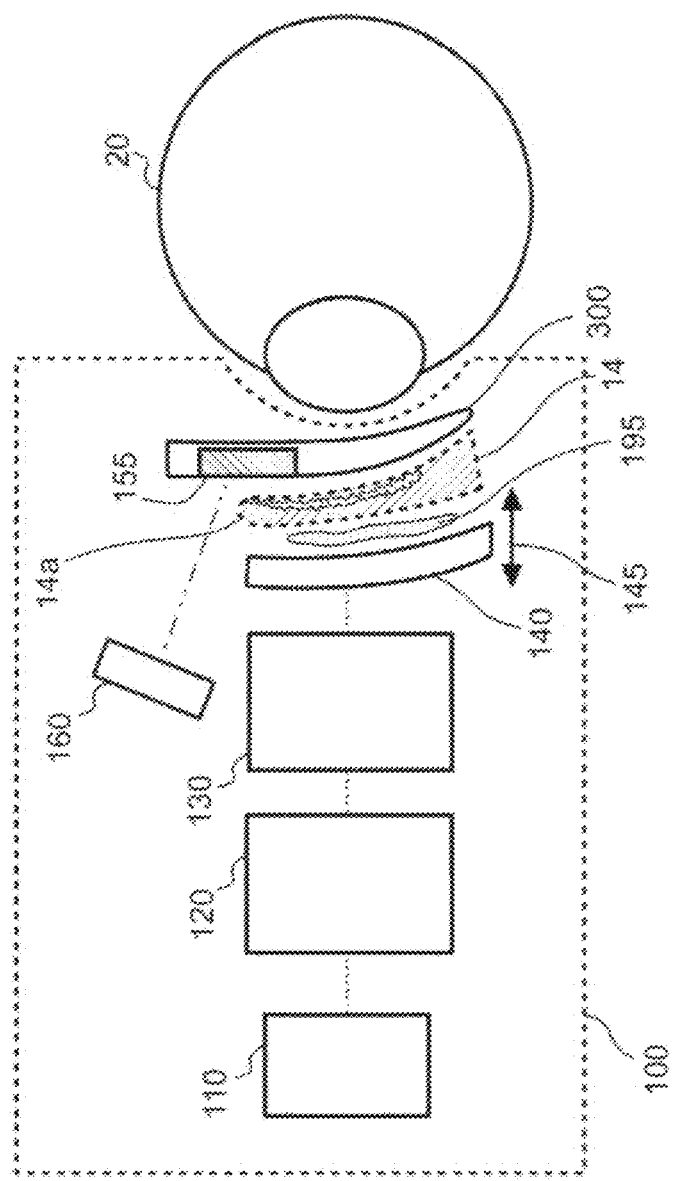
FIG. 2D is a schematic block diagram of another embodiment of an ophthalmic device having a scleral shield with imaging elements.
Figure 2E:
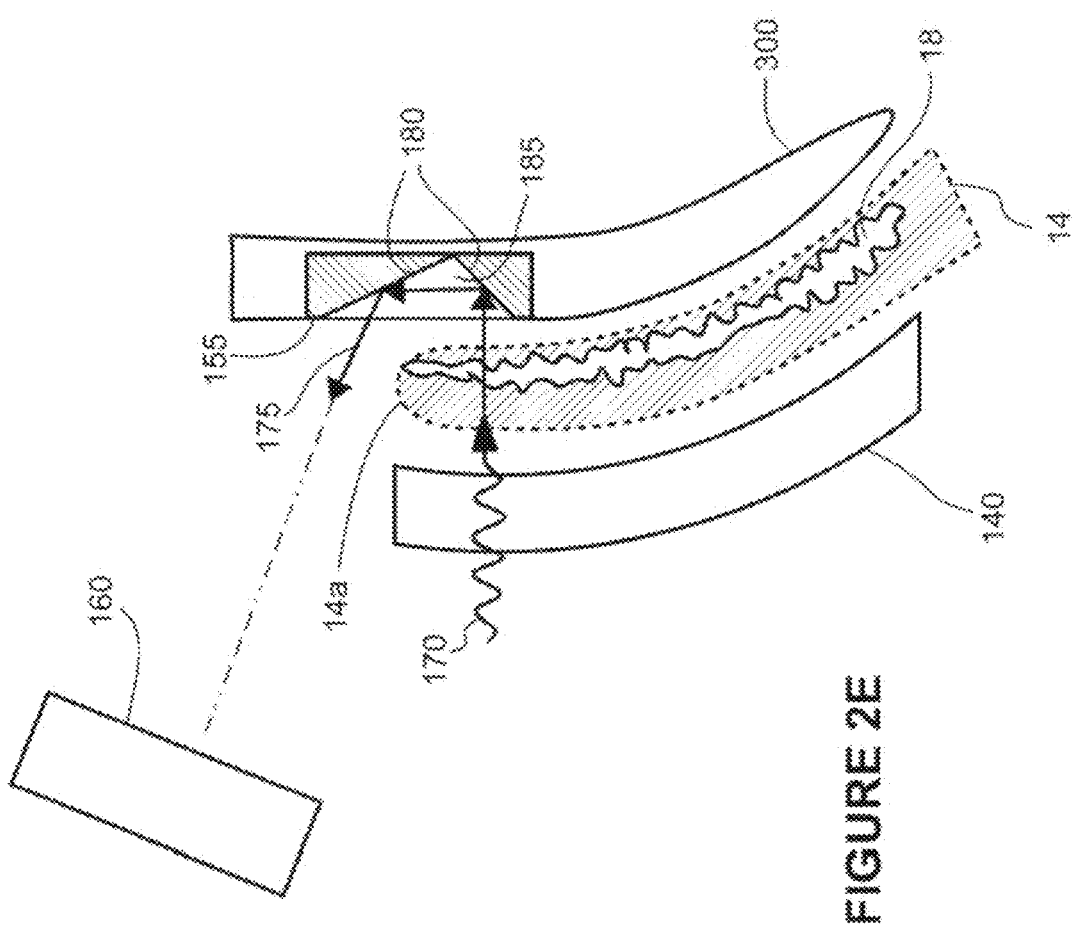
FIG. 2E is a close-up cross-sectional view of a portion of the embodiment of FIG. 2D.
Figure 2F:
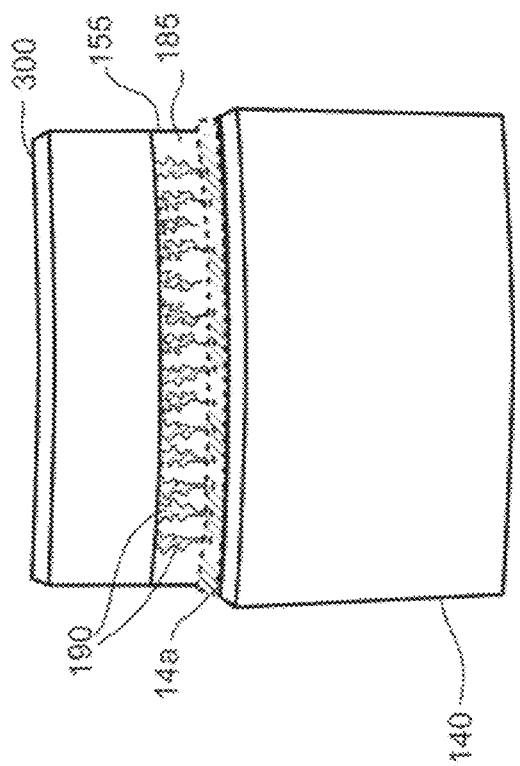
FIG. 2F is a front view of the embodiment shown in FIG. 2E.

FIG. 2D is a schematic block diagram of another embodiment of an eye treatment device 100 having a power source module 110, an energy transducer module 120, an optional energy waveguide module 130, an energy transmission surface 140 and scleral shield 300, similar to FIG. 2C. In some embodiments, the scleral shield 300 may further include an image translator 155 integrated into scleral shield 300. FIG. 2E shows a close-up cross-sectional view of image translator 155 embedded in scleral shield 300, with eyelid 14 positioned adjacent to image translator 155. In the embodiment shown, image translator 155 is reflective. Illumination energy 170, which may be visible or infrared light, for example, is passed through eyelid 14 and therefore through meibomian glands 18, and then along optical path 175 through energy transmissive material 185 as it reflects off of reflective surfaces 180, eventually exiting image translator 155 above the eyelid margin 14a. It will be appreciated that the resulting image appearing out of image translator 155 will be a shadow image, or transilluminated image, of that portion of eyelid 14 that is adjacent to image translator 155 and which is illuminated by illumination energy 170. In this manner, image translator 155 allows viewing of a transilluminated image 190 of the inner side of the eyelid 14 under direct visualization or with the aid of a magnifying element or camera, shown collectively as a visualization device or visualization means 160, without having to evert the eyelid. FIG. 2F is a front view of the same embodiment shown in FIG. 2E, showing transilluminated images 190 of the meibomian glands.

Image translator 155 may comprise a set of mirrored surfaces or a prism having reflective surfaces. Alternatively, image translator may comprise a light-bending element such as a light pipe, a fiberoptic bundle, an image sensor, or some combination thereof. It will be appreciated that various desirable optical properties may be incorporated into image translator 155, such as image projection, angulation or magnification. Such properties may be achieved, for example, by curving the reflective surfaces 180, by shaping the surfaces of transmissive material 185 and/or by varying the index of refraction, by varying the density and distribution of fiber elements in a bundle, or by some combination thereof. In embodiments where image translator 155 includes an image sensor, such sensor may be of a CCD-type, CMOS type, luminescent concentrator (such as has been fabricated at Johannes Kepler University, Linz, Austria), or any type of sensor that can capture the transillumination data and translate it into either visual, optical or electrical information.

In some embodiments, visualization of eyelid margin 14a during diagnosis and treatment of eyelid 14 provides a significant benefit. For example, as described above, positioning eyelid 14 between the energy transmission surface 140 and scleral shield 300 having image translator 155 allows visualization of the transilluminated image of the eyelid and meibomian glands. As shown in FIG. 1B, the morphology of healthy, clogged and atrophied glands is distinct enough to allow diagnosis of the status of each gland by viewing a transilluminated image of the glands. Referring back to FIG. 2D, gland status may be also be evaluated without transillumination by observing eyelid margin 14a while moving energy transmission surface 140 along movement path 145 to press against eyelid 14. As the eyelid 14 is compressed, eyelid margin 14a is observed and gland status is assessed by the quality and quantity of secretions from ducts 19, as discussed previously.

If treatment is desired after diagnosis, eye treatment device 100 may be repositioned along eyelid 14 so that the preponderance of diseased glands are positioned between energy transmission surface 140 and scleral shield 300. Once ideally positioned, energy transmission surface 140 may be moved along movement path 145 to contact the surface of the eyelid 12, 14 and/or to continue to move toward the scleral shield 300 and apply pressure to the eyelid 12, 14.

Referring again to FIG. 2D, an optional coupling medium 195 may be positioned between the eyelid 12, 14 and the energy transmission surface 140. Coupling medium 195 may be a fluid, gel, cream or the like, and may contain an agent such as glycerol, which can increase the efficiency of light transmission into the eyelid and target tissue by reducing light scattering and increasing light transmittance by reducing the refractive mismatch between the eyelid 12, 14 and the energy transmission surface 140. It may also assist in reducing scattering by hydrating portions of the eyelid skin surface such as the stratum corneum.

Figure 2G:
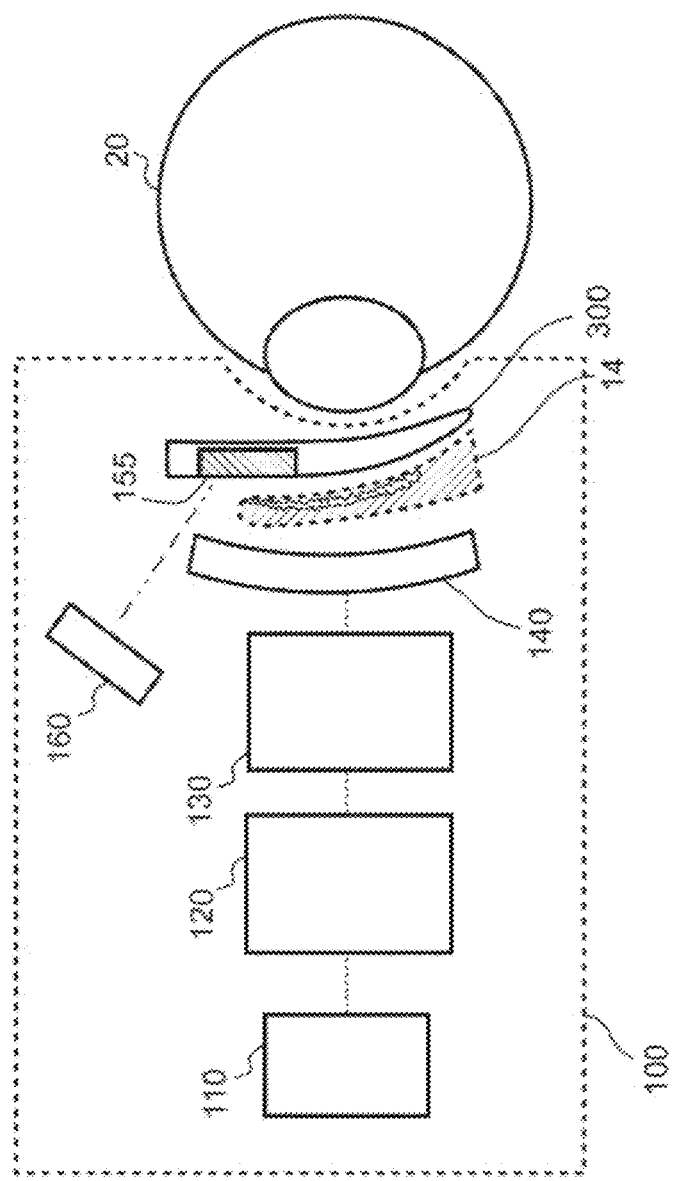
FIG. 2G is a schematic block diagram of another embodiment of an ophthalmic device similar to FIG. 2D.

FIG. 2G is a schematic block diagram of another embodiment of an eye treatment device 100 having a power source module 110, an energy transducer module 120, an optional energy waveguide module 130, an energy transmission surface 140, and image translator 155 integrated into scleral shield 300. The image translator 155 allows at least a portion of the energy from the energy transmission surface 140 to be redirected toward the inner side of the eyelid 14. For example, the eyelid 14 may be positioned between the energy transmission surface 140 and scleral shield 300 which includes the image translator 155. The energy transmission surface 140 directs energy toward at least one of the outer side of the eyelid and the image translator 155. The image translator 155 is able to redirect energy from the energy transmission surface 140 toward the inner side of the eyelid. The benefit of directing energy via the image translator 155 to the inner surface of the eyelid is that it can provide an efficient mode of delivering energy, and thus heat, to at least the portion of the inner surface adjacent to the eyelid margin. By combining this mode of heating (via image translator 155) with the mode of heating whereby the energy is directed through the eyelid, overall heating efficiency of the inner eyelid surface may be optimized, and preferential additional heating of the inner surface adjacent to the lid margin may be achieved, since that is the zone where significant clogging and blockage may occur. An additional temperature sensor may be positioned near the inner eyelid surface tissue adjacent to the lid margin, where the preferential additional heating may occur (described and depicted below with reference to FIG. 3A).

Figure 2H:
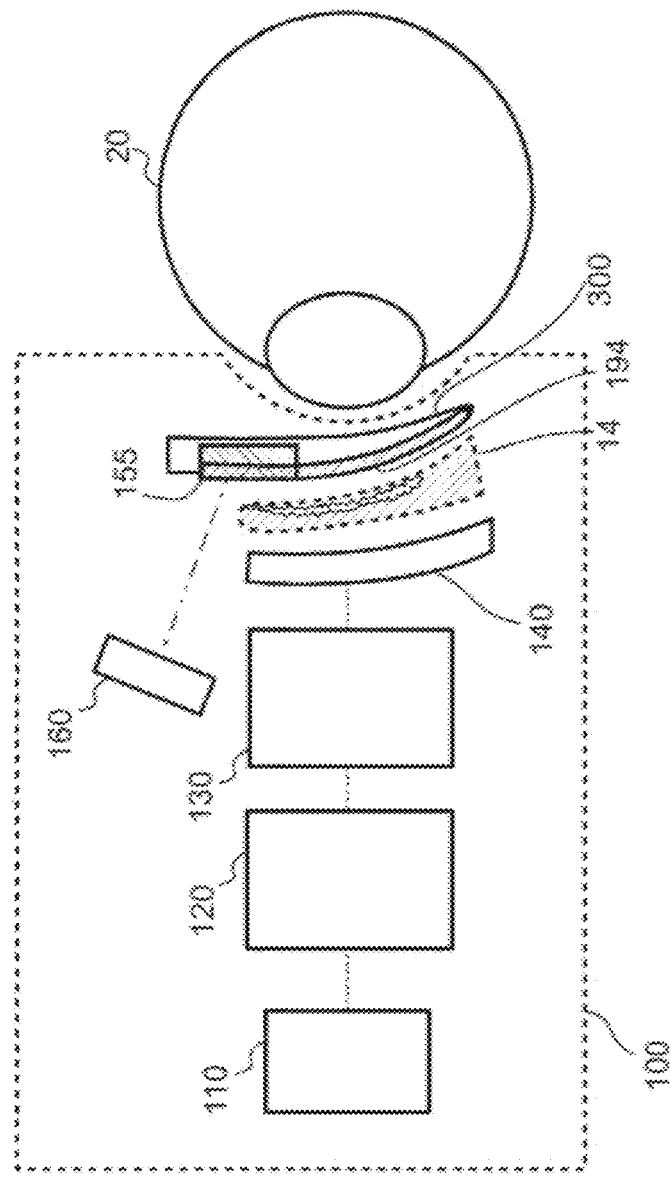
FIG. 2H is a schematic block diagram of another embodiment of an ophthalmic device similar to FIG. 2C.

FIG. 2H is a schematic block diagram of another embodiment of an eye treatment device 100 having a power source module 110, an energy transducer module 120, an optional energy waveguide module 130, an energy transmission surface 140 and scleral shield 300, similar to FIG. 2C. In some embodiments, the scleral shield 300 may further include an energy conversion coating 194 capable of being activated by certain types of energy passing through the eyelid. In one embodiment, the energy conversion coating 194 is able to convert the direction of energy back toward the inner side of the eyelid, using the same form of energy that originally passed through the eyelid. In another embodiment, the energy conversion coating 194 may alter the type of energy and direct or emit the altered energy in a preferred direction. In one embodiment, the coating is a phosphorescent. By way of example, the energy transmitted through the eyelid may be visible or infrared light of a wavelength that passes readily through the tissue with little absorption, and once that energy reaches energy conversion coating 194, the phosphorescent material emits light energy of a different wavelength that is more readily absorbed by the tissue adjacent to the coating, which, in the preferred embodiment, would be the inner surface of the eyelid, containing the meibomian glands. In another embodiment, a certain form of energy absorbed by the coating triggers an exothermic chemical reaction that may heat the inner surface of the eyelid. Some embodiments of FIGS. 2A-2H may also include one or more of the following: a scleral shield with support arms, a reflective imager integrated into scleral shield, a display of various temperatures, a consumable portion, a connector and circuitry for communication between device and the consumable in order to identify the consumable and prevent reuse, a data logger, a voice recorder and a camera with recording and/or transmission capability activated by certain types of energy passing through the eyelid. In one embodiment, the energy conversion coating 194 is able to convert the direction of energy back toward the inner side of the eyelid, using the same form of energy that originally passed through the eyelid. In another embodiment, the energy conversion coating 194 may alter the type of energy and direct or emit the altered energy in a preferred direction. In one embodiment, the coating is a phosphorescent material that is activated by the energy transmitting through the eyelid from the energy transmission surface 140. By way of example, the energy transmitted through the eyelid may be visible or infrared light of a wavelength that passes readily through the tissue with little absorption, and once that energy reaches energy conversion coating 194, the phosphorescent material emits light energy of a different wavelength that is more readily absorbed by the tissue adjacent to the coating, which, in the preferred embodiment, would be the inner surface of the eyelid, containing the meibomian glands. In another embodiment, a certain form of energy absorbed by the coating triggers an exothermic chemical reaction that may heat the inner surface of the eyelid.

FIG. 3A is a schematic side plan view of one embodiment of an eye treatment device 200. The eye treatment device 200 shown in FIG. 3A is shown to be positioned relative to an eyeball 20 for treatment of the eyelid 14 for MGD, blepharitis and other medical conditions. In some embodiments, the eye treatment device 200 is configured to heat the inner and/or outer surfaces of the eyelid while compressing the eyelid. As the heat from the eye treatment device 200 is transmitted to the eye system 10, particularly to the treatment tissue such as the meibomian glands, the heat can soften the meibum and thereby allow the meibum to be more readily expressed during massage or eye exercises. The eye treatment device 200 can include configurations of the modules depicted in FIGS. 2A-2H, along with additional components useful in operation of the eye treatment device 200.

Figure 3B:
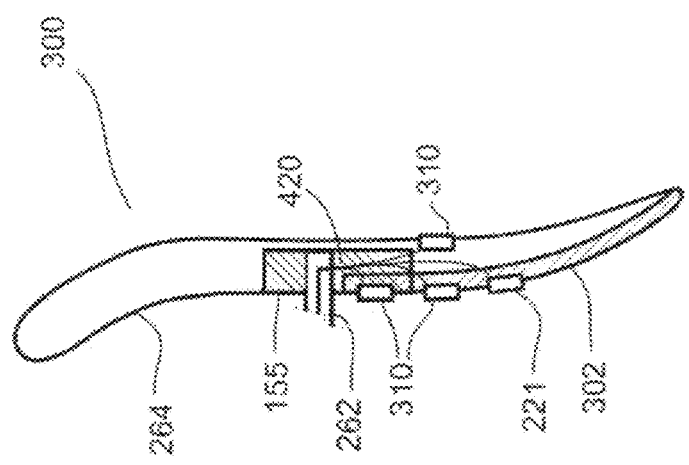
FIG. 3B is an enlarged view of one embodiment of a scleral shield shown in FIG. 3A.
Figure 7A:
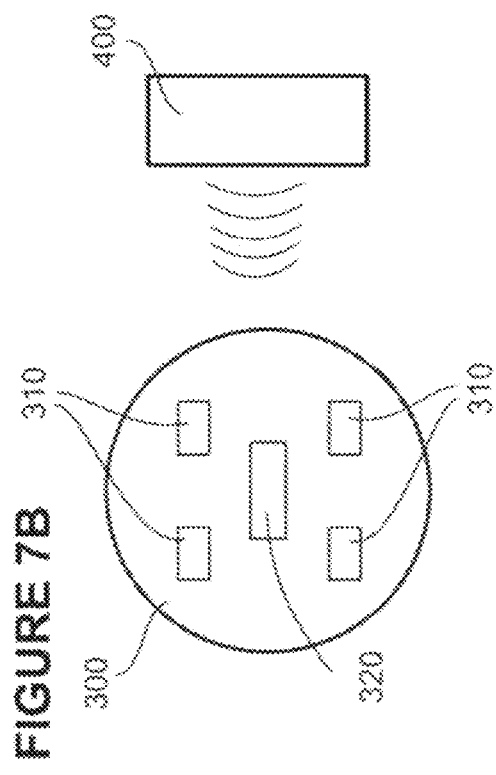
FIGS. 7A-7H are schematic front plan and side views of various embodiments of a scleral shield.
Figure 7B:
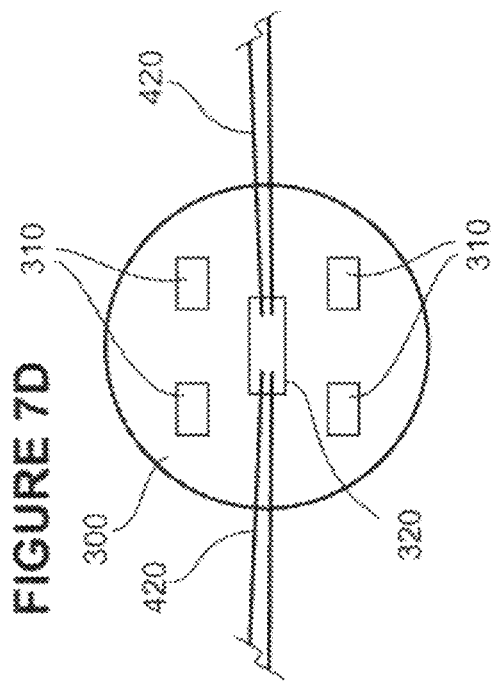
Figure 7C:
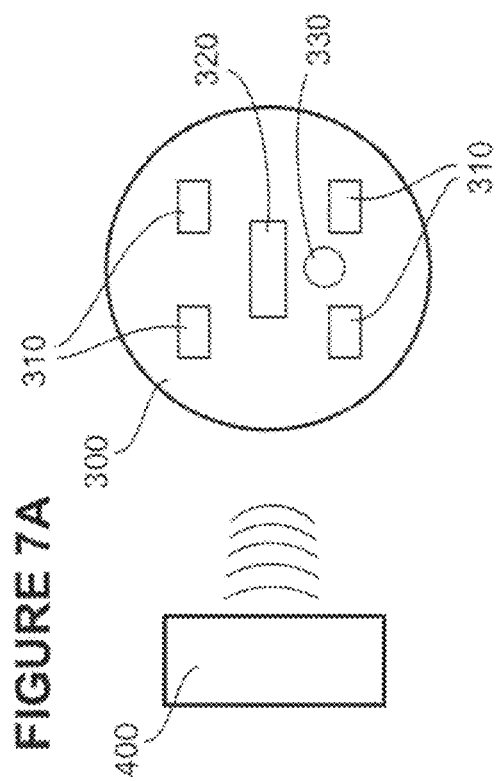
Figure 7D:
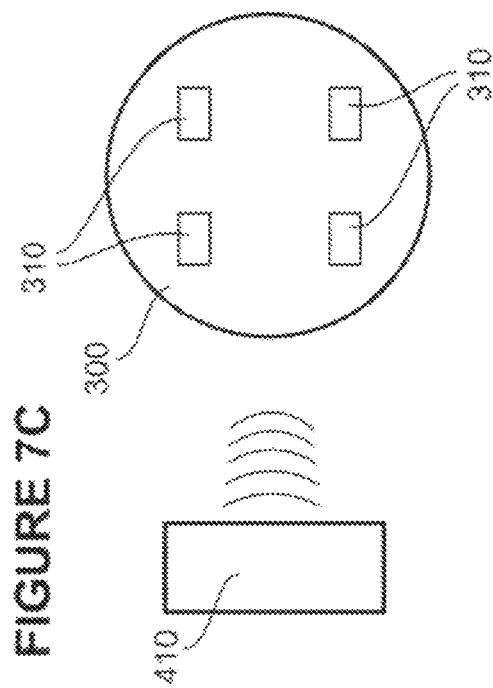

The eye treatment device 200 can include a housing 202 coupled with a removable or consumable portion 260, which may be coupled to housing 202 u engagement means 186, which can be pins, alignment guides, slide locks, and the like. Housing 202 may include a power source module 110, an optional controller 212, an energy transducer module 120, and an energy transmission surface 140 in a slidable relationship along movement path 145 with energy transducer module 120. Alternatively, energy transmission surface 140 may linked with, or part of, energy transducer module 120, and optionally thermal management structure 220, and together they may be in a slidable relationship with respect to housing 202 or other parts of eye treatment device 200. Movement of energy transmission surface 140 and linked parts may be done using actuator 182, for example. The energy transducer module 120 of some embodiments, such as is shown in FIG. 3A, may include an LED device formed of one or more of an LED emitter 207, an LED lens 208, a thermal management structure 220, and an energy transducer module driver 209. The housing 202 may further include visualization means 160 for enhanced monitoring of the eyelid margin during diagnosis and treatment, a display or dashboard 218 showing various temperatures of the eyelid, such as inner and/or outer surface temperatures, a datalogger 214, voice recorder 213, and circuitry 226 a for communication between device and consumable circuitry 226 b in order to identify the type of consumable, ensure that the consumable is in proper alignment and/or prevent reuse of the consumable. The consumable portion 260 may include a scleral shield 300 that can be positioned between the eyelid 12, 14 and eyeball 20 to cover sensitive anatomy of the eye system 10 (such shown in FIG. 1). For example, the scleral shield may be positioned over the sclera 21 and cornea 22 and may also provide protection to other internal anatomy of the eye such as the iris 24, pupil 25, lens 26, and other light sensitive anatomy of the eye system 10. Use of the scleral shield 300 can increase safety and reduce the potential of harmful light emissions from the energy transducer module 120 reaching and damaging sensitive eye anatomy. The scleral shield 300 may be formed from an energy absorbing material and/or may have an energy absorbing front face 302. In either case, energy transmitted through the eyelid which is absorbed by the scleral shield 300 or energy absorbing front face 302 may heat the shield or front surface, respectively, and thereby provide warmth to the inner surface of the eyelid. The back surface and edges of scleral shield 300 are preferably made from a material and process that ensures a smooth, burr-free finish that cannot cause injury, or reduces the likelihood of injury, to the cornea or other sensitive eye structures. In one preferred embodiment, the back surface and edges are covered with an expanded Teflon(r) (ePTFE) material. The scleral shield 300 may also incorporate one or more temperature sensors 310 in order to monitor temperature, as well as force or pressure sensors 221 to monitor the amount of force or pressure applied on the eyelid. Electrical conductors such as wires 420 may connect sensors 310 and 221 to circuitry in the housing 202. FIG. 3B shows one embodiment of a scleral shield 300 further including an image translator 155 which, as described previously, enables viewing of the inner side of the eyelid 14 and the meibomian glands behind the eyelid. In some embodiments, the scleral shield 300 may further include a data transmission means and/or an embedded power source, both discussed in more detail below as data transmission means 320 and embedded power source 330, such as in FIG. 7A. By way of further clarification, scleral shield 300 may be coupled to housing 202 in various manners such as with one or more wires 420, such wires having insulation with sufficient mechanical strength to serve as support arms 262. In addition, some embodiments may have circuitry 226 a and 226 b for communication between the device and the consumable.

In some embodiments, a lens 208 may be used, such as an LED lens over the LED emitter 207. In some embodiments, the LED lens 208 may be a specially shaped lens used to control the direction and intensity of the LED emitter 207 to the desired treatment tissue and/or the scleral shield 300. In some embodiments, the energy transmission surface 140 may act as a lens or used in combination with a lens, to focus and direct the energy from the energy transducer module 120 or LED emitter 207 to the desired treatment areas.

Each of these components, either alone, or in combination with other components any of the embodiments described herein.

The eye treatment device 200 can include a power source module 110 for providing power to the various components of the eye treatment device 200 and may be electrically coupled to some or all of the components. In some embodiments, the power source module 110 is battery operated using either regular or rechargeable batteries that may be coupled to a recharging system. In other embodiments, the power source module 110 may be coupled to an external power source, such as an electrical outlet or external battery supply. In some embodiments, the power source module 110 may be electrically coupled with the controller 212 to receive instructions from the controller 212 to provide electrical energy to the various components of the eye treatment device 200.

In certain embodiments having a controller 212, the controller 212 can receive input instructions from a user (for example, through a user interface device 270, such as a button, switch, touch screen, voice commands, from another module or device, such as a smartphone) to emit light from the LED emitter 207. Upon receipt of the user input instructions, the controller 212 can instruct the power source module 110 to deliver energy to or from the energy transducer module driver 209 which enables LED emitter 207 to convert the electrical energy from the power source module 110 into another form of electromagnetic energy (such as light). In this manner, the energy transducer module driver 209 and the LED emitter 207 can act as a transducer of the electrical energy received from the power source module 110.

The energy transducer module driver 209 can comprise any LED-powering and controlling circuitry, whether configured as an actual printed circuit board, an integrated circuit, or discrete components. In some embodiments, it serves the function of an LED driver, providing a controlled current, voltage or power level through the LED emitter 207 within the LED specifications to provide a desired illumination intensity therefrom. Optionally, the LED printed circuit board can include a pulse-width modulation function, PID circuit, or similar scheme in order to modulate the effective intensity of the emissions over time to achieve a desired heating of a target region of the eyelid.

The LED emitter 207 is a part of one type of energy transducer module 120 that can be configured to emit light of the appropriate wavelength necessary for the desired treatment. The treatments may include one or more of the following: diagnosing the eyelids 12, 14 by the illuminating the inner and/or outer surfaces, eyelid margins, and/or the meibomian glands behind the eyelids; heating the target tissue region of the eye system 10 (e.g., the meibomian gland behind the eyelids 12, 14); and antibacterial treatment to kill bacteria in the eye system 10. Note that the descriptions of the various devices herein (including the eye treatment device 200) are exemplary, and not limiting. Thus, for example, while this detailed description mentions particular elements and circuitry having particular functions, this does not limit the disclosure to those particular embodiments. For example, while LEDs are mentioned, other light sources, such as incandescent, xenon, halogen, high-intensity discharge, cold cathode tube, fluorescent, laser and other light sources or energy sources can be used. Similarly, while a controller 212 and energy transducer module driver 209 are mentioned, it will be understood that the controller could be integrated with driver circuitry for the light source or circuitry for a solid-state or other power supply, or other configurations could be used to provide the desired result. Further, some or all of the functions described as being handled by, or controlled by, controller 212, may be implemented using discrete logic or analog circuitry, or a combination thereof. Moreover, although the various embodiments such as eye treatment device 200 are illustrated schematically, they can be produced in a variety of handheld or stationary configurations with optional gripping surfaces, manipulation and control structures, and the like. Furthermore, the devices described herein can be designed for use in a plurality of settings, including in-home use and use within an eye care professional's office, a health clinic, or other healthcare facility.

In some embodiments, the energy transducer module 120 can instead be, for example, a broad-spectrum lamp, such as an incandescent, xenon, or halogen lamp. Such broad-spectrum lamps can be used in conjunction with one or more color filters to remove specific wavelengths not necessary for the treatment of the eye condition, or to remove specific wavelengths that may be harmful to the treatment tissue in the target region (e.g., meibomian glands 18) of the eye system 10 during application of energy from the energy transducer module 120 to the treatment tissue.

In some embodiments, the energy emitted from the power source module 110 can be converted into visible light and can be emitted by the LED emitter 207. For some embodiments, it is desirable to use light with a wavelength selected to: a) penetrate the eyelid to the depth of the meibomian gland (e.g., typically about 1-2 mm in certain individuals) or other adjacent target tissue in the eyelid, and be absorbed there, b) minimize the amount of light that penetrates beyond the eyelid tissue, and c) minimize the amount of heating that occurs at the surface of the eyelid. For example, in some embodiments, the LED emitter 207 can emit light having a wavelength in the range of about 400-700 nm. In some embodiments, the LED emitter 207 can emit light that is substantially a single color selected for optimal treatment of the meibomian glands 18 in the eye system 10. In some embodiments, the LED emitter 207 can emit light in a range of wavelengths, the wavelength being selectable based on the treatment requirements of the patient, or based on the intended purpose of the particular step in a multi-step treatment regimen.

In some embodiments, an illumination source emitting wavelengths in the range of 500-600 nm is chosen. In selecting wavelengths in the range of 500-600 nm, a plurality of considerations may be taken into account. For example, this range may be selected to achieve the highest absorption of light rays in tissue. Light energy incident on mammalian skin is reflected, transmitted, or absorbed. Reflection is a function of skin properties, wavelength, and angle of incidence. Light rays that reach the skin surface orthogonal to the plane of the surface are reflected less than those that reach the skin at an oblique angle. Transmission of light through the skin is a function of internal scattering, wavelength, and absorption. Internal scattering is a function of the chemical and physical properties of the skin and underlying tissues. Eyelid thickness, density of keratinocytes, collagen, and fat may play a role. Absorption is primarily a function of the concentration and distribution of certain molecules called chromophores which tend to selectively absorb certain wavelengths of light. In human skin, the primary chromophores that absorb light in the visible spectrum are oxyhemoglobin, deoxyhemoglobin, various melanins, and to some extent, water. Water does not significantly absorb wavelengths of light until the deep red and infrared part of the spectrum. Melanins tend to have a fairly high degree of absorption of the visible spectrum, tapering off gradually as wavelength increases. Two absorption peaks for oxyhemoglobin are seen at around 532 nm and 577 nm. Deoxyhemoglobin peaks around 550 nm.

In various embodiments, engineering constraints also affect wavelength selection. The wavelength selected is one that can be emitted by a device, which can be readily produced in a practical configuration, with a wattage and physical package appropriate for a device that delivers light energy to the eyelid. In the case of very high power LEDs, there are presently limited choices, although future improvements are likely. For example, LED Engin Inc. (San Jose, Calif.) produces green LEDs in a 10 W version, such as LZ4-00G108, having a nominal center/peak wavelength of around 523 nm. Limited quantities are also available with peak wavelengths of about 527 and 532 nm.

Various embodiments emit wavelengths within the 500-700 nm portion of the visible spectrum in order to produce the desired tissue heating effect without excessive transmission through the eyelid (and subsequent unwanted heating of structures beyond the eyelid), and without excessive surface heating. Furthermore, emitting wavelengths within this portion of the visible light spectrum avoids the undesired portion of the electromagnetic spectrum for embodiments that do not incorporate a scleral shield, including ultraviolet, infrared, and blue.

In some embodiments, longer wavelengths of light are used penetrate deeper into the tissue. For example, 'red' and near-infrared (NIR) at wavelengths between 700-1000 nm pass more readily through the eyelid, penetrating more deeply than the wavelength ranges described above. There is an "optical window" of human tissue around 800-900 nm, where energy passes most efficiently through tissue and eyelids due to the fact that chromophore absorption is at its lowest level. For the application of light therapy to the eyelids without the use of a scleral shield, the use of NIR would likely not be used due to excessive light energy passing through the eyelid directly to the eye, possibly affecting sensitive tissues of the eye. When using the scleral shield to protect the eye, however, NIR may be used advantageously to pass through the eyelid. For example, NIR at 850 nm may pass through the eyelid and be absorbed by the scleral shield, which, in turn, can warm adjacent tissue on the inner surface of the eyelid. For completeness of discussion, it should be noted that certain wavelengths of short-wavelength and mid-wavelength infrared (sometimes referred to as IR-B and IR-C) have higher levels of absorption by water than the highest combined absorption of the other chromophores discussed above. In particular, a wavelength of 3,000 nm has been shown to have such higher absorption. As such, there may be embodiments that use this wavelength or others within the band safely, with or without a scleral shield. Note that there are also other "optical windows" (in addition to the window mentioned at 800-900 nm) at these higher wavelengths, which may be advantageous to utilize in some embodiments.

In some embodiments, an illumination source emitting blue or violet light in the range of 400-450 nm may be used to reduce and/or eliminate bacteria in the eye system 10. It is known that exposure to visible light, more specifically, blue or violet light wavelengths, causes inactivation of certain bacterial species. Common bacteria include *S. aureus, S. epidermidis, B. oleronius,* and *P. acnes*. In selecting wavelengths in the range of 400-450 nm, a plurality of considerations may be taken into account. For example, it is important that the emitting source (LED) does not emit a significant amount of energy below about 400 nm, which is in the UVA spectrum and can be associated with skin cancer.

In another embodiment, one or more wavelengths of light may be chosen which are preferentially absorbed by the exoskeletons, internal structures or eggs of the *Demodex* mites, in order to kill, inactivate or interrupt reproductive processes.

In some embodiments, an illumination source may be used to characterize the tear film thickness and stability. For example, the energy transducer module could have a cobalt blue source, and the visualization means 160 (viewing lens, for example) could have a yellow Wrattan filter, and the patient could be given fluorescein eye drops, whereby the clinician could measure the tear break-up time by viewing the surface of the eye through the Wrattan filter. Alternatively, various wavelengths of photonic energy could be shined onto or across the surface of the eye, with or without indicator eye drops, and either through direct visual observation or image capture and processing, the stability and/or thickness of the tear film and/or lipid layer may be determined.

In another embodiment utilizing LEDs as an illumination source, the LED emitter 207 can include one or more multi-spectral LEDs or multiple LEDs to emit light of differing or the same wavelength from each LED. In some embodiments, each LED of the LED emitter 207 is configured to emit light of a different wavelength. The LED emitter 207 can emit the light from each differently colored LED either consecutively or simultaneously. For example, in some embodiments, the LED emitter 207 can include a red, green, blue (RGB) LED system, or other multi-spectral LED system, to emit light of various wavelengths in the visible light spectrum and IR spectrum. In some embodiments, the LEDs of the LED emitter 207 can be configured to operate simultaneously to emit white light. Alternatively, in some embodiments, the user can select the wavelength of light to be emitted from the multi-spectral LEDs. Further, an LED with using a special phosphorescent coating may be fabricated in order to produce the most efficient output spectrum relative to input power.

In some embodiments, the LED emitter 207 can include a high-intensity LED array. The high-intensity LED array, as part of the LED emitter 207, can, in some embodiments, operate at an input power rating of about 0.5-75 W, but preferably in a range of 1-10 W. To help keep the temperature of energy transducer module 120 within functional limits, thermal management structure 220 (such as a heat sink other substantial thermal mass) may be thermally linked to LED emitter 207. In a specific embodiment, the high-intensity LED array may emit light having a wavelength of between about 500-600 nm.

The energy transducer module 120 can, in some embodiments, provide electromagnetic energy to the treatment tissue in the form of infrared energy, such as in the NIR band described above. For example, the LED emitter 207 can be a commercially available LED such as LZ4-00R408, which emits 850 nm NIR and is manufactured by LED Engin, Inc. (San Jose). Additionally, the energy transducer module 120 can be another source of infrared energy instead of an LED light source, such as, for example, an incandescent, xenon, halogen, cold incandescent, or halogen broad spectrum lamp configured to emit infrared energy to the treatment tissue site.

The eye treatment device 200 may include a reflector (such as reflector 210 in other embodiments below), which may act as a waveguide to direct the electromagnetic energy (e.g., light) emitted from the energy transducer module 120. The reflector can be configured to direct electromagnetic energy evenly from the point source, such as, for example, the LED emitter 207, through the energy transmission surface 140, to the target treatment site of the patient.

The energy transducer module 120 can include an LED lens 208 that can be used in conjunction with the LED emitter 207 or other electromagnetic energy source to direct the energy to the eyelid at a desired angle or in a desired pattern, at a desired intensity.

Shown in FIG. 3A is an energy transmission surface 140 forming part of the eye treatment device 200. The energy transmission surface 140 has a slidable relationship along movement path 145 relative to the energy transducer module 120. The energy transmission surface 140 can be positioned in the housing 202 at a location distal to the energy transducer module 120, and positioned in between the energy transducer module 120 and the tissue treatment site of the eye system 10. Positioned in this manner, the energy transmission surface 140 can pass, or receive and transmit, the electromagnetic energy transmitted from the energy transducer module 120. In some embodiments, the energy transmission surface can be a concave shape (relative to the eye treatment device 200), such that the energy transmission surface 140 corresponds to the shape of the eyelids 12, 14 when closed. The energy transmission surface 140 may be shaped such that any electromagnetic energy emanating from the energy transducer module 120 must pass through the energy transmission surface 140.

In some embodiments, the energy transmission surface 140 is positioned adjacent to the eyelids 12, 14, and does not physically contact the eyelids 12, 14, but instead transfers heat to the treatment tissue radiantly. The energy transmission surface 140 can be substantially transparent to the desired electromagnetic energy transmitted by the energy transducer module 120 to allow for the transmission of energy from the energy transducer module 120 without significantly hindering the desired energy type or wavelength from reaching the treatment tissue. In some embodiments, the energy transmission surface 140 can be made of an optical plastic, sapphire, glass, calcium fluoride, or fiberglass. It can have an easy to clean outside surface and can be scratch resistant. Optionally, a temperature sensor 310 may be positioned on, in or adjacent to energy transmission surface 140 to provide temperature feedback for the energy transmission surface 140 and/or the outer surface of the eyelid.

In some embodiments, the energy transmission surface 140 can be configured to operate in conjunction with the energy transducer module 120 to filter unwanted wavelengths from reaching the treatment tissue or other portions of the eye system 10. For example, in some embodiments, the illumination source may transmit electromagnetic energy in both the IR and visible light spectra. The energy transmission surface 140 can be used to allow passage of, for example, the energy from the visible light spectrum, but filter out the energy from the IR spectrum. Likewise, if it is desired that only energy from one color reaches the treatment tissue, the energy transmission surface 140 can be used as a bandpass filter or be used with a filter to restrict passage of energy of wavelengths other than the color desired.

In some embodiments, the energy transmission surface 140 can be configured to come in physical contact with the eyelids 12, 14. As discussed above, in some embodiments the energy transmission surface 140 may be in a slidable relationship along movement path 145 with the energy transducer module 120. This allows the energy transducer module 120 to be in a fixed relationship with the eyelid while the energy transmission surface 140 may be moved forward into contact with the eyelids 12, 14. Alternative approaches to reducing the space between the outer surface of the eyelids 12, 14 and the energy transmission surface 140 are possible. For example, the energy transducer module 120 and energy transmission surface 140 may move together toward the eyelids, with the scleral shield 300 remaining in a relatively fixed position, or the scleral shield 300 may move relative to the other parts of the device. In any case, movement is preferably done manually by the clinician in order to allow the clinician some measure of tactile feedback. In certain embodiments, the eye treatment device 200 may include an actuator 182 such as a lever, button, wheel, slider or switch to move the energy transmission surface 140.

In some embodiments, at least a portion of energy transmission surface 140 may be configured as a single-use cover element or outer eyelid pad 147, as shown in FIG. 3A. Preferably, such outer eyelid pad 147 is incorporated into the consumable portion 260 of the device, wherein the outer eyelid pad 147 is automatically aligned and loaded onto energy transmission surface 140 as the consumable portion is attached to the housing 202.

In some embodiments, the energy transmission surface 140 may be heated to conductively transfer heat to the treatment tissue. In other embodiments, most of the tissue heating occurs as a result of radiant heating from the energy transducer module 120 to the tissue and/or the scleral shield 300, wherein substantially all of the desired electromagnetic energy passes through energy transmission surface 140, with little or no heating of the energy transmission surface 140. In still other embodiments, tissue heating may be done as a result of a combination of conductive heating caused by pre-heating or active heating of energy transmission surface 140 and radiant heating of tissue and/or the scleral shield. The energy transmission surface 140 may incorporate an energy-absorbing layer or pattern that may be pre-heated by light energy or other means, for example up to 42 degrees Celsius, prior to contact with the outer surface of the eyelid. Or, energy transmission surface may be made from a thermally-conductive material and may be heated by a heater that is thermally linked to energy transmission surface 140. In the case where energy transmission surface 140 is made from a thermally-conductive material, the material may be transmissive to an energy source (such as light) coming from energy transducer module 120, or it may be solid, opaque or otherwise not transmissive to another form of energy other than conductive heating. In the case where energy transmission surface 140 is opaque or non-transmissive, it may be made from a conductive metal such as copper or aluminum, in which case energy transmission surface 140 may be heated by an energy transducer module 120 comprising any means of heating a thermal mass (such as a resistive heater), and then pushed against the eyelid to conductively heat the eyelids. In the case where energy transmission surface 140 is transmissive to another form of energy as well as thermally conductive, it may be fabricated from materials such as sapphire, calcium fluoride, diamond, graphene and the like. In one preferred embodiment, up to three modes of heating may occur simultaneously: i) the inner surface of the eyelid is warmed using red or infrared light transmitted to an energy-absorbing scleral shield 300, ii) eyelid tissue is heated radiantly by visible light (e.g., green) which is absorbed by chromophores, and iii) eyelid tissue is heated conductively by bringing a pre-heated energy transmission surface 140 into contact with the outer surface of the eyelid. It will be appreciated that a significant advantage of using the light-based heating techniques described herein, and specifically infrared heating of an energy-absorbing surface, alone or in combination with the other two modes of heating (visible light heating of chromophores and conductive heating of the tissue), heating of the target tissue may be accomplished significantly faster than with any conventional method of conductive heating of the outer or inner eyelid surfaces. Specifically, with these combined modes, the meibomian gland tissue may be brought up to a temperature of, for example, about 40-42 degrees Celsius, in less than one minute. Specifically, in some cases, the meibomian gland tissue may be brought to about 40-42 degrees Celsius within 10, 15, 20, 25, 30 or 45 seconds.

As shown in FIG. 3A, a visualization device or means 160 may be used to view the eyeball 20. In some embodiments, the visualization means 160 may be part of eye treatment device 200. In other embodiments, the visualization means 160 may be a separate component. The visualization means 160 may include, for example, a magnifier, a camera, microscope, a slit lamp instrument, or other suitable visualization instrument.

In some embodiments, the scleral shield 300 may further include an image translator 155 that allows viewing of a transilluminated image of a portion of the eyelid and the meibomian glands. As described previously, the image translator may include, for example, one or more reflective surfaces, mirrors, light pipes, prisms, fiber bundles, image sensors or other suitable image translation means. As shown in FIG. 3A, the image translator 155 is integrated into scleral shield 300, but in other embodiments, the image translator 155 may be a separate component.

In some embodiments, an additional shielding element 258 may be used to prevent unwanted photonic energy (such as IR or blue/violet light) from reflecting off the transillumination element back to the clinician. For example, the shielding element 258 may be a thin, opaque shield or filter (blocking at least visible blue and IR light energy) that swings, flips, or slides (as indicated in FIG. 3A) into position over the image translator 155 and possibly also the energy transducer module 120 or energy transmission surface 140 during the heating and blue/violet light treatment modes, to protect the clinician. Alternatively, a portion of image translator 155 and/or visualization means may include a selective optical filter or photochromic element, such that during low-level illumination of the eyelid for purposes of evaluating transilluminated images of the meibomian glands, the photochromic element passes substantially all of the light, whereas during the heating mode where infrared energy or high-level visible light may be used, some or all of that energy may be attenuated, thereby shielding the clinician from harm.

By way of further clarification, several classes of embodiments will now be described. In one class of embodiments, devices are intended for self-administered use by individuals, typically in a home-use environment. For this class, scleral shields are not necessarily practical to use, and therefore, there can be a higher risk of unwanted forms of energy (such as certain wavelengths of light or infrared energy) penetrating the eyelids and reaching sensitive anatomy of the eye. As such, this class of embodiments may sometimes be limited to the use of safer forms of energy such as visible light in the range of 450-700 nm. In another class of embodiments, devices are intended for use by eye care professionals in a controlled office environment, where a treatment system having a scleral shield component can more likely be safely utilized. In this class, the scleral shield can be designed with shapes and materials to increase the likelihood that little or no damaging energy reaches sensitive eye structures.

IN-OFFICE DEVICE—Embodiments of the in-office device may include one or more of the following: diagnosing the meibomian glands; treating the meibomian glands; and antimicrobial treatment of the eye system. In one set of preferred embodiments, diagnosing the meibomian glands is carried out two ways. First, using visible or IR illumination from the energy transducer module which is directed toward the outer surface of the eyelid in order to view and evaluate the meibomian glands using the image translator, with or without the visualization means. Second, by slight compression of the eyelid while observing the eyelid margins to note the quantity and quality of oily secretions from the meibomian gland ducts. For treatment, in one set of embodiments, the eyelid is heated and compressed. Near infrared (NIR) energy from the energy transducer module at approximately around 800-900 nm is transmitted through the eyelid to the scleral shield, which then heats up and consequently warms the inner surface of the eyelid. Additionally, visible light from the energy transducer module in the range of about 500-600 nm (green light) is directed at the outer surface of the eyelid which heats the tissue by means of chromophore absorption. The energy transmission surface is then moved toward the eyelid by the clinician via direct or indirect manual control, in order to compress the eyelid between the energy transmission surface and scleral shield. Optionally, the energy transmission surface may be pre-warmed and/or actively warmed during the treatment to provide some conductive heating of the outer eyelid. The temperature of the inner and/or outer eyelid surface may be measured and displayed for the clinician. The clinician applies heating energy and compressive force while visually monitoring the eyelid margin to optimize the expression of meibum from clogged meibomian glands. Finally, the energy transducer module may produce blue/violet light in the range of about 400-450 nm to reduce and/or eliminate bacteria in the eye system 10.

HOME-USE DEVICE—Embodiments of the in-home device use visible light transmitted through the energy transmission surface from the energy transducer module aimed at the outer surface of the eyelid to heat the tissue by means of chromophore absorption. In certain preferred embodiments, the visible light may be high-intensity broad spectrum (e.g., white) LED light passing through certain filters, or it may be a green, greenish-yellow, or greenish-white LED (500-600 nm) with no filters. In some embodiments, the energy transmission surface is transparent to visible light and is thermally conductive, allowing warming (e.g. to 42 degrees Celsius) prior to or during compression of the surface against the eyelid (see FIG. 2A). In some embodiments, the energy transmission surface may have an extension element 143 (such as in FIG. 2B and described previously) that allows most of the light energy to pass through it, while keeping a gap between the energy transducer module and the eyelid surface 12, 14 (to enable passive or active air cooling of the eyelid, for example). The energy transmission surface may conform to the shape of the eyelid and apply pressure to the surface of the eyelid to shorten the optical path length of radiant energy. In some embodiments eyecups are utilized to prevent light from escaping from the immediate treatment area and to keep at least a portion of the device at a predetermined distance from the eyelids or periocular region.

FIGS. 4A-4C are representative of another embodiment of an eye treatment device. FIG. 4A is a schematic side plan view of an eye treatment device 200. The eye treatment device 200 shown in FIG. 4A is positioned adjacent to an eyeball 20 for treatment of the eyeball for MGD, blepharitis and other medical conditions. For simplicity, sensitive eye structures such as the cornea, iris, pupil lens, and adjacent elements are depicted in FIGS. 4A-D, 5A-B, 6, 11A-B, 12, 13 and 15A as a single element called anterior eye structures 27. The eye treatment device 200 can include configurations of the modules depicted in FIGS. 2 and 3, along with additional components useful in operation of the eye treatment device 200. The eye treatment device 200 can include a power source module 110, a controller 212, an energy transducer module 120, an energy waveguide in the form of reflector 210, and an energy transmission surface 140. The energy transducer module 120 of some embodiments may include an LED device formed of one or more of an LED emitter 207, an LED lens 208, and an energy transducer module driver 209. Each of these components, either alone, or in combination with other components (either shown herein or not disclosed) can correspond or be part of the modules described in relation to FIGS. 2A-2H. The components of the eye treatment device 200 can be contained in a housing 202. Some of the embodiments of the eye treatment device 200 may also include a consumable portion 260 and/or a scleral shield 300, such as shown in FIGS. 3 and 6.

The energy transducer module driver 209 can comprise any LED-powering and controlling circuitry, whether configured as an actual printed circuit board, an integrated circuit, or discrete components. In some embodiments, it serves the function of an LED driver, providing a controlled current, voltage or power level through the LED emitter 207 within the LED specifications to provide a desired illumination intensity therefrom. Optionally, the LED printed circuit board can include a pulse-width modulation function, PID circuit, or similar scheme in order to modulate the effective intensity of the emissions over time to achieve a desired heating of a target region of the eyelid.

The energy transmission surface 140 can be positioned relative to the housing 202 at a location distal to the energy transducer module 120, and positioned in between the energy transducer module 120 and the tissue treatment site of the eye system 10. Positioned in this manner, the energy transmission surface 140 can pass, or receive and transmit, the electromagnetic energy transmitted from the energy transducer module 120. The energy transmission surface can be a concave shape, such that the energy transmission surface 140 corresponds to the shape of the eyelids 12, 14 when closed and covering the eyeball 20. The energy transmission surface 140 may be an integral part of housing 202 and may substantially seal the distal end of the eye treatment device 200. Additionally, energy transmission surface 140 may move independently, or with energy transducer module 120, relative to housing 202. A sealing element such as a bellows, gasket, o-ring or similar sealing means may be used to prevent contamination of the interface between the movable elements and the housing.

In some embodiments, the energy transmission surface 140 is positioned adjacent to the eyelids 12, 14, and does not physically contact the eyelids 12, 14, but instead transfers heat to the treatment tissue radiantly. The energy transmission surface 140 can be substantially transparent to the desired electromagnetic energy transmitted by the energy transducer module 120 to allow for the transmission of the thermal energy from the energy transducer module 120 without significantly hindering the desired energy type or wavelength from reaching the treatment tissue. In some embodiments, the energy transmission surface 140 can be made of an optical plastic, sapphire, glass, calcium fluoride, or fiberglass. It can have an easy to clean outside surface and can be scratch resistant. In some embodiments, the energy transmission surface 140 can be configured to operate in conjunction with the energy transducer module 120 to filter unwanted wavelengths from reaching the treatment tissue or other portions of the eye system 10. For example, in some embodiments, the illumination source may transmit electromagnetic energy in both the IR and visible light spectra. The energy transmission surface 140 can be used to allow passage of, for example, the energy from the visible light spectrum, but filter out the energy from the IR spectrum. Likewise, if it is desired that only energy from one color reach the treatment tissue, the energy transmission surface 140 can be used as a bandpass filter or be used with a filter to restrict passage of energy of wavelengths other than the color desired. Alternatively, as described previously, energy transmission surface 140 may include a single-use outer eyelid pad 147. Such outer eyelid pad 147 may be transparent to all relevant wavelengths of light or other forms of energy, or it may have desirable filtering properties, and it may additional include a temperature or pressure sensor.

In some embodiments, the energy transmission surface 140 can be configured to come in physical contact with the eyelids 12, 14 and may conductively transfer heat to the treatment tissue (or facilitate cooling of the eyelid, as described below). In other embodiments, a preponderance of tissue heating occurs as a result of radiant heating from the energy transducer module 120, wherein substantially all of the desired electromagnetic energy passes through energy transmission surface 140 and is absorbed by the tissue, thereby causing heating of the tissue and little or no heating of the energy transmission surface 140. It will be appreciated that the device may be configured without an energy transmission surface 140. However, the energy transmission surface 140 provides certain benefits such as ease of cleaning of the primary patient contact surface, as well as the potential for the energy transmission surface 140 to assist in keeping the outer surface of the eyelid within a desired temperature range, and to provide a convenient location for certain safety sensors. In embodiments where a single-use outer eyelid pad 147 is used as part or all of the energy transmission surface 140, the outer eyelid pad 147 may contain a temperature sensor, but preferably a non-contact temperature sensor is utilized instead, such as a thermopile or pyroelectric sensor, positioned proximal (relative to the housing) to the outer eyelid pad 147. In such embodiments, the outer eyelid pad 147 is preferably transparent to the wavelengths of infrared that the non-contact temperature sensors are designed to sense.

FIG. 4B is a schematic front plan view of the energy transducer module 120 of the eye treatment device 200. As shown in FIG. 4B, the LED emitter 207 can be arranged as an array of individual LEDs. As represented, the LED emitter 207 is arranged in a 3×3 array of LEDs (such as in the LZ9 configuration offered by LED Engine, Inc.), though the LED emitter 207 is not limited to this arrangement and can include arrays of varying numbers of LEDs arranged in varying arrays of columns and rows; and some embodiments may include a single LED or other type of illumination source. The reflector 210 may partially or fully surround the LED emitter 207, such that it can direct the emission of light from the LED emitter 207 in a desired manner. The LED lens 208 can be positioned over the LED emitter 207 and positioned within the internal diameter of the reflector 210.

FIG. 4C is a schematic side plan view of one embodiment of an eye treatment device 200, wherein the device is operational and transmitting light 211 to the eye system 10 and the treatment tissue. In FIG. 4C, the light 211 is emitted from the energy transducer module 120. Some portion of the light 211 may initially be radiated at an angle such that light, without correction, would not reach the energy transmission surface 140 for passage to the treatment tissue. As shown, the reflector 210 may reflect or guide the angled light towards the energy transmission surface 140, thereby improving the efficiency of heating the target tissue. Portions of the light 211 may also be transmitted directly from the energy transducer module 120 to the energy transmission surface 140.

FIG. 4D is a schematic side plan view of another embodiment of an eye treatment device 200. In this embodiment, the transmission of the light 211 may be administered without the aid of a reflector 210, if, for example, other components of the eye treatment device 200 can be used to control the direction and intensity of the light 211 such as a specially shaped lens, an additional lens element, a light pipe, a total internal reflective (TIR) element, a refractive element, a diffractive element, a mirror element, a diffuser, and the like, or a combination thereof. It may be desirable in this manner to control the focus and the intensity of the light energy so that the light energy penetrates deeply into, but not significantly beyond, the target tissue in the eyelids 12, 14, such as the meibomian glands. In some embodiments, the energy transmission surface 140, acting as a lens or with a lens, may be used to focus and direct the light 211 to the desired treatment tissue and away from the central ocular axis, to avoid the anterior eye structures 27 of the eyeball 20 and other sensitive anatomy of the eye such as the retina. It will be appreciated that the region along which the upper eyelid 12 and lower eyelid 14 meet may vary from one individual to another; in most individuals the region is generally below the central ocular axis. However, for purposes of demonstrating how certain embodiments can mitigate the risk of excessive light 211 penetrating the eyelids at the central ocular axis, the worst-case situation of having the eyelids meet at the central ocular axis is shown. It will be further appreciated that at least some of the risk associated with excessive rays penetrating the eyelids and reaching sensitive tissues may be mitigated by having the individual being treated move his/her eyeball off-axis, such that most of the rays penetrating the eyelids only reach the sclera, which is generally less sensitive.

Figure 4E:
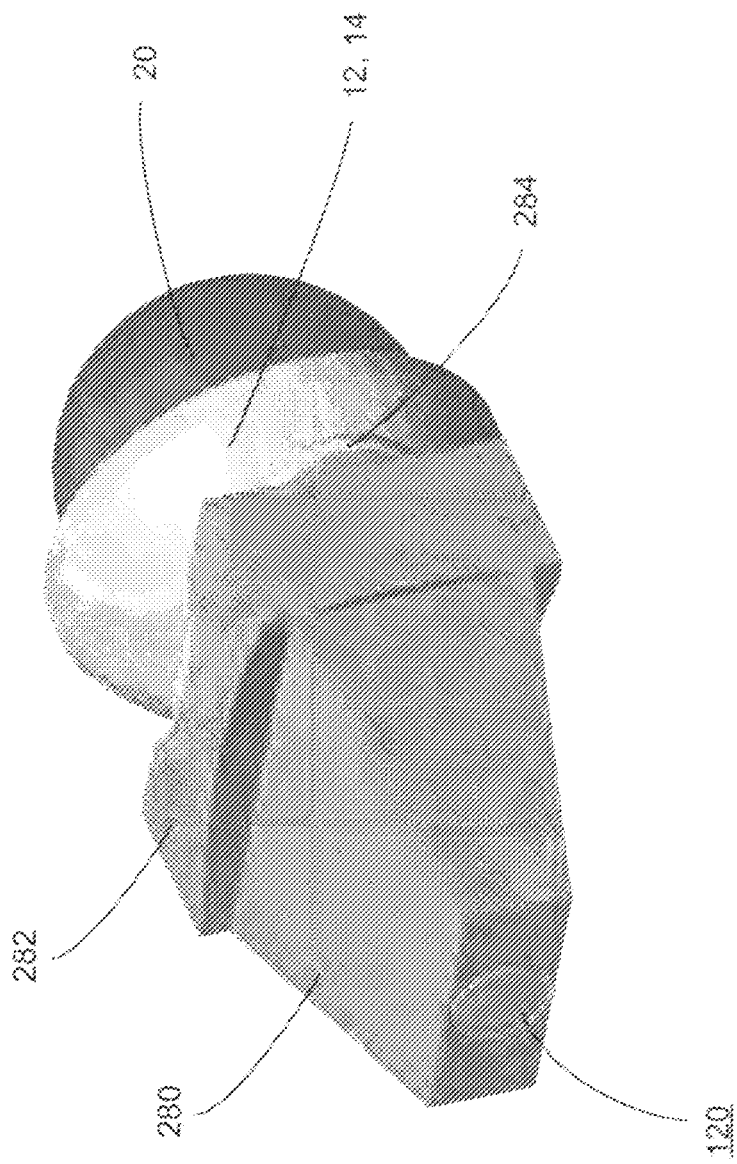
FIG. 4E is a perspective view of the optical elements in another embodiment of an eye treatment device.
Figure 4G:
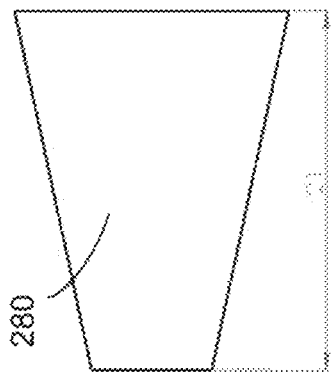
FIGS. 4F-H are front, side and cross-section views of the prism element from FIG. 4E.
Figure 4F:
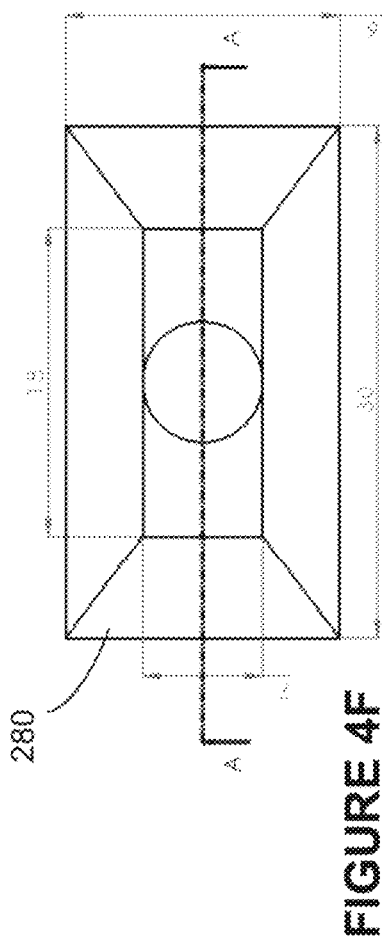
Figure 4H:
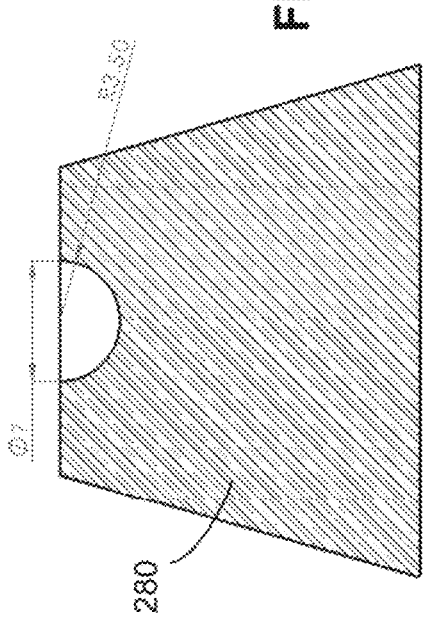
Figure 4M:
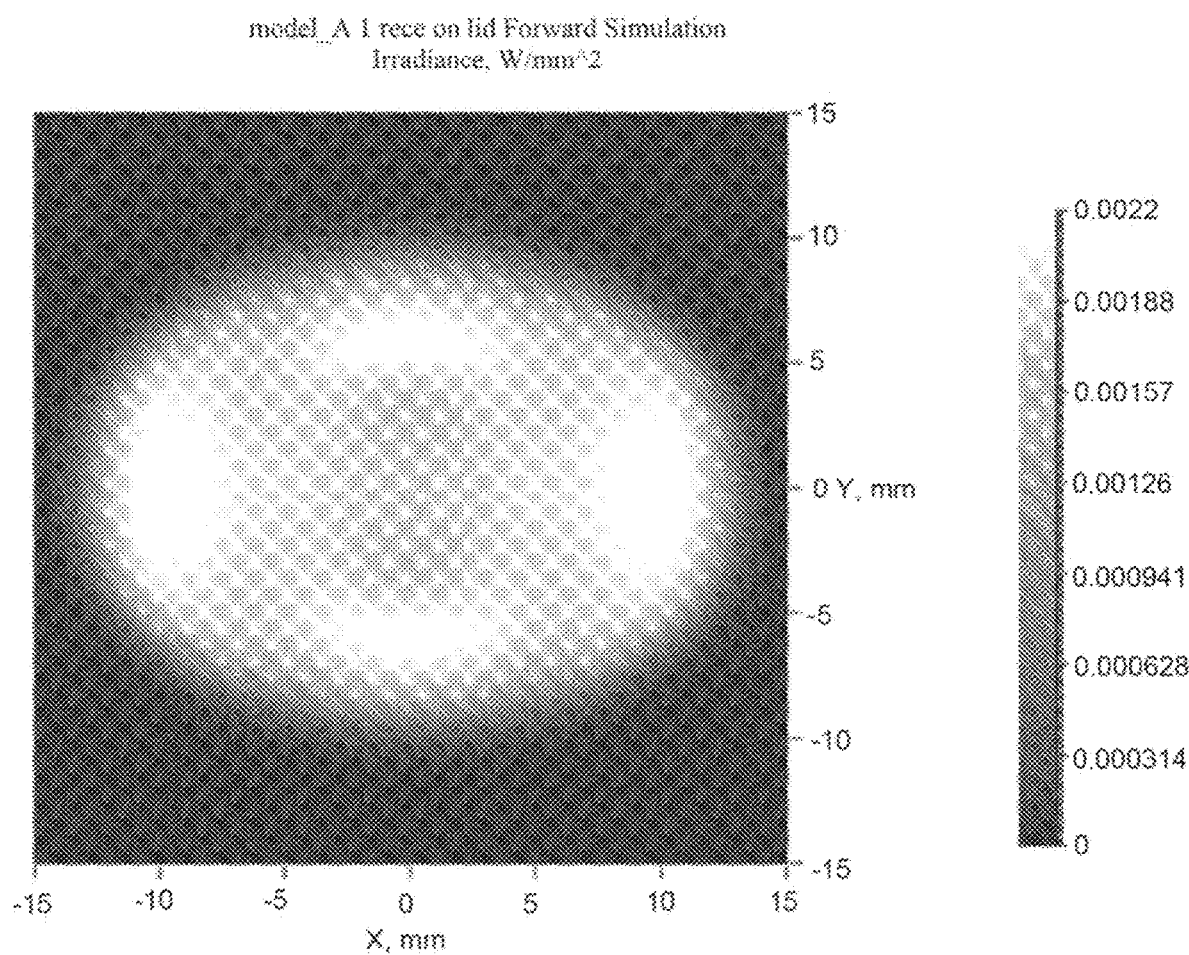
FIGS. 4M and 4N are theoretical graphical representations of the irradiance patterns produced by the optical elements of 4E.
Figure 4N:
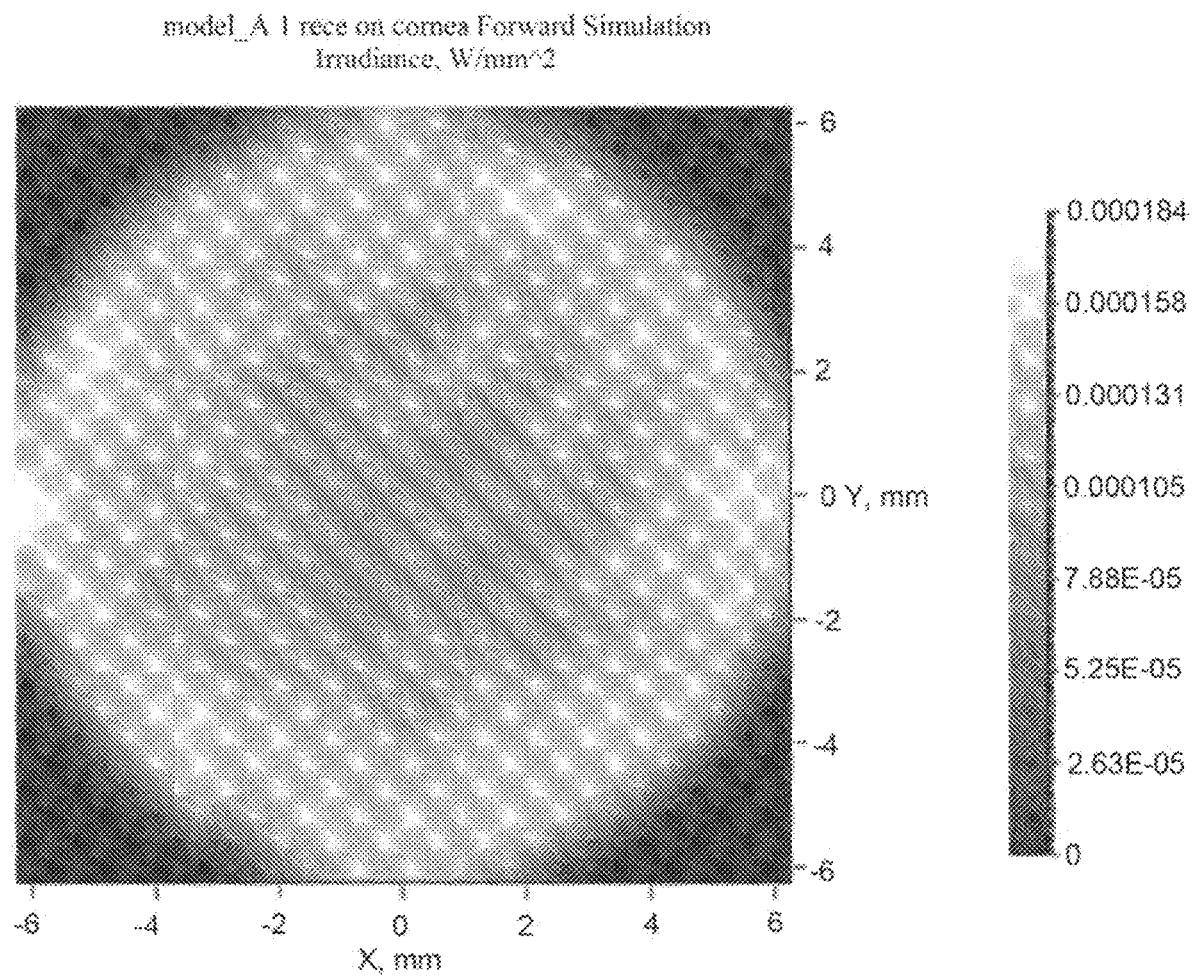

FIG. 4E shows a particular embodiment comprising additional optical elements to improve the distribution of light energy across the eyelid surface, while minimizing the amount of light passing directly through the central ocular axis. Energy transducer module 120 comprises an LED such as an LZ9 from LED Engin Inc., a prism 280, a shaping lens 282, and face glass 284 (serving a similar function as energy transmission surface 140 in other embodiment disclosed herein). Eyelids 12, 14 and eyeball 20 are also shown in relation to the optical elements. In this particular design, the prism is a glass element with 6 polished surfaces and one half ball concave surface with radius 3.5 mm to accommodate the LED. There is no coating on the prism surfaces. Entrance and exit surfaces can have anti-reflection coating (optional) which increases the efficiency by about 5-6%. FIGS. 4F-H show exemplary details of the shape and dimensions of prism 280. The material may be BK7, and the surfaces are preferably polished. FIG. 4F is a front view, FIG. 4G is a side view, and FIG. 4H is a section view through section A-A. FIGS. 4I-L show exemplary details of the shape and dimensions of shaping lens 282. FIG. 4I is a front view, FIG. 4J is a section view through section A-A, FIG. 4K is a side view, and FIG. 4L is a perspective view. FIGS. 4M and 4N show the theoretical optical performance of the system described in FIGS. 4E-L above. FIG. 4M shows the light distribution, measured as irradiance in Watts per square millimeter, on the surface of the eyelids, wherein the light distribution is shown to be fairly uniform (as opposed to shining the LED of energy transducer module 120 directly at the eyelids or through a plain glass energy transmission surface, in which case most of the light would be projected in the middle of the lid and very little would reach the edges). The total calculated flux is 0.86 Watt, the maximum irradiance is 2.2 milliwatts per square millimeter and the uniformity is estimated at about 80%. FIG. 4N shows the amount of irradiance reaching the eye (i.e., passing through the eyelid tissue). The total calculated flux is 0.019 Watts, and the maximum irradiance is 0.18 milliwatt per square millimeter.

Figure 5A:
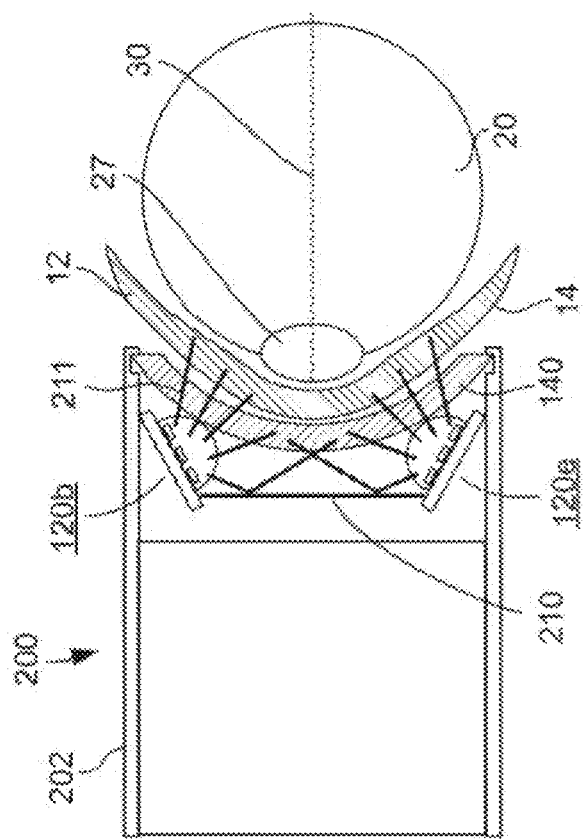
FIG. 5A is a schematic side plan view of a further embodiment of an eye treatment device.
Figure 5B:
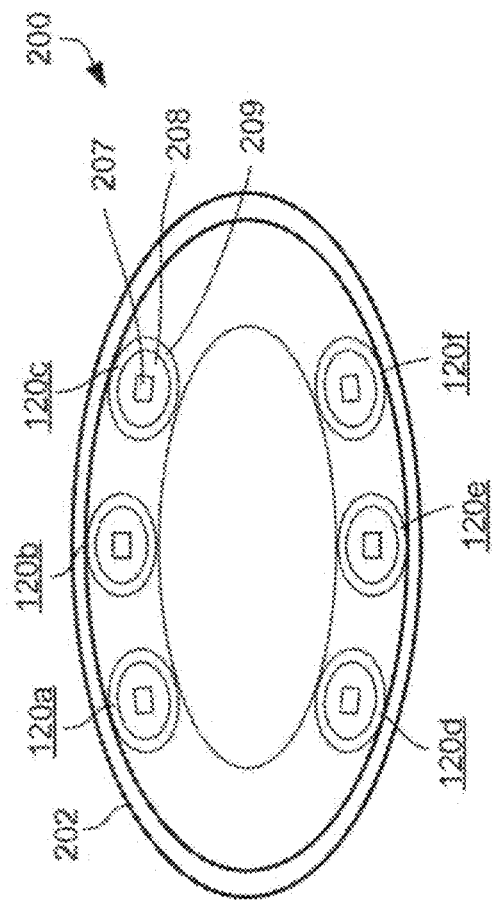
FIG. 5B is a schematic front plan view of the eye treatment device embodiment of FIG. 5A.
Figure 5C:
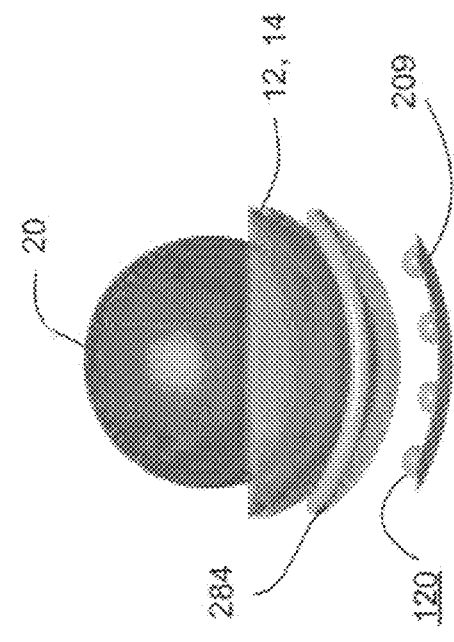
FIGS. 5C-F are side, top, front and perspective views of portions of another device embodiment.
Figure 5D:
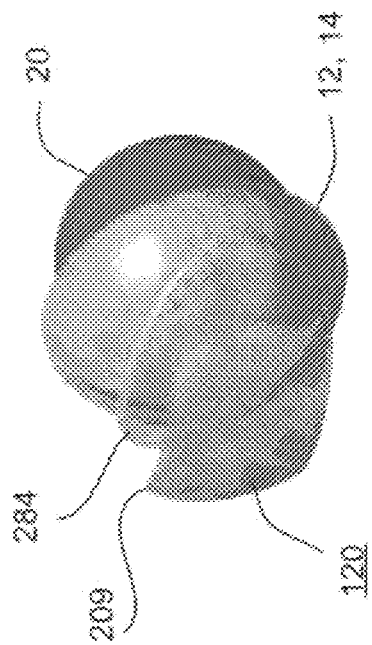
Figure 5E:
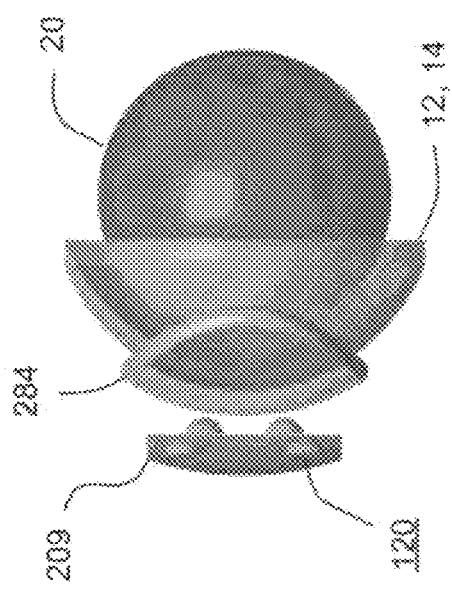
Figure 5F:
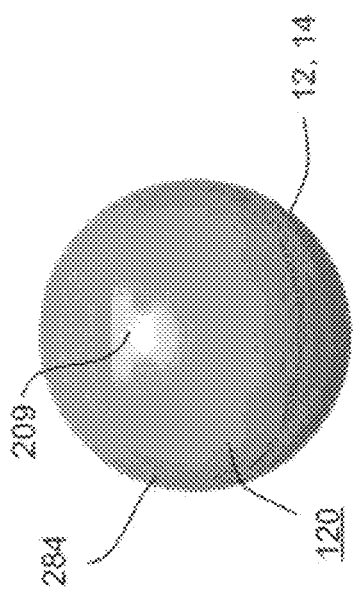
Figure 6:
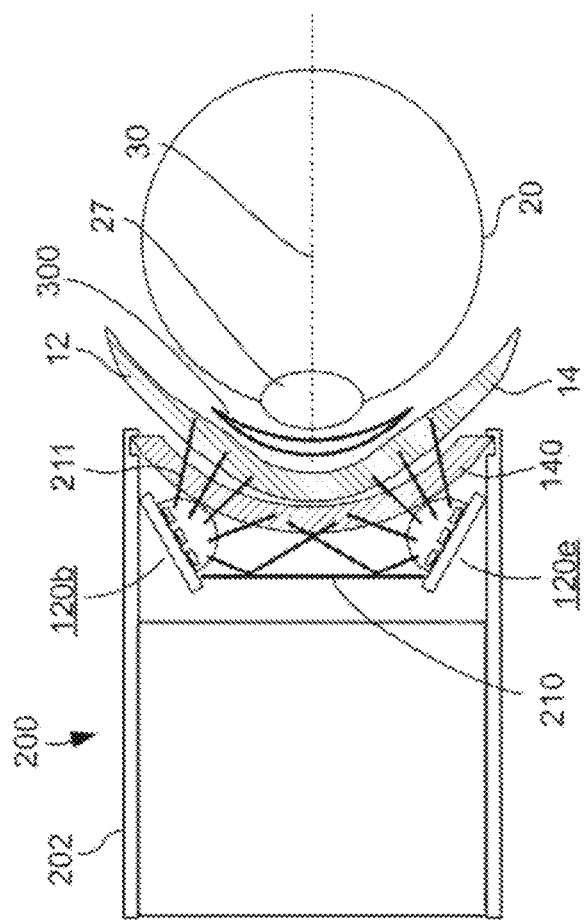
FIG. 6 is a schematic side plan view of an embodiment of an eye treatment system, which includes an eye treatment device and a scleral shield.

FIGS. 5A and 5B are representative of one embodiment of an eye treatment device 200. FIG. 5A is a schematic side plan view of the eye treatment device 200 and FIG. 5B is a schematic front plan view of the eye treatment device 200. The embodiment of the eye treatment device 200 may contain components similar to those shown in FIGS. 4A-4C, including the power source module 110 and the controller 212, though such components are not shown in FIGS. 5A and 5B. FIG. 5A provides a different configuration for the energy transducer module 120 in order to focus and control the direction of the light 211. In some embodiments, the eye treatment device 200 can include multiple energy transducer modules 120, such that at least one energy transducer module 120a can be positioned in an upper region of the eye treatment device 200 to provide electromagnetic energy (e.g., light 211) to the target tissue within the upper eyelid 12 and at least one energy transducer module 120b can be positioned in a lower region of the eye treatment device 200 to provide electromagnetic energy (e.g., light 211) to the target tissue residing in the lower eyelid 14. Having separate energy transducer modules 120a, 120b positioned separately in the eye treatment device 200, allows the eye treatment device 200 to direct light energy directly toward the target tissue within the upper eyelid 12 and the lower eyelid 14 and reduces the amount of light that may be directed towards sensitive anterior eye structures 27 along the central ocular axis 30.

As shown in FIG. 5A, use of the eye treatment device 200 for treatment of an eye condition such as MGD and blepharitis, can include positioning the energy transmission surface 140 of the eye treatment device 200 adjacent to, or in contact with, the closed upper and lower eyelids 12, 14 of a patient. With the eye treatment device 200 positioned in this way, the upper energy transducer module 120a can be positioned above the central ocular axis 30 to provide electromagnetic energy in the form of light 211 to the meibomian glands 18 within the upper eyelid 12, and the lower energy transducer modules 120 b can be positioned below the central ocular axis 30 to provide electromagnetic energy in the form of light 211 to the meibomian glands 18 within the lower eyelid 14. The eye treatment device 200 can also include a reflector 210 positioned behind the upper and lower energy transducer modules 120 to reflect back any light to the treatment tissue.

As depicted in FIG. 5A, the upper and lower energy transducer modules 120 can be tilted at an angle, each having a central optical axis directed substantially at an oblique angle to the surface of each eyelid, such that the majority of light energy passing into each eyelid is absorbed before reaching the sensitive anterior eye structures 27 of the eyeball 20. In some embodiments, the upper and lower energy transducer modules 120 can have other directional orientations. For example, in some embodiments, the upper and lower energy transducer modules 120 can be positioned such that each central optical axis of the illumination sources is substantially horizontal. As such, the light 211 transmitted from the energy transducer modules 120 configured in this way can travel horizontally from the energy transducer modules 120 to the energy transmission surface 140 and may then be refracted, diffracted, or reflected at an angle toward the treatment tissue, in a manner that maximizes penetration, absorption and heating in the targeted regions of the eyelids while minimizing the proportion of light that reaches the sensitive anterior eye structures 27.

The eye treatment device 200 of the embodiments shown in FIGS. 5A and 5B can include more than one energy transducer module 120 in each of the upper and lower regions of the eye treatment device 200. For example, as shown in FIG. 5B, the eye treatment device 200 can include three separate energy transducer modules 120a-c in the upper region and three separate energy transducer modules 120 d-f in the lower region. Other numbers of energy transducer modules 120 are contemplated, such as, for example 2, 4, 5, 6, 7, 8, 9, 10, etc. energy transducer modules 120 in each of the upper and lower regions of the eye treatment device 200. Positioning multiple energy transducer modules 120 laterally in the upper and lower regions of the eye treatment device 200 allows for improved coverage and distribution of the electromagnetic energy across the width (side-to-side) of the upper and lower eyelids 12, 14 to better reach the full width of the target tissue (e.g., the meibomian glands within the eyelids 12, 14). Also as shown in FIG. 5B, the upper and lower energy transducer modules 120a-c, 206d-f can be arranged in an arc pattern to follow the upper and lower contours of the eyeball.

It is also contemplated, though not depicted in FIG. 5B, that the upper and lower illumination regions of the eye treatment device 200 can be fitted with more than one row of energy transducer modules 120. For example, in FIG. 5B one or more additional energy transducer modules 120 could be positioned above or below each of the energy transducer modules 120a-c. Including additional rows of energy transducer modules 120a-c can provide additional vertical coverage and distribution of the electromagnetic energy directed to the target treatment tissue. It is additionally contemplated, though not depicted, that the eye treatment device 200 may include two sets of energy transducer modules 120, reflectors 210, and energy transmission surfaces 204 within a housing, configured like binoculars, to be positioned adjacent to, or against, both of a patient's eyes simultaneously. Devices of such embodiments may speed up the treatment time, as both eyes can be treated at the same time.

Figure 5G:
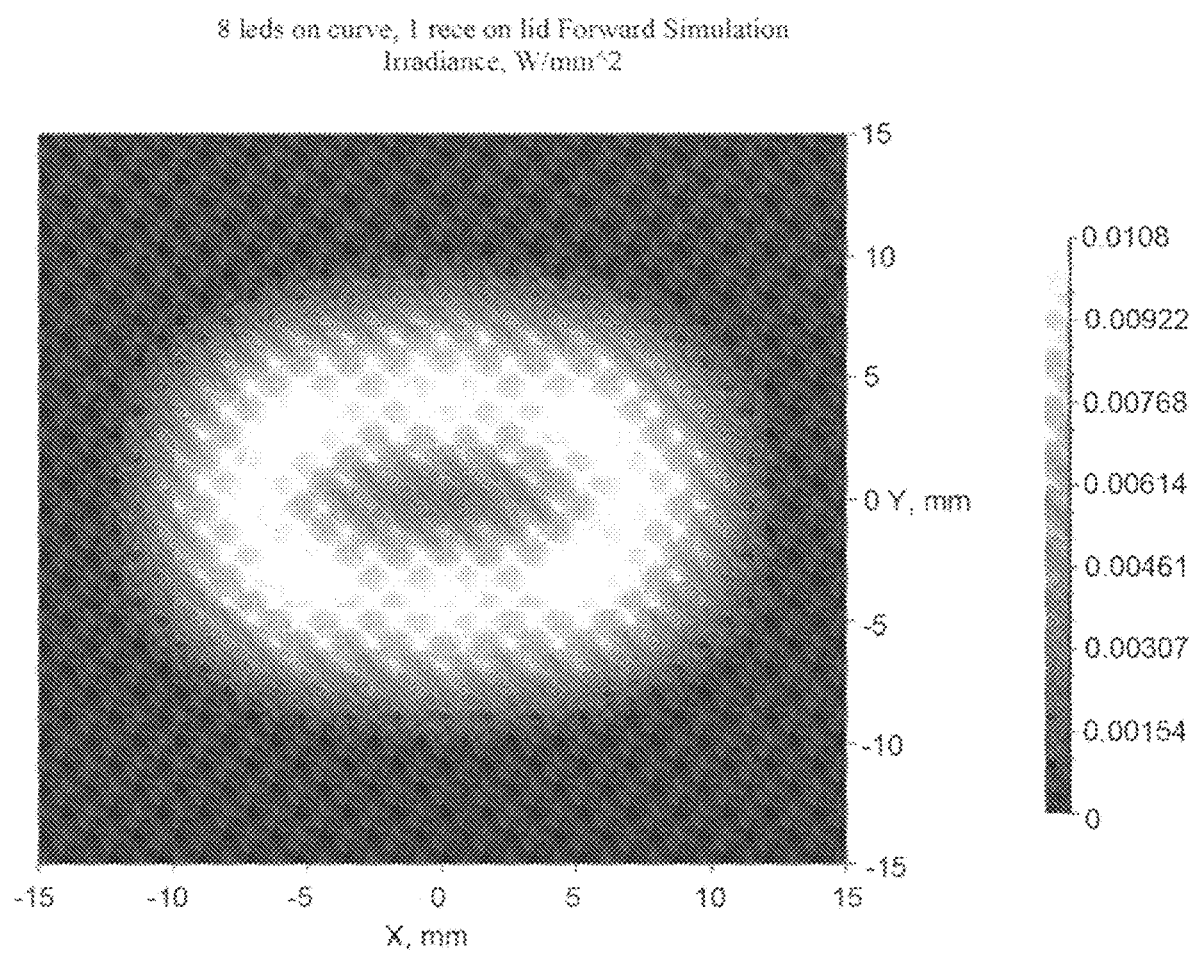
FIGS. 5G and 5H are theoretical graphical representations of the irradiance patterns produced by the optical elements of 5C-F.
Figure 5H:
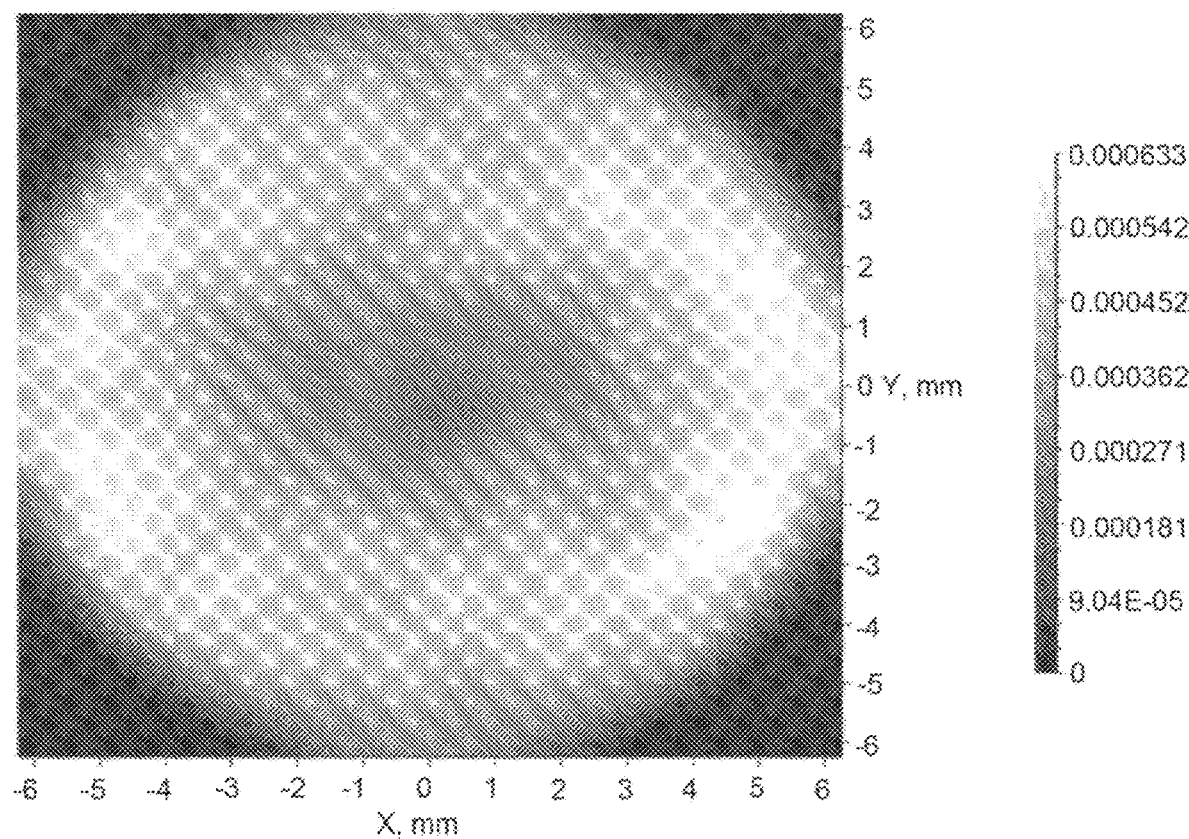

FIGS. 5C-F show side, top, front and perspective views, respectively, of an 8-LED configuration, similar to that depicted in FIGS. 5A-B (only with eight LEDs 120a, 120b instead of six). The eight LEDs 120a, 120b may be of an LZ1 type from LED Engin, Inc., and are shown arranged on a spherically curved surface, which may be a circuit board or an energy transducer module driver 209, positioned behind face glass 284 whose shape matches the curvature of eyelids 12, 14 adjacent to eyeball 20. FIG. 5G shows the calculated irradiance pattern onto eyelids 12, 14, with a total flux of 2.7 Watts and a maximum irradiance of 10.7 milliwatts per square millimeter. FIG. 5H shows the calculated irradiance passing through the eyelids, with a total flux of 0.07 Watts and a maximum irradiance of 0.6 milliwatts per square millimeter. It will be appreciated that the pattern of irradiance in FIGS. 5G and 5H are less uniform than the patterns shown in FIGS. 4N and 4P. The trade-off between the two designs is compactness of the device versus uniformity. The designs of FIGS. 4E-L include a rather large prism, while the designs of FIGS. C-F do not include any optical elements other than the LEDs and lenses and the face glass. Those skilled in the art may combine the two approaches, for example, by adding one or more prisms 280, shaping lenses 282, or other elements such as diffusers, gratings and the like, to the designs of FIGS. 5C-F, in order to optimize the uniformity of light distribution while keeping the size of the device as compact as possible.

FIG. 6 is a schematic side plan view of an eye treatment device 200, such as the eye treatment device 200 depicted in FIG. 5A. Also shown in FIG. 6 is a scleral shield 300, which, in conjunction with the eye treatment device 200, can provide a system of treating the target tissue with increased safety and efficacy. The scleral shield 300 can be positioned under eyelids 12, 14 and adjacent to the patient's eyeball 20 to cover sensitive anterior eye structures 27. For example, the scleral shield may be positioned (referring to FIG. 1) over the sclera 21 and cornea 22 and may also provide protection to other internal anatomy of the eye such as the iris 24, pupil 25, lens 26, and other light sensitive anatomy of the eye system 10.

Figure 7E:
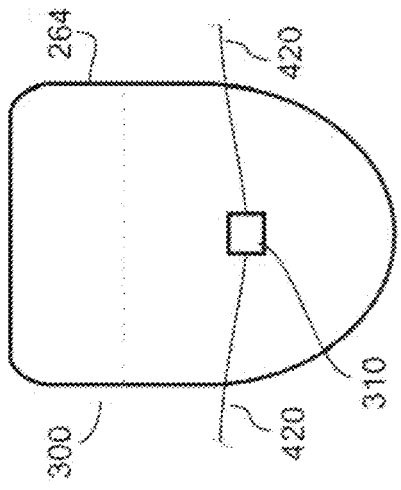
Figure 7G:
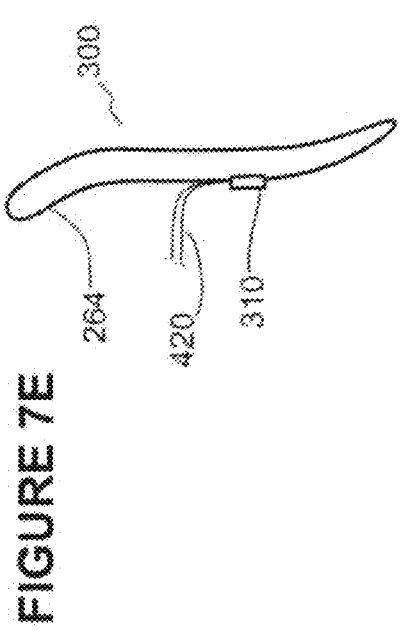
Figure 7F:
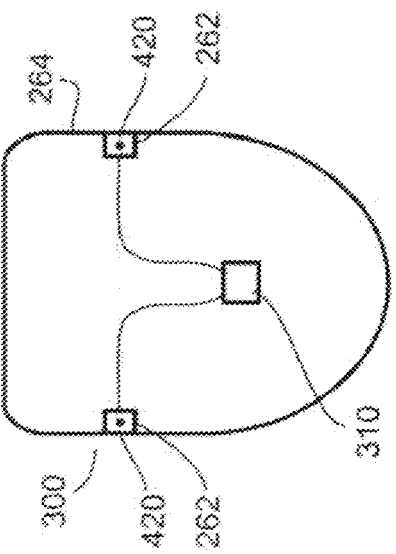

Referring back to FIG. 6, the scleral shield 300 may be of similar disc shape as a contact lens, or it may be substantially larger to cover the entire cornea and optionally at least some of the sclera (as in the case of a conventional corneal shield), or it may have a partial disc or paddle shape, similar to the under-lid portion of a Mastrota paddle. Shield 300 may be positioned in the eye prior to treatment with the eye treatment device 200, or it may be integral with eye treatment device 200, and therefore placed in the eye or under the lid during the treatment. In addition to providing basic safety benefits, the scleral shield 300 can also allow for increased efficacy of the eye treatment device 200. For example, in some circumstances, the intensity of the energy emanating from the energy transducer modules 120 must be modulated to prevent injury to the sensitive eye anatomy; however, when the eye anatomy is protected by the use of the scleral shield 300, the intensity of the electromagnetic energy directed from the energy transducer modules 120 can be increased. As shown in FIGS. 7E-7G, the scleral shield 300 may include a top curved portion 264 of the shield that prevents scattered photonic energy from reaching the cornea, lens, iris and pupil. Though the scleral shield 300 is shown in FIG. 6 to be used in the conjunction with the embodiment of the eye treatment device 200 described in relation to FIGS. 5A and 5B, it will be appreciated by the skilled artisan that the scleral shield 300 can be used in conjunction with any of the embodiments of the eye treatment device 200 disclosed herein to create a system for safe and efficacious treatment of eye disorders.

It will be further appreciated that the scleral shield 300 may include features which provide even more benefits to the device. For example, the scleral shield 300 of some embodiments is configured to reflect energy away from the eyeball and toward the inner eyelids, providing heating to the inner eyelids. In some embodiments, the scleral shield 300 may also include an image translator 155, as discussed above. The image translator 155 allows viewing of the inner side of the eyelid 14 and transillumination of the meibomian glands from behind the eyelid. In some embodiments, the scleral shield 300 may be made of an energy-absorbing material or have an energy transmission surface on a front face 302 for heating the meibomian glands from behind the eyelid during treatment. The energy-absorbing material may be a visible light or IR-absorbing material or surface made of black plastic or coated with a black substance, either of which may contain carbon black (e.g. 5% or more) or other material which absorbs light energy such as red light and NIR.

Additionally, as shown in the schematic front plan views of the scleral shield 300 in FIGS. 7A-7H, the shield 300 may incorporate one or more temperature sensors 310 on the front or back surfaces of the shield 300. The shield 300 may also include data transmission means 320, so that temperature data may be sent to the eye treatment device 200 in order to monitor or modulate the treatment session, so that the inner surfaces of the eyelids may reach a target temperature without exceeding a predetermined threshold, along with ensuring that the sensitive tissues of the eye do not exceed another predetermined threshold. In some embodiments, such as the embodiment of FIG. 7A, the shield 300 has an embedded power source 330, an array of temperature sensors 310, and a data transmission means 320, which transmits data wirelessly, such as by RF, to an external interrogator 400 (which may be incorporated into the eye treatment device 200). In some embodiments, the data transmission means 320 includes an antenna embedded in the shield 300. In another embodiment, such as the embodiment depicted in FIG. 7B, the shield 300 may be passive (without a power source 330) and configured to be interrogated by an external interrogator 400 (which may be incorporated into the eye treatment device 200) using RF. For example, the external interrogator 400 shown schematically in FIG. 7B may be configured to provide power to circuitry in the shield 300 adequate to measure the temperature(s); the interrogator 400 may also provide power to a transmitter to send the temperature data back to the interrogator 400. In yet another embodiment, such as the embodiment of FIG. 7C, the shield 300 may be fully passive and contain one or more temperature sensors 310 in resonant circuits whose points of resonance will be modulated by changes (such as resistance) in the temperature sensors 310, and whose points of resonance can be detected by sweeping an external RF field, for example using the external RF sweeper 410 depicted schematically in FIG. 7C, and monitoring the impedance or other characteristic of the field. In a further embodiment, such as the embodiment of FIG. 7D, the shield 300 may be physically linked to an external device such as an interrogator or eye treatment device 200 (e.g. of FIG. 3A) via a wire or wire array 420 extending from the shield 300 to an external device, wherein such external device may provide power to the active elements in the shield 300 and send and receive data to and from the shield 300. Wire or wire array 420 may comprise conventional stranded or solid wire conductors with thin-wall insulation, or they may be embedded in more substantial structural insulation.

FIGS. 7E and 7E are schematic side and front plan views of the shield 300 having a temperature sensor 310 in the middle and one wire 420 coming out of each side of the shield. The upper curved portion of the shield 264 is used to protect the patient's cornea, lens, iris and pupil from the light or IR energy. The temperature data from the temperature sensor 310 may be sent to the eye treatment device 200 via the wires 420 in order to monitor or modulate the treatment session, ensuring that the inner surfaces of the eyelids reach a desired temperature range without exceeding a predetermined threshold, along with ensuring that the sensitive tissues of the eye do not exceed another predetermined threshold.

Figure 7H:
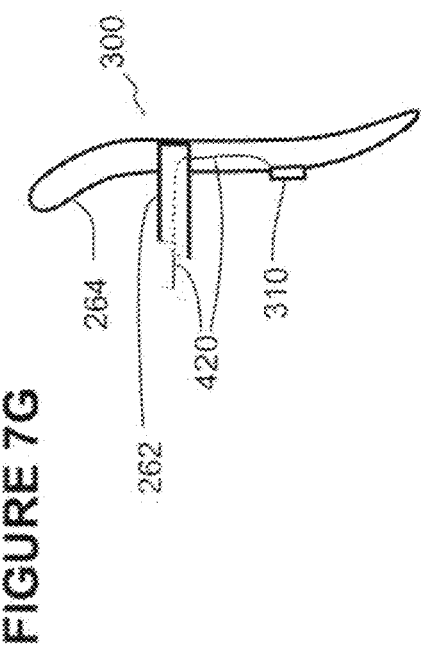

FIGS. 7G and 7H are schematic side and front plan views of the shield 300 having a temperature sensor 310 in the middle and one wire 420 coming out of each side of the shield. In these embodiments, scleral shield 300 may be coupled to the housing 202 with one or more support arms 262, with the wires being positioned on or within the arms, and, in certain embodiments, with the structural portion of support arms 262 made from insulating materials surrounding or otherwise channeling the conductive portions of wire or wire array 420.

Figure 8:
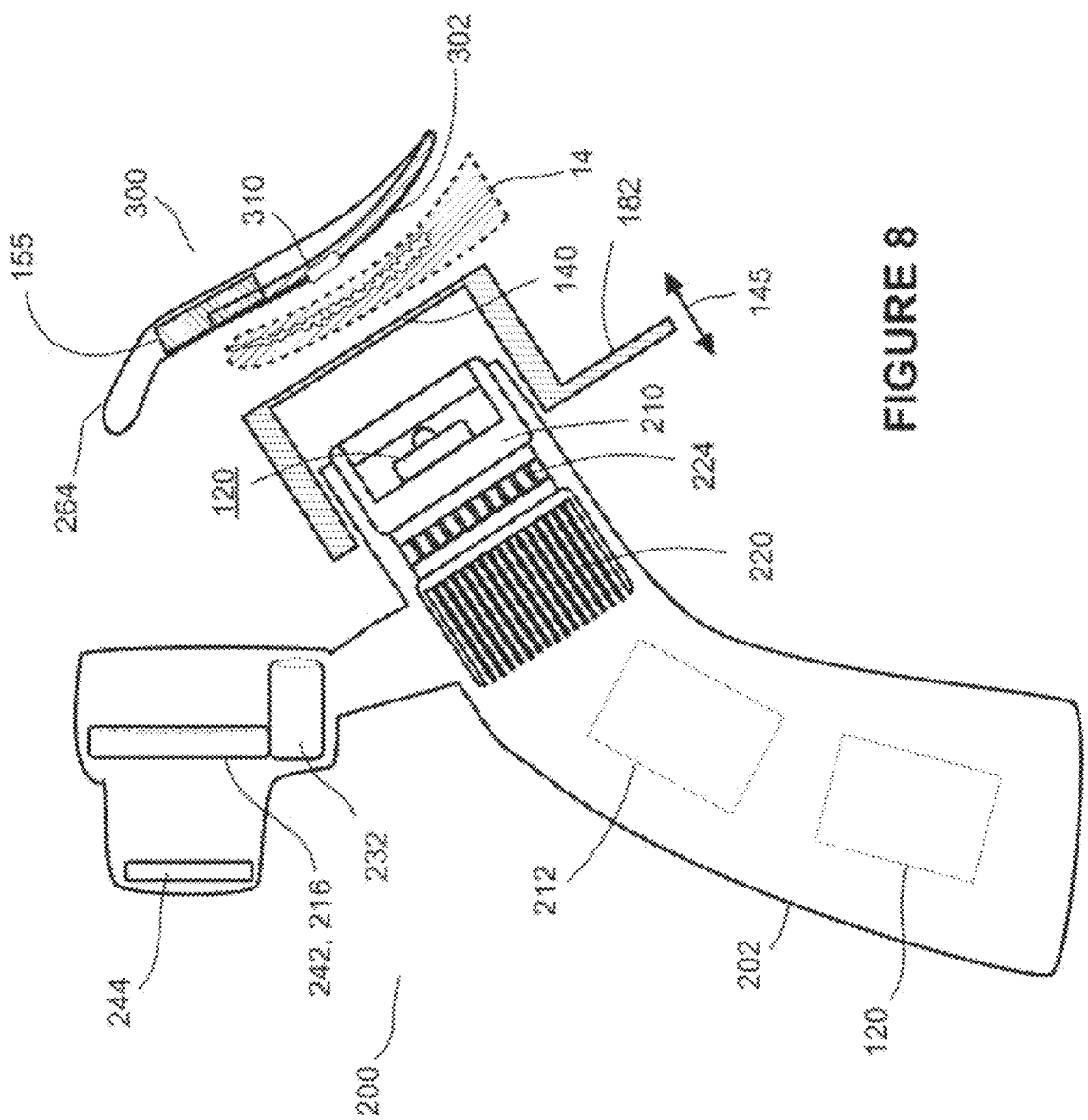
FIG. 8 is a schematic side plan view of another embodiment of an eye treatment device.

FIG. 8 depicts a side view of another embodiment of an eye treatment device 200. In some embodiments, such as the presently depicted embodiment, the eye treatment device 200 is configured to apply energy to one eyelid at a time in order to further protect the tissue of the eye from harm or discomfort. In such a configuration, the energy transducer module 120 within the housing 202 is sized to target the meibomian gland and surrounding tissue of one eyelid, for example, the upper eyelid 12 of FIG. 1 or the lower eyelid 14 of FIG. 1 and the energy transmission surface 140 is in a slidable relationship along movement path 145 with the energy transducer module 120. In such embodiments, the energy transmission surface 140 is also sized for placement along one eyelid at a time. In use, a patient using such an eye treatment device 200 may be instructed to open an eye widely, thus ensuring that the eyelid is relatively far away from the sensitive anterior eye structures and the central ocular axis.

In some embodiments, the eye treatment device 200 includes one or more features to help ensure the eye treatment device 200 is safely and properly placed against the eyelid. For example, in some embodiments, the eye treatment device 200 includes a pupil alignment guide 242. The pupil alignment guide 242 may be, for example, a mirror with a circle, X, bull's-eye, or other target mark. In use, a patient may be able to properly position their eye by looking into the pupil alignment guide 242, observing the reflection of their pupil in the mirror, and aligning the pupil with the target mark. Additionally or alternatively, in some embodiments, the eye treatment device 200 includes a display 244, which may be a screen, a digital display, or other optical display. The display may present, for example, an image for the patient to stare at during use, a timer counting down the remaining treatment time, and/or reminder messages such as "Look Up" (explained below). The display 244 may also include a visualization means 160 for enhanced monitoring of eyelid margin during diagnosis and treatment.

The eye treatment device 200 of FIG. 8 may include any or all of the features described in relation to other embodiments presented herein. For example, in the depicted embodiment, the energy transducer module 120 is an infrared LED array. However, in other embodiments, including other embodiments configured to apply energy to one eyelid at a time, the energy transducer module 120 may include an LED emitting light in the visible light spectrum, a laser, an incandescent lamp, a xenon lamp, a halogen lamp, a luminescent lamp, a high-intensity discharge lamp, or a gas discharge lamp. The eye treatment device 200 may further include a scleral shield 300 made of an energy-absorbing material or have an energy-absorbing or energy transmission surface on a front face 302 for absorbing or transmitting heat and warming the inner surface of the eyelid during treatment. The scleral shield 300 may also incorporate one or more temperature sensors 310 in order to monitor the treatment session, ensuring that the inner surfaces of the eyelids reach a desired temperature and/or do not exceed a predetermined threshold. The scleral shield 300 may further include an image translator 155 integrated into the scleral shield, allowing viewing of the meibomian glands behind the eyelid. The eye treatment device 200 of FIG. 8 preferably also includes a power source module 110 and optionally a controller 212, along with other components as described in relation to various embodiments presented herein. Additionally, the eye treatment device 200 of FIG. 8 includes a reflector 210. In the depicted embodiment, the reflector 210 is formed of a barrel and backplate, which together surround the energy transducer module 120 in all but a distal direction.

The eye treatment device 200 of various embodiments also includes one or more thermal management structures configured to cool at least a portion of the device. In some embodiments, the thermal management structures are provided to manage the heat of the energy transducer module 120 and prevent the eye treatment device 200 from overheating. Additionally or alternatively, in some embodiments, the thermal management structures are provided to cool a surface of the eyelid to limit discomfort and avoid injury to the eyelid tissue during treatment. In FIG. 8, for example, the eye treatment device 200 includes a thermal management structure 220 (shown as a finned heat sink), a thermoelectric (Peltier) module 224, and one or more thermally conductive surfaces that are passively or actively cooled. In some embodiments, a passive heat sink may be provided as an adequate thermal management structure 220 to dissipate heat from the energy transducer module 120 into the surrounding environment without the need for a thermoelectric module 224. Some embodiments include a thermoelectric module 224 or other type of cooler (such as a compact vapor-compression cooler) designed to cool the energy transducer module 120 by transferring heat directionally away from the energy transmission surface 140. In FIG. 8, the thermoelectric module 224 and thermal management structure 220 are coupled such that the thermoelectric module 224 pumps heat away from the energy transducer module 120 towards thermal management structure 220 for dissipation. Additionally or alternatively, some embodiments include one or more thermally conductive surfaces. For example, in FIG. 8, the barrel and backplate of the reflector 210 are thermally conductive and coupled to both the energy transmission surface 140 and the thermoelectric module 224. Moreover, the energy transmission surface 140 is thermally conductive. As a result, heat from the surface of the eyelid and the energy transmission surface 140 can be pulled towards the thermoelectric module 224 to help maintain a comfortable temperature against the eyelid. Actively cooling the energy transmission surface 140 may occur not only during the heat treatment period, but before, after or intermittently, as a means of cooling the eyelids. Such a feature may not only provide relief from the burning and itching sensation that often accompanies MGD and blepharitis, but may also provide reduction of inflammation of the eyelids.

In some embodiments, the eye treatment device 200 includes a non-contact temperature sensor 232 to be used, for example, in conjunction with one or more thermal management structures. The non-contact temperature sensor 232 may be a remote reading IR thermometer or other suitable temperature sensor. The non-contact temperature sensor 232 can be focused on a region of the eye of particular interest. For example, in FIG. 8, the non-contact temperature sensor 232 is focused on a bottom edge of the cornea, and thus, provides a reading of the temperature at the cornea's edge. The non-contact temperature sensor 232 may be operatively coupled to a controller 212 such that, in some embodiments, the controller 212 modulates or shuts down the energy transducer module 120 or activates one or more thermal management structures in response to receiving an elevated temperature reading from the non-contact temperature sensor 232. In some embodiments, while heat is being applied to the lower eyelid (for example), the display 244 may instruct the patient to "Look Up" in order to allow the non-contact temperature sensor 232 to measure the temperature of the eye (sclera) at a location that is directly behind the portion of the eyelid being heated. In this manner, the eye treatment device 200 can continue to heat the eyelid while periodically ensuring that the eyeball is not being overheated. It will be appreciated that the device configuration shown in FIG. 8 may easily be adapted for treating the upper eyelid, for example by reversing the orientation of the energy delivery elements while keeping the display 244 and alignment elements in their upright (readable) orientation.

Figure 9:
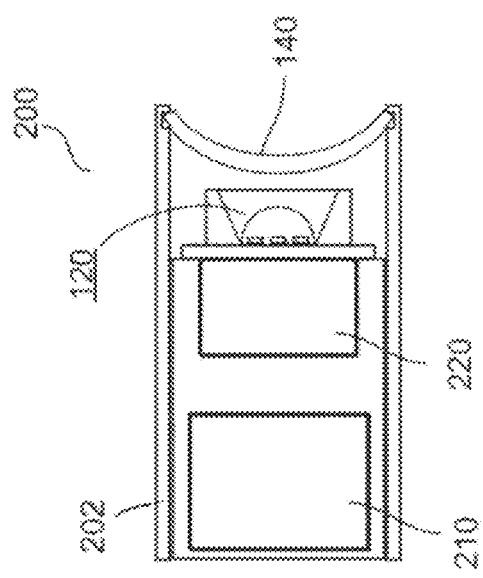
FIG. 9 is a schematic side plan view of another embodiment of an eye treatment device including one or more cooling mechanisms.

FIG. 9 depicts a side view of another embodiment of an eye treatment device 200 having one or more thermal management structures 220. Any of the thermal management structures 220 described with reference to FIG. 8 or 9 are suitable for use, and expressly contemplated for use, with any of the eye treatment device 200 embodiments described herein. The thermal management structure 220 may include any suitable structure configured to remove heat from the energy transducer module 120 so that the energy transducer module 120 remains within a desired temperature range to maintain efficiency of the energy transducer module 120. In some embodiments, the thermal management structure 220 is disposed at least partially within the housing 202 of the eye treatment device 200, along with the power source module 110 and other internal components. In some embodiments, one or more of the following thermal management structures 220 are provided within the housing 202: a heat sink (e.g., the finned heat sink embodiment of thermal management structure 220 shown in FIG. 8), a thermoelectric (Peltier) module (e.g., the thermoelectric module 224 of FIG. 8), a compact vapor-compression module, and a fan. In some embodiments, the thermal management structures 220 direct and distribute the heat in a manner that keeps the housing 202 cool to the touch.

Additionally, in some embodiments, the eye treatment device 200 includes a surface cooling system designed to prevent the eyelid surface from heating to the point of discomfort or injury while the target tissue below the surface is being heated. A surface cooling system is not needed in all embodiments; for example, in some embodiments, the selected energy transducer module 120 is configured to emit light energy at a wavelength that is absorbed into a target tissue region within the eyelid or an energy-absorbing portion of a scleral shield with minimal heating of an eyelid's surface tissue. In embodiments in which a surface cooling system is present, the surface cooling system may be configured to cool the surface of a patient's eyelid to or below body temperature or to a temperature below the target tissue temperature or below a threshold of discomfort before, during, or after delivery of energy to the target tissue region. The surface cooling system may include any suitable structure configured to cool a surface of the eyelid and/or cool the energy transmission surface 140. For example, in some embodiments, the surface cooling system includes an active cooling element, such as a fan. In some such embodiments, the energy transmission surface 140 is shaped such that an air gap exists between the energy transmission surface 140 and at least a portion of the eyelid. FIG. 2B depicts an embodiment appropriately structured for this purpose. In such embodiments, air may be blown within the air gap across the surface of the eyelid. In other embodiments, the energy transmission surface 140 may have one or more holes or channels extending through or along the energy transmission surface 140, through which air can be blown. In some embodiments, air is cooled before being blown across the surface of the eyelid. The air may be cooled, for example, using a thermoelectric cooler, compressor, ice, or other chilling element.

In other embodiments, an evaporative agent such as water or alcohol may be applied to the energy transmission surface 140, such that a surface of the eyelid then comes into contact with the evaporative agent. Additionally or alternatively, an evaporative agent may be applied to the surface of the eyelid before, during, or directly after treatment with the eye treatment device 200. As evaporation occurs on the surface of the eyelid as a consequence of the evaporative agent, a cooling and relieving sensation may be experienced by the patient. In still other embodiments, the eye treatment device 200 may include a cooling bladder positioned between the energy transmission surface 140 and the surface of the eyelid. The bladder may be filled with a cool water or gel and provide a cooling and relieving sensation to the patient when the bladder is in contact with the surface of the eyelid. As another non-limiting example, the surface cooling system may include the energy transmission surface 140 itself. In some such embodiments, the energy transmission surface 140 may be formed from an energy-absorbing material, such as, for example, diamond, sapphire, calcium fluoride, or graphene, and thermally linked to a larger thermal mass. Such large thermal masses take a long time to heat, and thus, may not heat up significantly during a treatment period. The large thermal mass may, therefore, sink heat away from the energy transmission surface 140 during a treatment period. In addition, the large thermal mass may be cooled prior to, or during, the treatment period, and may also be formed from the same materials, and as part of, the energy transmission surface 140, or it may be formed as a separate element out of materials such as copper, aluminum, or other energy-absorbing or conducting material.

Figure 10:
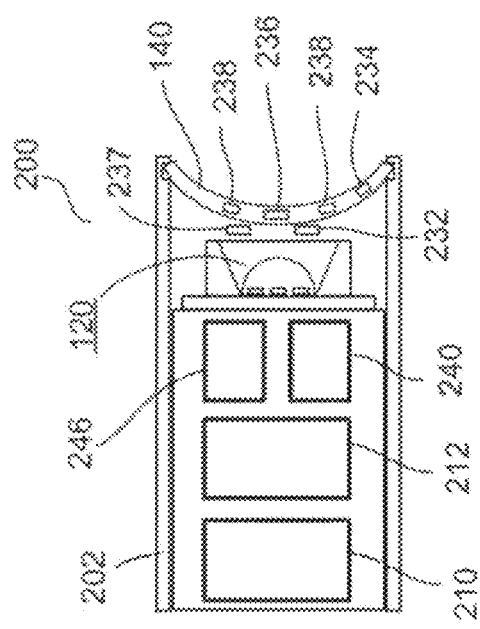
FIG. 10 is a schematic side plan view of another embodiment of an eye treatment device including one or more safety sensors.

In addition to the thermal management structures 220 and surface cooling systems described above, at least some eye treatment devices 200 include one or more safety sensors 230, for example, to monitor parameters of the eye treatment device 200 or to ensure patient safety. FIG. 10 provides one example of an eye treatment device 200 having one or more safety sensors 230. Any of the safety sensors 230 and related controllers 212 described with reference to FIG. 10 are expressly contemplated for use with any of the eye treatment device 200 embodiments described herein. Any particular eye treatment device 200 may include one or more types of safety sensors 230. A first set of safety sensors 230 provided in FIG. 10 are configured to sense temperature. Such safety sensors 230 include a non-contact temperature sensor 232 and a thermocouple or thermistor 234. The non-contact temperature sensor 232 may be a remote reading IR thermometer (such as a thermopile or pyroelectric or microbolometer) or other suitable non-contact sensor. The non-contact temperature sensor 232 may be designed to gather temperature data from the full field of illumination, such as during a treatment period, to monitor the surface temperature of one or more eyelids, or it may be designed to focus on a particular region and provide a temperature reading of that region. For example, the non-contact temperature sensor 232 may be positioned and configured to provide a temperature reading of a portion of the cornea, sclera, or other region of the eye, to ensure such tissue is not overheated and damaged, as is depicted in FIG. 8, for example.

Additionally or alternatively, some embodiments include a thermocouple or thermistor 234 (or RTD) positioned on or near the energy transducer module 120. Such a placement allows the thermocouple or thermistor 234 to detect the temperature of the energy transducer module 120 so that the temperature of the energy transducer module 120 can be monitored. If the energy transducer module 120 runs too hot, it can become inefficient and/or damaged. Additionally or alternatively, a thermocouple or thermistor 234 may be disposed on, within, or adjacent to the energy transmission surface 140. Such a placement allows the thermocouple or thermistor 234 to detect the temperature of the energy transmission surface 140 and/or the surface of an eyelid. Monitoring the temperature of such surfaces may help to ensure that a patient does not experience significant discomfort or injury from use of the eye treatment device 200. In certain embodiments, the various temperature sensors 232, 234 are operatively coupled to a controller 212, which may be programmed to modulate the output of the energy transducer module 120 or one or more thermal management structures or surface cooling systems, in order to bring or hold the temperature to within a predetermined target range. Also, if the temperature inputs from the temperature sensors 232, 234 are above the predetermined range, the controller 212 may turn off the output from the energy transducer module 120. Additionally or alternatively, temperature sensors 232, 234 may be coupled with the scleral shield 300 (not shown in this figure) to monitor the temperature of the inner surface of the eyelid and/or surface of the eye. Additionally, a pressure sensor or sensors 221 may be disposed on, within, or adjacent to the scleral shield 300 and/or the energy transmission surface 140 to monitor the pressure or force applied by the user on the eyelid.

A second set of safety sensors 230 present in FIG. 10 are provided to sense the position of the eye treatment device 200 relative to the eyelid of a patient. A light sensor 236 present in, on, or near the energy transmission surface 140 is configured to detect light. In various configurations of the eye treatment device 200, when the energy transmission surface 140 is properly placed adjacent to one or two eyelids, depending upon the configuration, it should significantly reduce the amount of ambient light that can reach the light sensor 236. In some embodiments, if light is detected in, on, or near the energy transmission surface 140 above a threshold range, it is an indication that the energy transmission surface 140 is not properly placed. Similarly, contact sensors 238 may be present in or on the energy transmission surface 140. Each contact sensor 238 may be configured to detect changes in capacitance, such as, for example, the change in capacitance that occurs when a contact sensor 238 is near human skin. Alternatively, contact sensors 238 may comprise electrodes that apply a small DC or AC microcurrent and which sense changes in impedance a result of contact with skin. Or, contact sensors 238 may comprise microswitches or force or pressure sensors, all of which produce a change in signal characteristics when energy transmission surface 140 is against skin. Thus, sensors 238 can be used to help determine the placement of the eye treatment device 200. If the eye treatment device 200 is properly placed against a closed eye, an upper contact sensor 238 and a lower contact sensor 238 should each come into contact with the skin of an eyelid and sense a change in capacitance (or impedance, switch status, force, pressure, etc.). In various embodiments, the light sensor 236 and/or contact sensors 238 are operatively coupled to a controller 212. In some such embodiments, the controller 212 is programmed to prevent activation of the energy transducer module 120 until the controller 212 detects, through signals from the sensors 236, 238 that the eye treatment device 200 is properly placed adjacent to a closed eye. Additionally, in some embodiments, the controller 212 is programmed to shut off the energy transducer module 120 if signals received from the sensors 236, 238 indicate that the eye treatment device 200 is no longer placed properly against a closed eye. Additionally, or alternatively, thermocouples or thermistors 234 on, in or adjacent to energy transmission surface may be used to indicate when the device is properly positioned adjacent to a patient's eye. For example, the thermocouples or thermistors 234 may register room temperature prior to placement of the device adjacent to the eye, and as the energy transmission surface 140 comes into contact with the eyelid skin (in embodiments where direct contact is desired), the thermocouples or thermistors 234 will register a value closer to body temperature, and therefore, confirm proper positioning. Further, if multiple thermocouples are used in embodiments which treat both the upper and lower eyelid, the data from the thermocouples or thermistors 234 may be used to determine if the eye is open or closed. A reflective or color sensor 237 may also be incorporated into the device in order to confirm that the eye is closed. Such a sensor 237 can either determine the color of a region of the optical field in front of the sensor 237, or it can determine the degree of reflection of the surface in front of the reflective or color sensor 237. In either case, the sensor 237 provides data indicating whether or not there is tissue that appears to be eyelid skin (e.g., flesh colored and not wet or shiny) or eye tissue (white or iris colored, and wet and shiny).

In some embodiments, contact sensor 238 comprises a microswitch embedded behind a flexible, sealed surface. In other embodiments, contact sensor 238 comprises a sensor which provides an indication of the amount of force or pressure applied by energy transmission surface 140 against the eyelid. Such an indication may be useful in order to avoid applying excessive force during a treatment, or to apply force within a certain range during initial diagnosis when the eyelid is meant to be slightly compressed to enable assessment of meibomian gland secretions. It will be appreciated that the force of the energy transmission surface 140 against the eyelid or eyelids applied by the clinician can be either regulated or not regulated. Further, the in-office device the force may be applied with a rolling or angular component to assist in moving the meibum out of the meibomian glands and ducts. In some embodiments, the energy transmission surface and/or scleral shield may have a curved or angular shape surfaces, or may have a rocking elements, such that when the energy transmission surface compresses the eyelid against the shield, there is initially more compression in the lower region of the meibomian glands that gradually transfer to the upper region as compression increases, moving meibum from the lower region to the upper region and then out of the meibomian gland ducts.

Figure 11A:
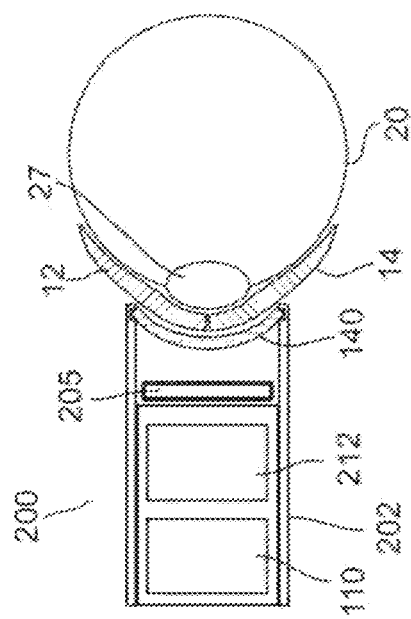
FIG. 11A is a schematic side plan view of another embodiment of an eye treatment device.
Figure 11B:
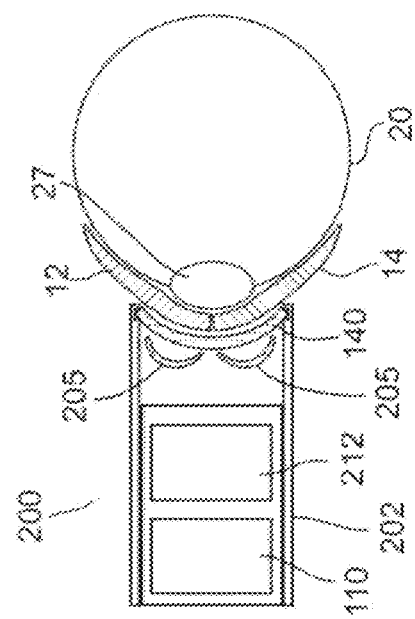
FIG. 11B is a schematic side plan view of another embodiment of an eye treatment device.

FIGS. 11A and 11B depict side views of additional embodiments of an eye treatment device 200 having energy transducer 205 configured to convert electrical energy from the power source module 110 into ultrasonic energy. The ultrasonic energy transducer 205 may be formed from any suitable material, such as a piezoelectric ceramic, polymer, or composite. In the various embodiments described above, an ultrasonic energy transducer 205 may be used in combination with the light energy transducer module 120.

In FIG. 11A, the eye treatment device 200 includes a flat piezo ultrasonic energy transducer 205 configured to emit unfocused ultrasound waves. While the direction of the waves is unfocused, the wavelength of the ultrasonic energy can still be manipulated so as to target particular regions of a tissue. With ultrasonic energy, the longer the wavelength, the deeper the penetration. Accordingly, in some embodiments, short, high-frequency waves of 20-100 MHz, 50-100 MHz, or any sub-range or individual value therebetween are emitted. Ultrasonic waves of such frequencies may penetrate the tissue of the eyelid 1-3 mm. Advantageously, at such penetration depths, the meibomian glands and other surrounding target tissue can be heated without significant heating within the eye. In other embodiments, a wavelength of greater than 100 MHz may be emitted from the ultrasonic energy transducer 205.

The eye treatment device 200 of FIG. 11B includes one or more curved piezo ultrasonic energy transducers 205 configured to produce focused ultrasound waves. In some embodiments, the ultrasound waves are directionally focused to selectively heat a target tissue region sufficiently to melt meibum within meibomian glands located within or adjacent to the target tissue region. In some such embodiments, the ultrasound waves are targeted and directed through the use of a shaped or curved transducer having a focal point. FIG. 11B depicts one such embodiment. In other embodiments, the ultrasound waves are targeted and directed using a shaped array of individual ultrasonic elements. There may be more than one array of ultrasonic elements; for example, one array may be directed at the lower eyelid, and another array may be directed at the upper eyelid. It will be appreciated that in order to efficiently transmit ultrasonic energy into the target tissue, the energy transmission surface 140 must be made from an appropriate material. For lower-frequency ultrasonic waves, traditional materials such as silicone or other polymers and elastomers may be utilized. In certain embodiments, it may be desirable to cool the surface of the eyelid as the ultrasonic energy is applied, to prevent exceeding a predetermined threshold. In such cases, the energy transmission surface 140 may be made from a material that not only can pass the ultrasonic energy, but which is also thermally conductive (so that the cooling techniques described previously herein may be applied). Examples of materials that can pass higher-frequency ultrasonic energy as well as provide adequate thermal conductivity include diamond or graphene.

It will be appreciated that, in addition to providing tissue heating effects, the ultrasonic waves may disturb, disrupt, or even kill the *Demodex* mites mentioned previously. As such, it may be beneficial to combine energy modalities such as light and ultrasound in order to achieve the best overall treatment for MGD, blepharitis and related maladies.

Figure 12:
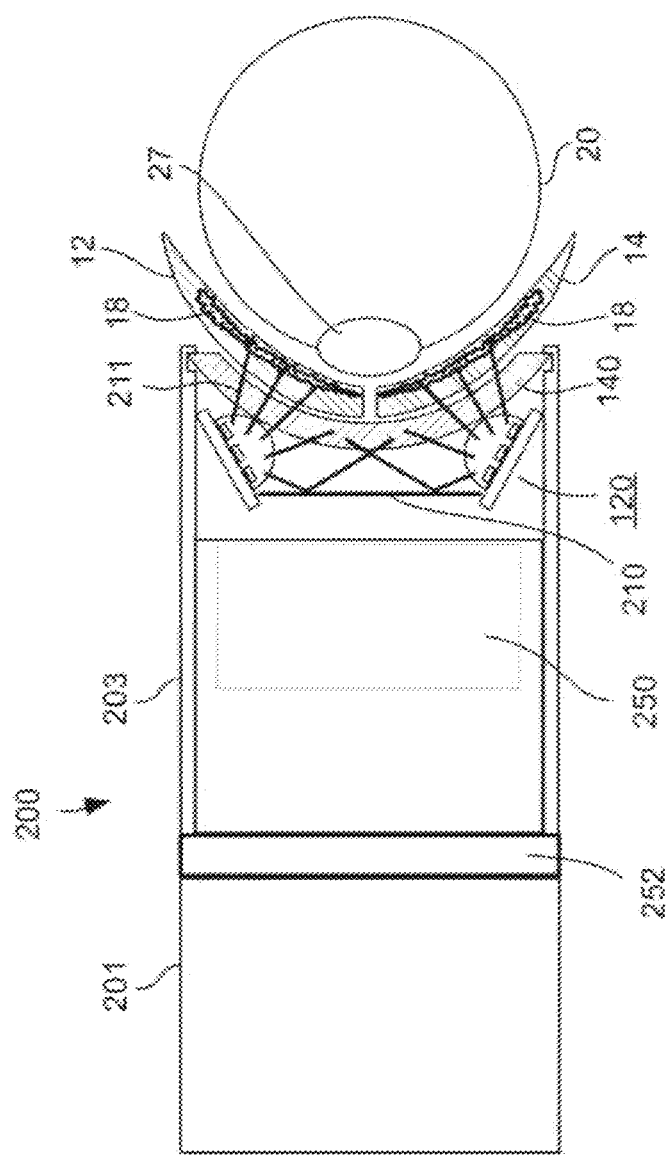
FIG. 12 is a schematic side plan view of another embodiment of an eye treatment device including vibrational means.

In addition to heating a target tissue region, the eye treatment device 200 of certain embodiments may also be configured to send vibrational energy into an area that includes the target tissue region. FIG. 12 provides one example of an eye treatment device 200 configured to produce vibrational energy. The vibratory mechanism 250 embodiments described in relation to FIG. 12 are expressly contemplated for use with any of the eye treatment device 200 embodiments described herein. The eye treatment device 200 of FIG. 12 includes a vibratory mechanism 250 within a portion of the housing 202. Any suitable vibratory mechanism 250 may be used. In various embodiments, the vibratory mechanism 250 is configured to generate a specific vibratory pattern. For example, when held against the eyelid of a patient, an eye treatment device 200 having a vibratory mechanism 250 may vibrate forward and backward along an axis parallel with the central ocular axis 30. In other embodiments, the eye treatment device 200 may vibrate side-to-side or up-and-down in directions orthogonal to the central ocular axis 30. In still other embodiments, the eye treatment device 200 may vibrate in a circular pattern, for example, a circular pattern orthogonal to the central ocular axis 30. In some embodiments, the eye treatment device 200 may include multiple settings such that a plurality of vibration patterns can be selected. The vibratory pattern may be applied to an eyelid before, during, or after the delivery of heat to the target tissue region.

In some embodiments, the frequency of vibration is between about 1 Hz and about 20 KHz, but may extend into the ultrasonic frequency range up to 20 MHz, and may include any sub-range or individual value therebetween. Vibrations within the frequency range may help aid in expressing meibum, which has thickened or is blocked within the meibomian glands. In addition, the vibration pattern may disturb or disrupt the *Demodex* mites, thereby reducing their proliferation. It will be appreciated that combinations of vibration and/or ultrasonic energy application may be employed to generate the most effective overall treatment including tissue and meibum heating, meibum vibration and expression, and mite disruption.

As further depicted in FIG. 12, in some embodiments, the vibratory mechanism 250 is positioned in a distal portion 203 of the housing 202. In some such embodiments, a vibratory isolation element 252 is positioned between the distal portion 203 of the housing 202 and a proximal portion 201 of the housing 202 such that the force of the vibrations is damped in the proximal portion 201. In some embodiments, a handle or hand gripping portion of the eye treatment device 200 is located in the proximal portion 201; thus, the vibratory isolation element 252 helps limit vibrations of a user's hand during use. In other embodiments, no isolation element 252 is present. In still other embodiments, the vibratory mechanism 250 is disposed within the proximal portion 201 of the housing 202, with a translational linkage between the vibratory mechanism 250 and the distal portion 203.

It should be emphasized that the foregoing specific embodiments are exemplary, and that this disclosure encompasses a large number of variants beyond those particular embodiments. Some of these will now be described in greater detail.

When the energy transducer module 120 is an LED emitter 207, some embodiments includes the use of one or more LEDs, preferably having high intensity. For example, one or more LEDs having a combined power output of at least 10 watts, preferably at least about 15 watts, or even 20 watts or more of combined power output. The combined intensity of those LEDs can advantageously be at least about 20, 30, 40, 50, 75, 100, 150, 200, 250, 300, 400, 500, 1000, 2000 or more lumens. When directed to the eyelid, the continuous intensity of the applied luminous energy can preferably be between about 0.02 and 2 Watts/square-centimeter.

In some embodiments, the LEDs can be green LEDs. Green is advantageous in that it penetrates and heats tissue to the depth of about 0.5-2 mm, beyond which it is significantly attenuated. This allows the light energy to penetrate to the treatment area encompassing tissue at or adjacent to the meibomian glands, with limited light transmitted to the eye. Some preferred wavelengths for the light can be 495-570 nm, 500-600 nm, and more preferably about 510-540 nm or 520-530 nm. In some embodiments, an infrared radiation source can be 700-1000 nm, preferably in the "optical window" of human tissue around 800-900 nm, and more preferably about 850 nm. Longer wavelengths would work also, potentially taking advantage of more absorption by water in tissue as the wavelength increases. For example, 3,000 nm infrared may be able to provide ideal heating of the eyelid tissue with minimal penetration and heating of the eyeball and sensitive structures. In other embodiments, the LEDs can be blue, yellow, red, white, or a combination of any of the foregoing.

The energy transducer module 120 can alternatively comprise a broad or narrow spectrum lamp, such as an incandescent lamp, a xenon lamp, halogen lamp, a cold cathode tube, a fluorescent tube, and the like. The illumination source may further comprise a spectral limiting element to reduce the intensity of or substantially eliminate certain undesired wavelengths from the spectrum of the lamp. Those spectral limiting elements can include colored filters, dichroic filters, IR cutoff filters, gratings, bandpass filters, spectral separating elements such as prisms or gratings, and the like. Infrared lamps or heating elements can also be used. The primary wavelengths allowed to reach the eyelid can be selected as discussed above for LEDs, or can be limited primarily to infrared radiation.

The energy emitted by the illumination source and delivered to the patient is preferably continuous in delivery (with pulse-width or other form of modulation, if desired), as opposed to low duty cycle, high-intensity pulsed light (such as IPL). The treatment period is preferably for multiple seconds or minutes, e.g., 5, 7, 10, 12, 15, 18, 20, 15, 30, 40, 45, 50, 60 seconds, or 1, 1.5, 2, 3, 4, 5, 6, 7, 8, 9, 10, 15, 20, or even 30 minutes or more.

In some embodiments, visible light delivery from the energy transducer module 120 can be facilitated by, or replaced with, an alternative energy transducer functioning as a heating modality. These can include, for example, an ultrasound transducer or a radio frequency emitter. When an ultrasound transducer is used, it can be either focused or unfocused. High frequencies are preferred, to limit the depth of heating, to concentrate heating on the target tissue area comprising or adjacent to the meibomian gland, and to reduce or eliminate effects on the eyeball or other tissue in the region. Preferred frequencies are 50-100 MHz or greater than 100 MHz to 250 MHz. Focused ultrasound, for example, using multiple transducers, including phase-managed arrays to facilitate directional focus, or shaped transducers having a limited focal area, are particularly preferred. As with the light energy, relatively continuous delivery can be used, as can pulsed delivery.

When a radio frequency emitter is used, frequencies known to provide localized heating are preferred. Frequencies used for electrosurgery, such as 300 KHz-4 MHz can be advantageously used. In one such embodiment, bipolar electrodes are provided in or on the energy transmission surface 140 to contact the eyelid and permit control of location and depth of heating.

Alternatively, higher frequency radio waves, in the 5 MHz to 10 MHz range, can be used due to their higher attenuation rate in tissue, thus allowing careful selection of penetration depth and limitation of heating to the desired region of tissue. For example, frequencies above about 245 MHz penetrate human skin and tissue to a depth of about 1-3 mm, which matches the typical distance between the exterior of the eyelid and the target tissue (i.e., the meibomian glands and adjacent tissue).

The energy waveguide module 130 is designed to transmit energy from a transducer or generator to the energy transmission surface 140 and thence into the target tissue. For example, when creating light energy from a small source such as a LED or small lamp, the energy waveguide module 130 can direct even illumination from the source to the target tissue zones. In some embodiments, it may be desirable to include a waveguide structure to direct light toward the eyelid and the target tissue without directing it along the central ocular axis of the eye. This can then reduce the amount of light penetrating into the cornea and into the eye, while still directing the light to the eyelid, albeit at a more tangential angle. Suitable structures for accomplishing this purpose include light pipe arrays, refractive elements, reflective elements, diffractive elements, total internal reflection elements (TIRs), and diffusers. For example, fiber optics, mirrors, lenses, prisms, and the like can be used to direct light and change its angle of incidence onto a target surface (to avoid central ocular axis, for example). In some embodiments, it may be desirable to direct light toward the scleral shield 300 and image translator 155 to view the inner side of the eyelid 14 and/or heat the meibomian glands behind the eyelid, as described above.

In another embodiment, the energy waveguide module 130 is an ultrasonic waveguide having surfaces that reflect ultrasonic energy to direct and/or focus it onto a desired region, e.g., the target tissue region. Similarly, a microwave or other RF waveguide of known design can be used to direct RF energy to the desired region.

The energy transmission surface 140 is interposed between the interior of the eye treatment device 200 and the patient, providing a barrier therebetween. It can be envisioned in some embodiments as a window through which the energy is delivered to the patient. It can be configured to directly contact the eyelid of the patient, or to be spaced a small distance from the eyelid, such as between 0.5 mm and 12 mm from the eyelid during treatment. Preferably, the exterior surface of the energy transmission surface is smooth and easily cleaned. In some embodiments, a single-use outer eyelid pad 147 may be placed over energy transmission surface 140 in order to prevent cross-contamination between patients. The outer eyelid pad 147 may be fabricated from any suitable material such as glass, pyrex, quartz, mica, or polymers such as polycarbonate or other optically transparent materials can be used, or a combination thereof, in order to obtain the desired structural and optical properties. In some embodiments, the energy transmission surface 140 may be in a slidable relationship along movement path 145 with respect to either the energy transducer module 120 or scleral shield 300 or housing 202, so as to ensure energy transmission surface 140 can be pressed up against the eyelid or eyelids to: a) minimize photonic energy leakage during treatment and imaging, and b) if desired, apply a compressive force to the eyelid during evaluation or expression of meibomian glands.

When using light energy to heat the target tissue region, the energy transmission surface 140 is advantageously transparent to visible or infrared light as desired. In some embodiments, it is transparent to the peak or desired wavelengths used for treatment, such as visible light or green light, but blocks infrared light, thus reducing IR heating of the eyelid. Glass, pyrex, quartz, mica, or polymers such as polycarbonate or other optically transparent materials can be used.

When heating the target tissue region with ultrasound or RF, transparency to visible light is not necessary; instead, an ultrasound-transparent or RF-transparent material can be used. In some embodiments, it is desirable that the materials be thermally conductive, to facilitate cooling of the eyelid by cooling the energy transmission surface 140. Diamond, sapphire, and graphene are suitable thermally-conductive materials. In another embodiment, either the entire energy transmission surface 140 or at least a window thereof is transparent to safety sensors disclosed herein. For example, where a non-contact infrared temperature sensor is used to sense the temperature of the exterior of the eyelid, an IR-transmissive material is advantageously used for all or at least the relevant region or regions of the energy transmission surface 140.

When applying heating energy to the eyelid from the eye treatment device 200, some embodiments includes surface-cooling the eyelid by cooling the energy transmission surface 140. If the exterior of the eyelid is cooled while irradiating the target tissue region with light, ultrasound, or RF energy, patient comfort can be enhanced while maximizing efficacy through optimal heating of the target tissue. The energy transmission surface 140 can be cooled by: airflow across the interior of the energy transmission surface 140; application of an evaporative agent to the inside of the energy transmission surface 140, such as a refrigerant or water; circulating a cooling fluid through channels in or on the energy transmission surface 140; or contacting the energy transmission surface with a thermoelectric (Peltier junction) or a heat sink linked to a cooling modality. Alternatively, the energy transmission surface 140 can have a sufficiently large thermal mass (or be in contact with such a thermal mass) so as to remove sufficient heat from the eyelid during the treatment of the patient to maintain the eyelid within a desired temperature range. The thermal mass can be pre-cooled or simply begin at ambient temperature before the treatment. Other methods of cooling the energy transmission surface 140 and/or the eyelid include incorporating a reservoir between the energy transmission surface and the skin of the eyelid, such as a water-filled bladder. The bladder can be pre-cooled or actively cooled during the procedure, such as by circulation of cool water therethrough or through using a chilling element such as a thermoelectric device, a compressor, a refrigerant, or other chilling element.

In another embodiment, the energy transmission surface 140 is spaced a small distance from the eyelid to allow passage of a cooling fluid, such as relatively cool air, mist, water, and the like between the energy transmission surface 140 and the eyelid. For example, cool air can be induced to flow transversely across the surface of the eyelid and the energy transmission surface 140, or the energy transmission surface 140 can include holes or channels to direct the cooling fluid onto the eyelid. The cooling fluid can be ambient temperature or can be pre-cooled, such as through refrigeration, ice, and the like.

When a vibratory mechanism 250 is used, it can comprise, for example, a reciprocating element such as an electromechanical solenoid or the like, a rotating eccentric weight, such as an eccentric weight coupled to a motor shaft, or a rotating cam. Preferably, the vibratory mechanism is vibrationally coupled to the eyelid but vibrationally isolated from other patient or clinician contact points, such as the proximal end of the eye treatment device 200, including any handle region that a patient or clinician might hold.

Patient safety and comfort are important considerations in the present device and method. Safety sensors and warnings can thus advantageously be incorporated into the device. These include sensors for preventing overheating of the skin, sensors for preventing undesired activation of the device, and sensors monitoring the delivery of energy to the patient. In some embodiments, a safety sensor may be utilized to make sure that a consumable portion 260 having a protective scleral shield 300 is in the correct position prior to turning on an energy transducer module 120, thus preventing damage to the eye system 10.

As illustrated in FIG. 10, a safety warning apparatus 240 can be incorporated into the device to let the patient know of an unsafe condition, as sensed by any of the sensors described herein. This can include a flashing light, a flashing warning, a sound warning beep, a picture, a vibration pattern, or words indicative of the potential for or existence of an unsafe condition.

Again with reference to FIG. 10, a first set of safety sensors 232, 234, is preferably located on, in, in back of, or otherwise in the vicinity of the energy transmission surface 140. Both sensors are configured to detect heating of the outer eyelid surface and to prevent overheating thereof. Sensor 232 is preferably a non-contact sensor such as a pyroelectric sensor (for example, IRA-E700ST0 from Murata) or a thermopile (such as ST25T0-18 from Dexter Research, Dexter, Mich.) or a conventional temperature monitoring device such as a thermocouple, a thermistor, a fiberoptic thermal sensor, or a digital temperature sensor (such as a Dallas Semiconductor DS-18620). In addition to temperature sensors 232 and 234, temperature sensors 310 may be mounted on the front or back surfaces of scleral shield 300, as shown in FIGS. 3, 7A-H and 8, to monitor the inner eyelid surface temperature and eyeball temperature, respectively. A threshold temperature may be programmed into the eye treatment device 200, such as 40° C., 45° C. or 50° C. In some embodiments, when the threshold temperature is reached or exceeded, the safety sensor may be configured to shut off the eye treatment device 200 and/or via safety warning apparatus 240 to signal the user or clinician to stop treatment using lights, beeps or other notification means. In some embodiments, when the threshold temperature at any particular location is reached or exceeded, the controller 212 (or discrete circuitry independent of any controller) may be used to prevent heating of the eyelid beyond this threshold temperature. This can be accomplished, for example, by shutting off the eye treatment device 200, by reducing the energy being delivered (such as reducing intensity of the light, pulse-width modulation of the LEDs, reducing power input for ultrasound or RF energy, etc.), or by activating cooling measures to reduce eyelid temperature.

A second type of safety sensor is also illustrated in FIG. 10. This may include a single sensor or a plurality of sensors. The purpose of the second type of safety sensor is to ensure that the eye treatment device 200 is properly positioned against the eyelid prior to activation of the treatment. The second type of safety sensor can include one or more of the following sensors. One sensor can be a light sensor 236. When the device is positioned against the eyelid, ambient light is blocked. Thus, the absence of such light can be detected. Alternatively, a reflective optocoupler-type device can be used in which a light source is directed distally and is coupled with a sensor also aimed distally. This allows the presence of the patient to be detected, together with an approximation of the distance to the patient. Depending on the distance between the light source and the optocoupler-type device, light detection is either maximized or eliminated when the eye treatment device 200 is properly positioned. Another light-detection scheme is to provide a light sensor 236 facing distally toward the patient but outside of the path of the treatment light. When the eye treatment device 200 is spaced from the eyelid, reflected treatment light can reach the sensor 236, but when properly positioned, most such light is blocked from the sensor 236. The light sensor approach can be coupled with data from one of the temperature sensors to simultaneously detect light and skin temperature as an indication of the positioning of the device. In any of the light detection embodiments, an ambient light sensor 236 can be incorporated into the eye treatment device 200 to measure ambient light levels to facilitate the optical detection of proximity to the eyelid. Similarly, when using a temperature sensor in conjunction with the second type of sensor, an ambient light sensor 236 can facilitate determining when the eye treatment device 200 is against the skin, particularly in a high temperature environment. Other distance or contact detection elements, such as an ultrasonic range-finding module, can also be used. In some embodiments, thermocouples or thermistors 234 on, in or adjacent to the energy transmission surface may be used to indicate when the device is properly positioned adjacent to a patient's eye. For example, the thermocouples or thermistors 234 may register room temperature prior to placement of the device adjacent to the eye, and as the energy transmission surface 140 comes in proximity to the eyelid skin, the thermocouples or thermistors 234 will register a value closer to body temperature, and therefore, confirm proper positioning. A reflective or color sensor 237 may also be incorporated into the device to confirm that the eye is closed. As described above, such sensors 237 can provide data indicating whether or not there is tissue that appears to be eyelid skin (e.g., flesh colored and not wet or shiny) or eye tissue (white or iris colored, and wet and shiny).

In another embodiment, the second type of sensor can be a touch sensor, detecting when the eye treatment device 200 is touching the face. The touch sensor can be a resistive sensor, utilizing two electrodes and sensing a microcurrent through the skin, or a conventional resistive touch sensor. Alternatively, a capacitive sensor can be used to detect when the eye treatment device 200 is touching the skin. This can be either a single sensor or, for a better signal, a plurality of sensors wherein all or a subset of them must be activated to allow the treatment to proceed. Finally, the touch sensor can comprise an electrical switch (such as a microswitch) or a strain gauge that is activated when the device is pressed against the skin. For example, the microswitch can be embedded behind a flexible, sealed surface, or it can be activated when sufficient pressure is applied to allow a first part of the eye treatment device 200 to move with respect to a second part of the eye treatment device 200.

A third type of safety sensor may also be used in the eye treatment device 200 to monitor the energy delivery transducers to assure proper operation within predetermined parameters. Again, this may be a single sensor or combination of sensors, including one or more of the following. In some embodiments, the safety sensor can measure current and/or voltage applied to a transducer, as shown in FIG. 10 as transducer monitor 246. Thus, when the transducer is one or more LED emitter 207, the drive current or forward voltage of the LEDs can be monitored, where deviation from pre-established parameters can indicate failure of an LED or LED driver or unsafe operating conditions. The voltage across an RF or ultrasound transducer can similarly be monitored by transducer monitor 246, as can the current supplied thereto. In another embodiment, a thermal sensor such as thermocouple or thermistor 234 shown adjacent to energy transducer module 120 in FIG. 10 may be configured to monitor the internal or external temperature of a transducer element, wherein overheating can indicate unsafe operation or failure of an element, and lack of heating may also be indicative of an operational failure.

In some embodiments, the controller 212 may be a manual, or open-loop system, with autonomous discrete analog and digital circuitry for manual operation without any automatic control. The manual operation may include turning the eye treatment device 200 on and off, and receiving safety and feedback information. In this case, the eye treatment device 200 is operated manually without a controller by the user or clinician turning the eye treatment device 200 on and assessing desired treatment of the eyelid using the feedback and adjusting the process in response to the assessment. The feedback features may signal the user or clinician of the status, such as on/off, lights or beeps, temperature data, pressure data, safety data, or other data that could help the user or clinician assess the process. In some embodiments, the controller 212 may include direct-acting threshold detectors and shut-off circuits for safety. In some embodiments, the controller 212 may include a processor or centralized controller configured to monitor the process with feedback features and some portion of the feedback is returned to the controller for safety, such as turning the system off in an unsafe condition.

The controller 212 functional block encompasses and performs both operational functions, to direct the intended operation, and safety functions, and to interface with the various safety sensors 230. It can be a single processor controlling all functions, i.e., one controller 212 as illustrated in FIGS. 3 and 4A, or can comprise two or more controllers, such as a primary controller with a secondary safety controller acting as a watchdog on the first controller, as is well-known to those skilled in the art. Specifically, the secondary safety controller may be designed to monitor the functionality of the primary controller—if one or more parameters indicate the primary controller 212 may not be functioning properly, the secondary safety controller is configured to power down the energy transducer and/or the entire eye treatment device 200. The functions associated with controller 212 can be accomplished with a controller such as a microprocessor or microcontroller with associated software, but certain embodiments may preferably operate without a controller, and instead utilize one or more of a programmable gate array, a logic array, analog circuitry, digital circuit elements, or any combination of the foregoing.

In one simple embodiment, the secondary safety controller comprises an array of analog or digital circuit elements without a processor. For example, optical, temperature, and/or pressure switches either hard wired together or with logic circuitry, op amps, and/or relays are configured to allow initial or continued operation of the device only if the sensors are in a predetermined state. In an alternative embodiment illustrating full processor control, all sensors are monitored through digital or ADC inputs to one or more programmed processors to perform the functions of a second safety controller and to either prevent operation outside of predetermined parameters or to modulate the operation of active elements in the eye treatment device 200 to stay within those parameters.

In addition to safety functions, the controller 212 may direct the normal operation of the eye treatment device 200. For example, it can interface with the user through a user interface 270 which may include control buttons, rotary encoders, touch screens, voice commands, or any other conventional user interface. It can control a power manager, direct or interrupt current flow to the energy transducer and modulate its output, initiate or stop operation of the vibration apparatus, initiate or disable a safety warning, initiate, modulate, or stop operation of the surface cooling apparatus, and monitor and modulate cooling of the energy transducer through the thermal manager. The controller 212, or the discrete circuit substitute, may be operationally linked to some or all of these systems within the eye treatment device 200. In addition, it can include a timer function to automatically shut off the energy transducer and thus interrupt delivery of heating or vibrational energy to the eyelid after a predetermined period of operation, or in response to signals from the first, second, or third type of safety sensors.

The power source module 110 is designed to facilitate supply of power to the eye treatment device 200. It can include external power interfaces, such as cords or cables interconnecting with an external power source. In a preferred embodiment, the power manager includes an internal power supply. In some embodiments, the power manager includes a rechargeable battery or battery pack. This could include nickel-metal hydride batteries, lithium ion or lithium polymer batteries, nickel cadmium batteries, or any other suitable rechargeable or non-rechargeable batteries. The batteries preferably provide a high current capacity, such as 1-5 amps, preferably at least 3 amps surge current, with the ability to deliver such high current for 1, 2, 3, 4, 5, or more minutes. In some embodiments, the internal batteries deliver 3, 4, 5, 6, 7, 8, 9, 10, or 12 volts or more. The capacity of the batteries is dictated by the design load, and may be, for example, a battery pack having at least a 200, 300, 400, 500, 1000, 2000, 2500 mA-hour capacity or more. The desired voltage can be accomplished by connecting lower voltage batteries in series to achieve the desired voltage, or through use of a DC:DC converter to step up a lower voltage to the desired voltage. In some embodiments, the batteries supply a voltage lower than that required by the energy transducer power supply, and the voltage is stepped up for the energy transducer while a lower voltage, e.g., 5V or 3.3V, is supplied to the controller 212 or alternative discrete circuitry.

In one preferred embodiment, the energy transducer may be a high-power LED similar to one made by LED Engin, Inc.; specifically, the energy transducer may be an LZ9 configured with nine green emitters in a non-standard configuration arranged as three sets of three series emitters in parallel, requiring approximately 12-14V forward voltage and up to 2.4 amps for maximum illumination. In this embodiment, three RCR123 LiFePO4 cells or similar may be utilized in series, having a capacity of 750 mA-hours and providing a starting voltage of 7.2V. A DC-DC converter circuit is included which boosts the voltage by approximately two times in order to provide the voltage needed to drive the LED.

Power management functions can include a charger, battery status monitor, and/or temperature monitor. These functions can be performed by separate circuitry or incorporated in whole or in part into the controller 212. In some embodiments, power management includes a battery charger powered through inductive coupling to an external power supply, which can allow the eye treatment device 200 to be sealed, allowing easy cleaning and preventing ingress of moisture or dirt. In some embodiments, the inductive coupling may use a recharging cradle or electrically-isolated mains power connection. The inductive coupling may include two induction coils in close proximity (one in the cradle and one in the device) or two coils tuned to resonate at the same frequency (resonant inductive coupling or electrodynamic induction).

Thermal management is also a critical element of many preferred embodiments, including, in some cases, heat removal from the energy transducer, such as an LED or LED array. In the case of LEDs, it is important to maintain the junction temperature below a predetermined threshold, such as 135 degrees Celsius. Other transducers similarly have maximum allowable component temperatures, and proper thermal management helps maintain those components within allowable temperatures. For example, heat sinks thermally coupled to the energy transducer elements, fans, radiators, cooling fluids, and the like may be utilized. In a preferred embodiment, the eye treatment device 200 is sealed and a thermal management structure 220 such as shown in FIG. 9 directs excess heat to an external surface of the eye treatment device 200. This allows for a sealed device without ventilation openings. In other embodiments, a cooling fluid is directed from the thermal manager inside the device to remove heat from the device, such as through forced air cooling (as shown or FIG. 8), or a liquid-cooled radiator.

In a further aspect of the technology, the eye treatment device 200 may include elements useful in calibrating the device so that it provides the desired amount of heating to target tissue over a wide range of eyelid thicknesses. This is important because without such calibration, the amount of heating that occurs at the target tissue region (e.g., the meibomian glands and adjacent tissue) can vary unless the temperature near the target tissue region is measured during the treatment. As discussed previously, monitoring of the target tissue region may be accomplished by use of a scleral shield, or the like, equipped with temperature sensors. However, it may be inconvenient for users of the device to insert scleral shields each time they use the device. Therefore, it may be useful to calibrate each device to an individual's specific anatomy. To accomplish that, the device may be calibrated by using a scleral shield initially, preferably in the setting of an eye care professional's office, and in conjunction with an external monitor and calibrator.

Figure 13:
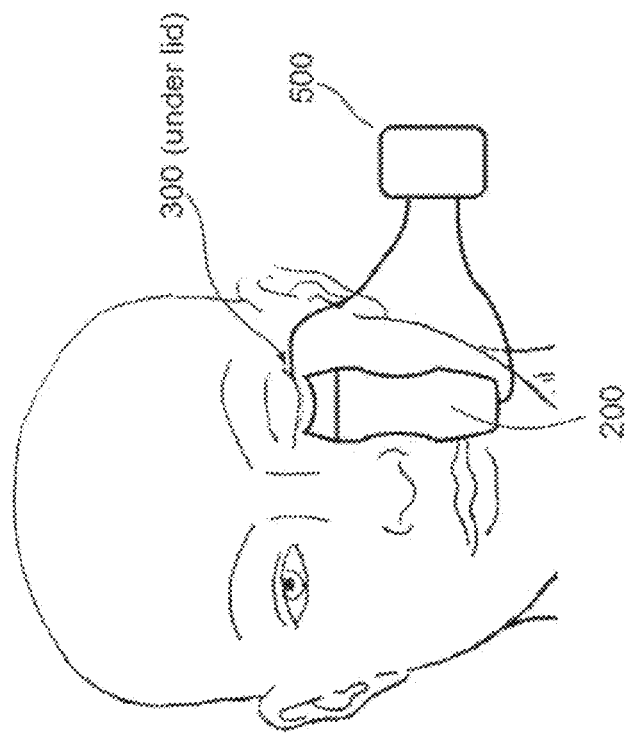
FIG. 13 is a schematic diagram of one embodiment of an eye treatment system in use by an individual.

For example, with reference to FIG. 13, as the eye treatment device 200 applies energy to the eyelid(s), the scleral shield 300 transmits temperature data (either through a wired or wireless connection) to an external monitor and calibrator 500. The external monitor and calibrator 500 tracks the rate of temperature rise over time, and thereby characterizes the heating profile of the patient's eyelid(s). With that data, the external monitor and calibrator 500 can then program the eye treatment device 200 to heat the target tissue to the desired temperature range. In a simple embodiment, the external monitor and calibrator 500 turns on the energy transducer, measures the amount of time needed for the target tissue to reach the desired temperature, and then turns off the energy transducer and programs the eye treatment device 200 to apply energy for that same amount of time. Alternatively, the eye treatment device 200 may be programmed to provide increased or decreased amounts of energy in order to heat the target tissue to the desired temperature within a preferred period of time. In most individuals, eyelid thickness is similar from upper eyelid to lower eyelid and from the right eye to the left eye, however, it will be appreciated that the external monitor and calibrator may separately measure and separately program the device to apply specific amounts of energy to each individual eyelid in order to ensure proper heating of each one. It will be further appreciated that there may be variances in the performance of the components used to implement the energy transducer and related circuitry, and that, without proper calibration, one device might produce more or less energy than another. One solution to this is for the factory to measure the actual energy output for a given command level from the controller, and to incorporate a calibration table within the controller, such that every eye treatment device 200 puts out an equal amount of energy for a given command level. Alternatively, and additionally, with the external monitor and calibrator 500, such variances can also be compensated for by the procedure described above, wherein the ultimate goal of the eye treatment device 200 is to heat target tissue to a desired temperature, and each eye treatment device 200 is programmed to do so (regardless of component variances) on each specific patient (and optionally on each specific eyelid).

Figure 14B:
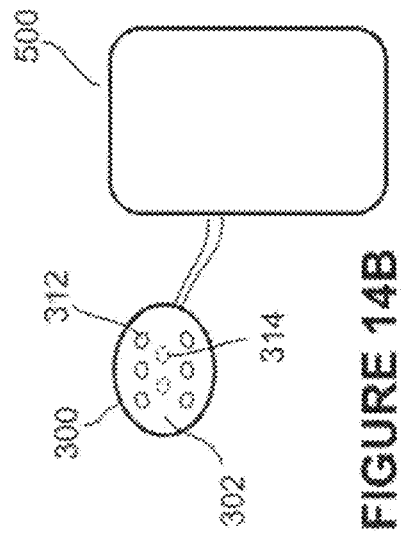
FIG. 14B is a schematic front plan view of a portion of the eye treatment system embodiment of FIG. 14A.
Figure 14A:
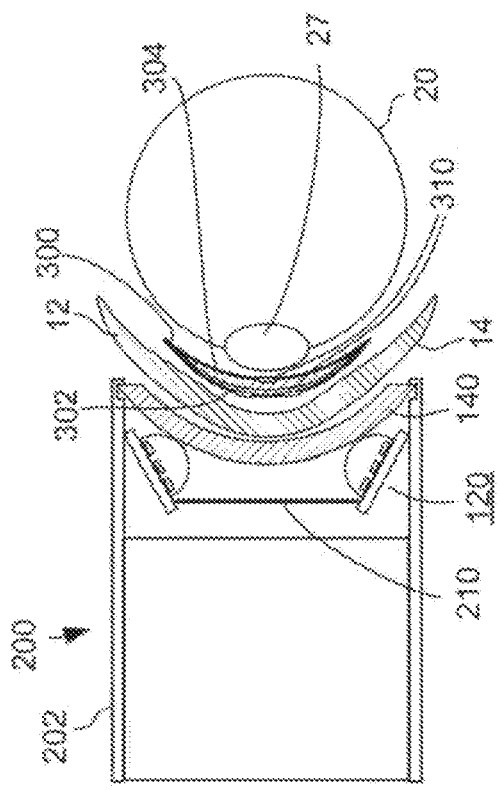
FIG. 14A is a schematic side plan view of an embodiment of an eye treatment system.
Figure 15A:
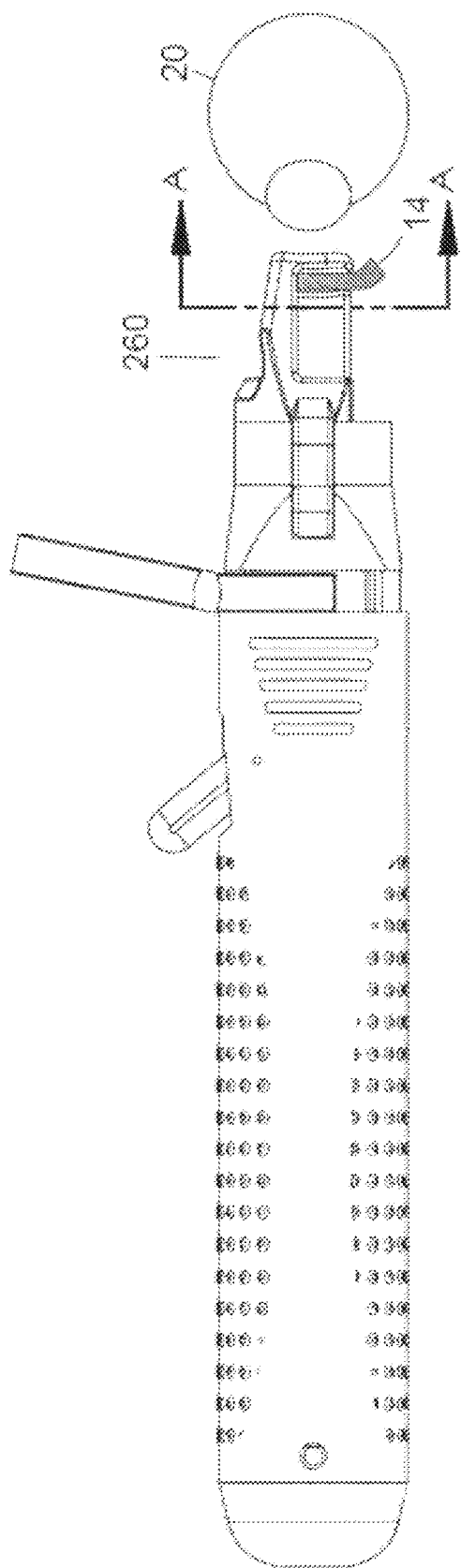
FIG. 15A is a schematic side view of an embodiment of an eye treatment instrument system.
Figure 15B:
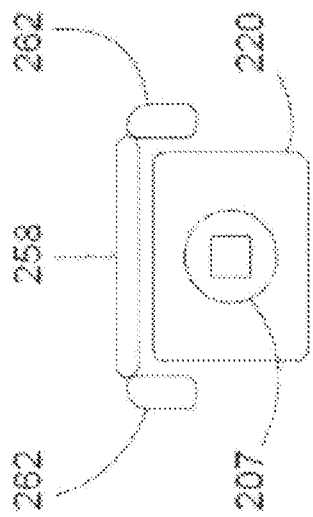
FIG. 15B is a front sectional view taken along A-A of the embodiment shown in FIG. 15A.
Figure 15C:
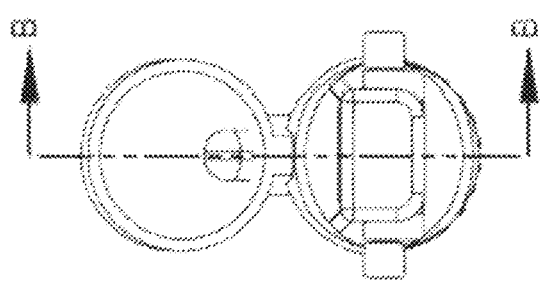
FIG. 15C is a front view of the embodiment shown in FIG. 15A.
Figure 15D:
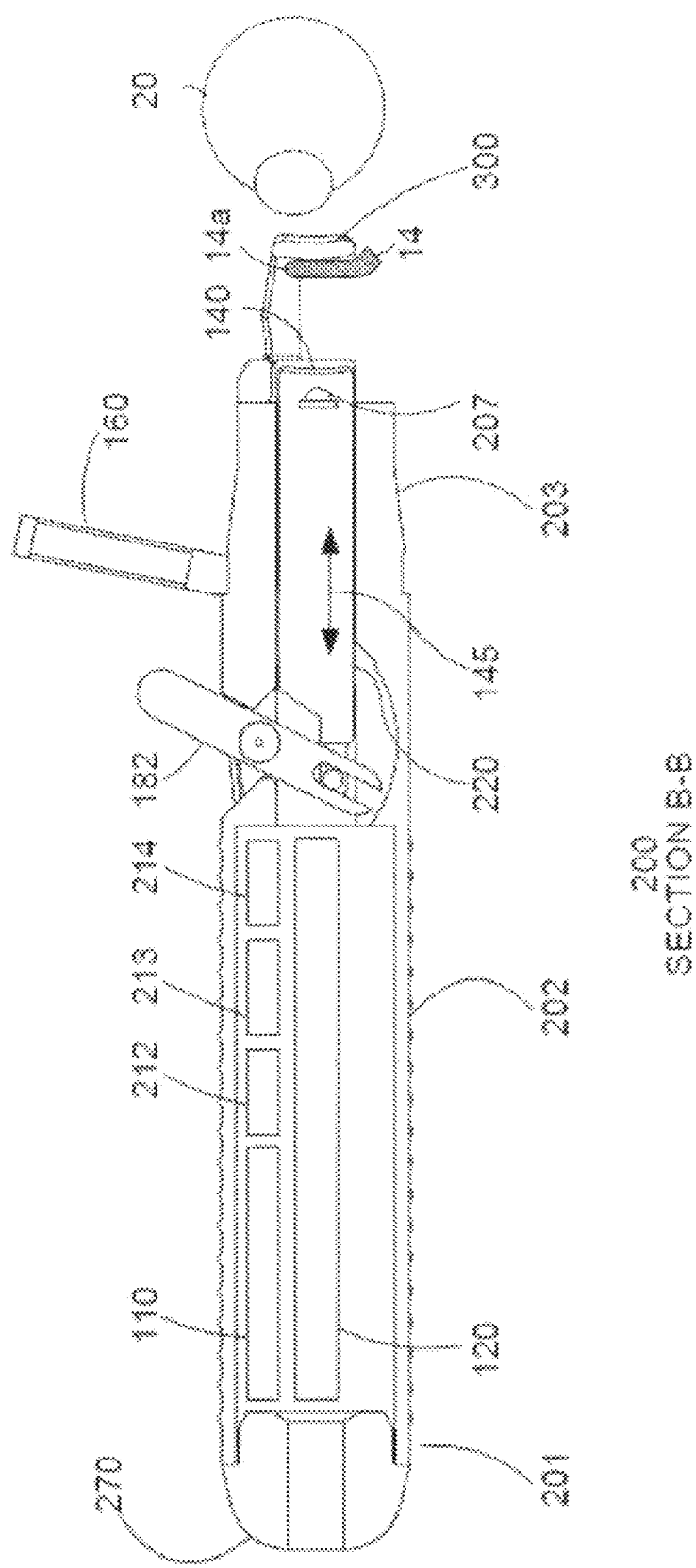
FIG. 15D is a side sectional view taken along B-B of the embodiment of FIG. 15A.

Referring now to FIGS. 14A and 14B, in one embodiment of the scleral shield 300, there is an array of temperature transducers 310 embedded in the shield. For this application, where the shield is not actually being used to shield the eye from the energy, but instead to measure temperatures, the shield 300 may be made of materials that are substantially transparent to the energy emitted from the energy transducer. By way of specific example, if the energy transducer is a light source, the shield 300 may be made of a clear material that passes the wavelength(s) of light emitted by the energy transducer. Preferably, the shield 300 is also as thin as possible and supple, with no sharp features, so that it can comfortably be placed under the eyelids with minimal discomfort to the patient and so it has a minimal effect on the heating of the tissue. In the embodiments shown in FIGS. 14A and 14B, an example is shown wherein there is an array of six temperature sensors 310 on a front face 302 of the shield 300, and an array of sensors on the back face 304. This configuration allows the front-facing sensors 312 to more directly measure the temperature of the tissue on the inside surface of the eyelids, where the meibomian glands are located, while the back-facing sensors 314 more directly measure the temperature of the surface of the eye, along the midline of the central ocular axis, where the most sensitive eye tissues are nominally located. The temperature sensors may be discrete elements (such as thermocouples made from very fine wire, or miniature thermistors) embedded in the shield 300, or they may be thermocouples formed by depositing thin films of appropriate metals onto intermediate layers of the shield 300. In some embodiments, the preferred types of materials for the shield 300 are soft, flexible, biocompatible materials such as silicone, polyurethane, and various hydrogels similar to those used in contact lenses.

While the above embodiments describe the configuration having and external monitor and calibrator 500, it will be appreciated that the eye treatment device 200 itself can have the same capability built into it, in which case the scleral shield 300 communicates temperature data directly to the eye treatment device 200, and the eye treatment device 200 programs itself to provide the correct treatment profile for that particular patient (and optionally for individual eyes and eyelids). In such embodiments, the eye treatment device 200 has a sophisticated user interface 270 allowing the clinician to command the eye treatment device 200 to perform a calibration sequence, and optionally instruct the eye treatment device 200 as to which eye and/or eyelid is being calibrated. It is appreciated that if the eye treatment device 200 is calibrated to provide individually calibrated treatment to each eye or eyelid, the eye treatment device 200 needs to be able to indicate (via a series of lights or an alphanumeric or graphical display) to the patient which eye or eyelid is to be treated next.

Alternatively or additionally, a calibration element may be used to measure the energy output of the eye treatment device 200. For embodiments where the energy transducer is a light source, the calibration element may be a light meter to measure, for example, luminous flux, lumens or radiant flux. For embodiments where the energy source is an ultrasonic transducer, the calibration element may be an ultrasonic energy meter. The calibration element may be used to determine if the eye treatment device 200 is operating within acceptable limits or not, and may also provide data to allow adjustment of certain parameters (such as energy level or treatment time) to bring the eye treatment device 200 back into the desired performance range. It will be appreciated that the calibration element may also communicate directly with the eye treatment device 200 or indirectly (e.g., through a PC) with the eye treatment device 200 in order to reprogram the eye treatment device 200 with updated calibration data to keep the device operating within an acceptable performance range.

In some embodiments, the eye treatment device 200 may further include a temperature display feature or dashboard 218 for the in-office device, which could include inner lid and outer lid temperatures. The temperature display feature may display absolute temperatures, or just relative temperatures versus a maximum. For example, the temperatures may be displayed in a bar graph format or with one or more lights.

In some embodiments, the eye treatment device 200 may further include a datalogger 214 configured to record aspects of the treatment, (e.g., time, date, usage parameters, temps, photos, videos, etc.). In some embodiments, the eye treatment device 200 may further include a voice recorder 213 so clinicians can record verbal observations of how many MGs are healthy, clogged, atrophied, etc., along with time, date and patient name. This allows the clinician to carry out the procedure without the need to take manual notes and/or without the need to have an assistant present. In some embodiments, the eye treatment device 200 may further include a communication means configured to couple with an external PC, tablet or smartphone for downloading data, voice recordings, camera images or video clips.

FIGS. 15A-15D show another embodiment of an eye treatment device 200 positioned relative to an eyeball 20 for treatment of the eyelid 14 for MGD, blepharitis and other medical conditions. In some embodiments, the eye treatment device 200 is configured to heat the inner and/or outer surfaces of the eyelid while compressing the eyelid, similar to the embodiment of FIG. 3A. As the heat from the eye treatment device 200 is transmitted to the eye system 10, particularly to the treatment tissue such as the meibomian glands 18, the heat can soften the meibum and thereby allow the meibum to be more readily expressed during massage or eye exercises. The eye treatment device 200 can include configurations of the modules depicted in FIGS. 2A-2H and FIG. 3A, along with additional components useful in operation of the eye treatment device 200.

The eye treatment device 200 can include a housing 202 having a proximal portion 201 and a distal portion 203 coupled with a removable or consumable portion 260. The housing 202 may include a power source module 110, a controller 212, an energy transducer module 120, and an energy transmission surface 140. The energy transducer module 120 of some embodiments may include an LED device formed of one or more of an LED emitter 207, a thermal management structure 220, and an energy transducer module driver 209. The energy transmission surface 140 and LED emitter 207 are positioned near a distal portion 203 of the housing 202 and are in a slidable relationship along movement path 145 with energy transducer module 120 using actuator 182, which allows for the energy transmission surface 140 to move with the LED emitter 207 simultaneously.

The housing 202 may further include visualization means 160 for enhanced monitoring of the eyelid margin during diagnosis and treatment, a display or dashboard 218 showing various temperatures of the eyelid, such as inner and/or outer surface temperatures, a datalogger 214, and/or voice recorder 213, and circuitry for communication between device and consumable circuitry in order to identify the type of consumable, ensure that the consumable is in proper alignment and/or prevent reuse of the consumable.

The consumable portion 260 may include a scleral shield 300, as discussed above, that can be positioned between the eyelid 12, 14 and eyeball 20 to cover sensitive anatomy of the eye system 10 (such shown in FIG. 1). The scleral shield 300 may be coupled to the housing 202 with one or more support arms 262, with the wires being positioned on or within the arms, and, in certain embodiments, with the structural portion of support arms 262 made from insulating materials surrounding or otherwise channeling the conductive portions of wire or wire array 420.

The eye treatment device 200 can include a power source module 110 for providing power to the various components of the eye treatment device 200 and may be electrically coupled to some or all of the components. In certain embodiments having a controller 212, the controller 212 can receive input instructions from a user (for example, through a user interface device 270, such as a button, switch, touch screen, voice commands, from another module or device, such as a smartphone) to emit light from the LED emitter 207.

The LED emitter 207 is a part of one type of energy transducer module 120 that can be configured to emit light of the appropriate wavelength necessary for the desired treatment. The treatments may include one or more of the following: diagnosing the eyelids 12, 14 by the illuminating the inner and/or outer surfaces, eyelid margins, and/or the meibomian glands behind the eyelids; heating the target tissue region of the eye system 10 (e.g., the meibomian gland behind the eyelids 12, 14); and antibacterial treatment to kill bacteria in the eye system 10.

In some embodiments, an additional shielding element 258 may be used to prevent unwanted photonic energy (such as IR or blue/violet light) from reflecting off the transillumination element back to the clinician.

A feature of many of the embodiments disclosed herein is the ability of the clinician to view the eyelid margin during the application of heat and compression. By viewing the margin, the clinician can see what contents, if any, are being expressed from the meibomian ducts, and thereby adjust the amount of heating and compression applied to the eyelid being treated in order to optimally unclog blocked meibomian glands. By way of example, a clinician may observe at the start of a treatment that certain meibomian glands in the portion of the eyelid being treated have a clear oily discharge, which signals normal glands. In contrast, some glands may secrete a cloudy oily discharge, or small amounts of thick, toothpaste-like lipid, both of which signal a dysfunctional gland. As the clinician applies heat and compression to the portion of the eyelid being treated, further observation of the dysfunctional glands can show that the cloudy or thick secretions change to clear, and the amount of discharge may suddenly increase, indication that the gland or glands have been unclogged. At such point, the clinician may reduce the heat and compression applied to that region, since the treatment has successfully unclogged the blocked glands. Without this continuous visual feedback, the clinician would be relegated to applying a standard treatment regimen, which may either be under- or over-aggressive for the particular clogged gland(s) in a given patient.

By way of reference, at least FIGS. 2D, 2E, 2F, 2G, 2H, 3A, 3B, 15A, 15B and 15D each show example of embodiments wherein the eyelid margin is exposed for a clinician to visually monitor during treatment. The clinician would be positioned in front of the eye being treated.

Figure 16A:
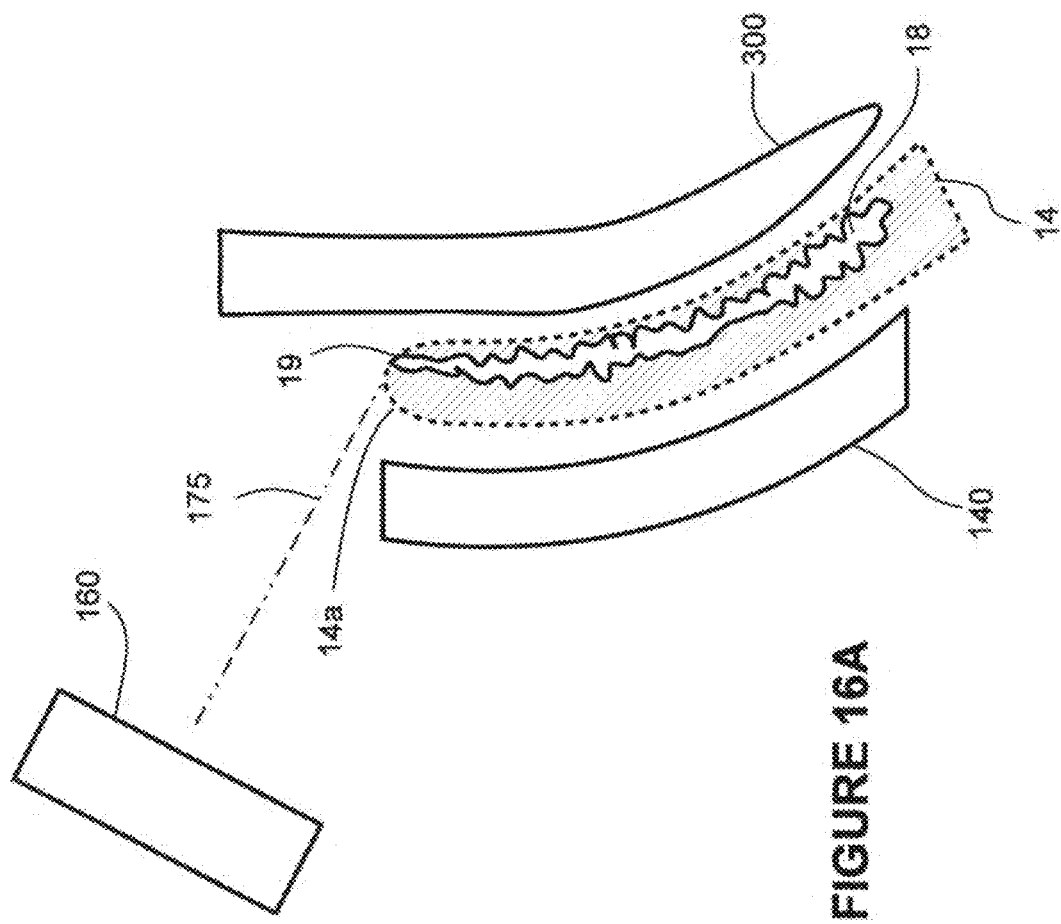
FIGS. 16A-O show unique configurations of the energy transmission surfaces, the scleral shields and support arms of the system, which define an aperture that allows viewing of one or both eyelid margins during the application of heat and compression to the portion of the eyelid being treated.

Referring now to FIG. 16A, a side cross-sectional view is shown of an energy transmission surface 140, an eyelid 14 with an eyelid margin 14a, a scleral shield 300, and a visualization means 160 with optical path 175. This embodiment is the same as is shown in FIG. 2E, except without image translator 155. In the embodiment of FIG. 16A, the visualization means is directly focused on eyelid margin 14a, and more specifically on meibomian ducts 19.

FIG. 16B is a front perspective view of the same embodiment of FIG. 16A, showing an example where eyelid 14 is compressed between energy transmission surface 140 and scleral shield 300, while eyelid margin 14a is viewable from the front by a clinician. This embodiment is the same as shown in FIG. 2F without image translator 155.

FIG. 16C is a similar embodiment as shown in FIG. 16A, with the addition of support arm 262. Support arm 262 is the same as shown in FIGS. 3A, 3B, 7H, 7G, and 15B.

Figure 16E:
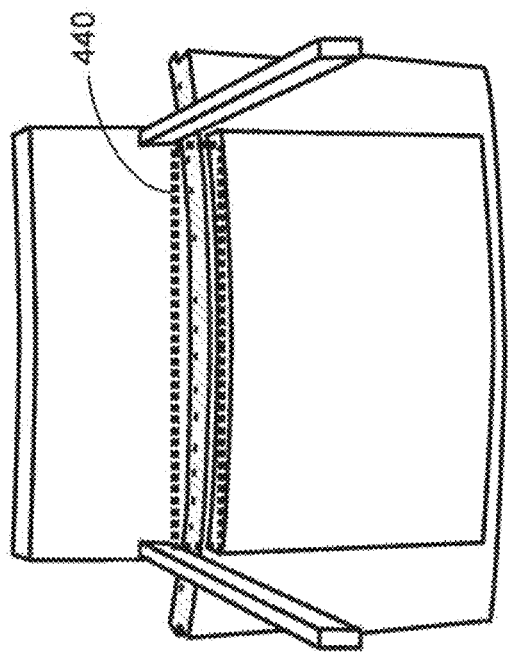
Figure 16D:
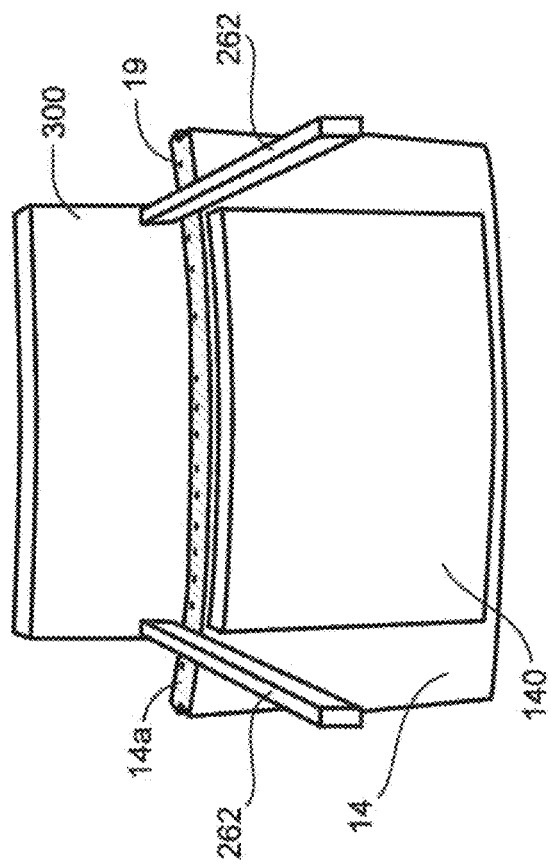
Figure 16G:
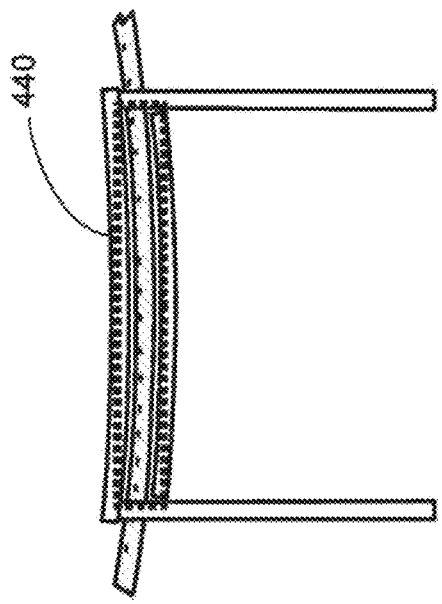
Figure 16F:
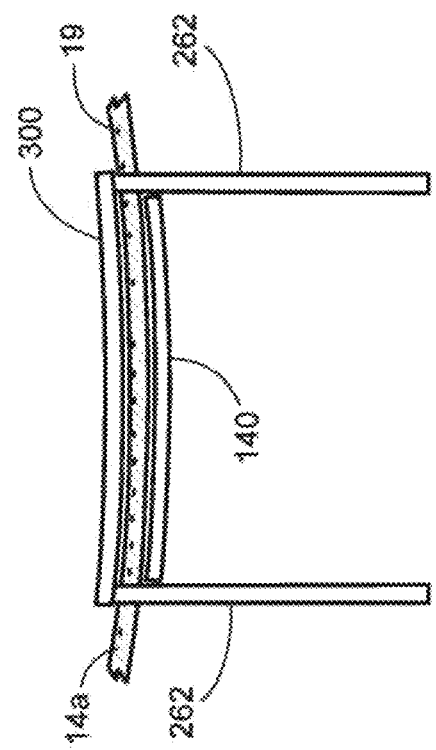

FIG. 16D is a front perspective of the embodiment shown in FIG. 16C, showing a pair of support arms 262 coupled to scleral shield 300. Eyelid margin 14a is exposed, and is adjacent to the bottom edges of support arms 262, by way of example but not limitation. FIG. 16E is the same as FIG. 16D but with aperture 440 for viewing the eyelid margin 14a highlighted by the bold dotted rectangle. FIG. 16F is a top view of the embodiment of FIGS. 16D and 16E, showing energy transmission surface 140 compressing the eyelid against scleral shield 300, with eyelid margin 14 exposed for visual monitoring. FIG. 16G is the same as FIG. 16F but with aperture 440 for viewing the eyelid margin 14a highlighted by the bold dotted rectangle. In an embodiment, the distance between the arms is between 0.2 inches and 1.2 inches. In an embodiment, a distance between a line defined by the points of attachment between the two arms and the backplate and a line defined by the points of attachment between the two arms and compression element is at least 0.04 inches.

Figure 16I:
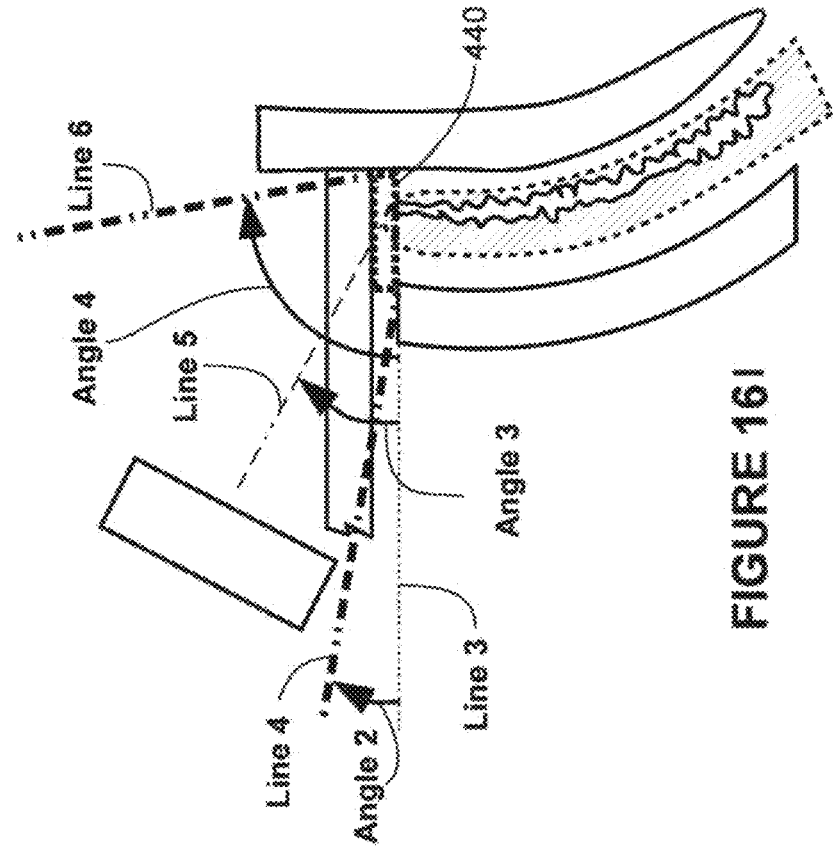
Figure 16H:
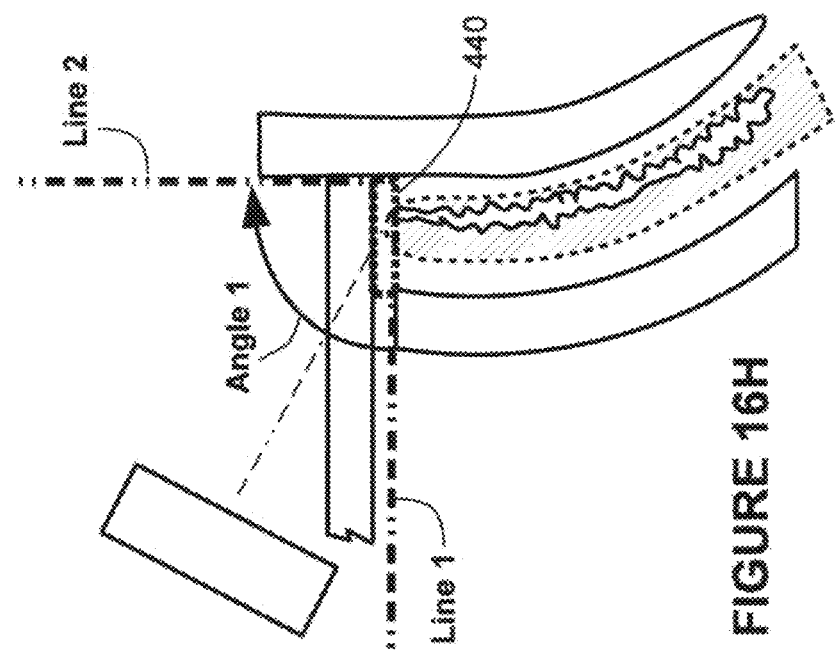

FIG. 16H is a more detailed side cross-sectional view of the embodiment of FIG. 16C, further defining the boundaries of aperture 440 in certain preferred embodiments. In the figure, Line 1 indicates the lower (horizontal) boundary of the aperture, and Line 2 defines the upper (vertical) boundary. Angle 1 is the angle between Lines 1 and 2, and is theoretically about 90 degrees, although variations in the anatomy of cheekbone and eyebrow structure may result in variations in these boundaries. FIG. 16I is a more detailed depiction of the embodiment of FIG. 16H, wherein the preferred lower boundary of aperture 440 is shown as Line 4 and the preferred upper boundary of aperture 440 is shown as Line 6. Angle 2 is the angle between horizontal Line 3 and Line 4, and is preferably between about 5 and about 20 degrees, while Angle 4 is between Lines 3 and 6, and is preferably between about 60 and 80 degrees. Angle 3 is the angle between Line 3 and Line 5 and is a preferred angle of viewing of eyelid margin 14a through aperture 440, and is preferably between about 25 and 50 degrees.

Figure 16K:
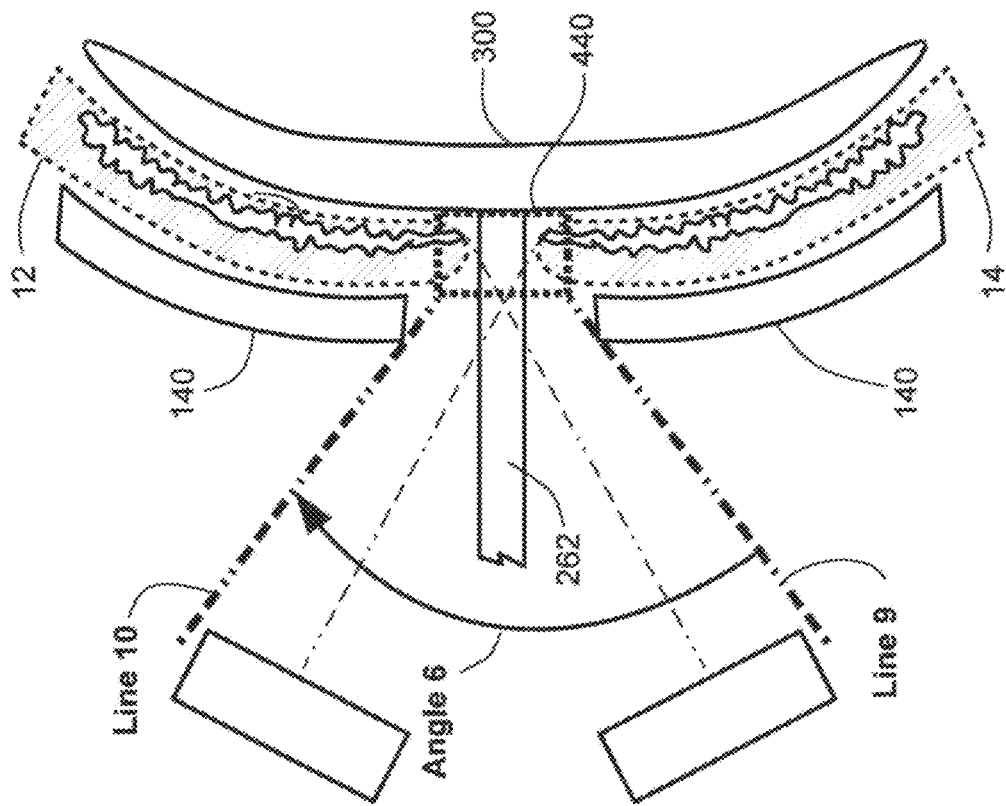
Figure 16J:
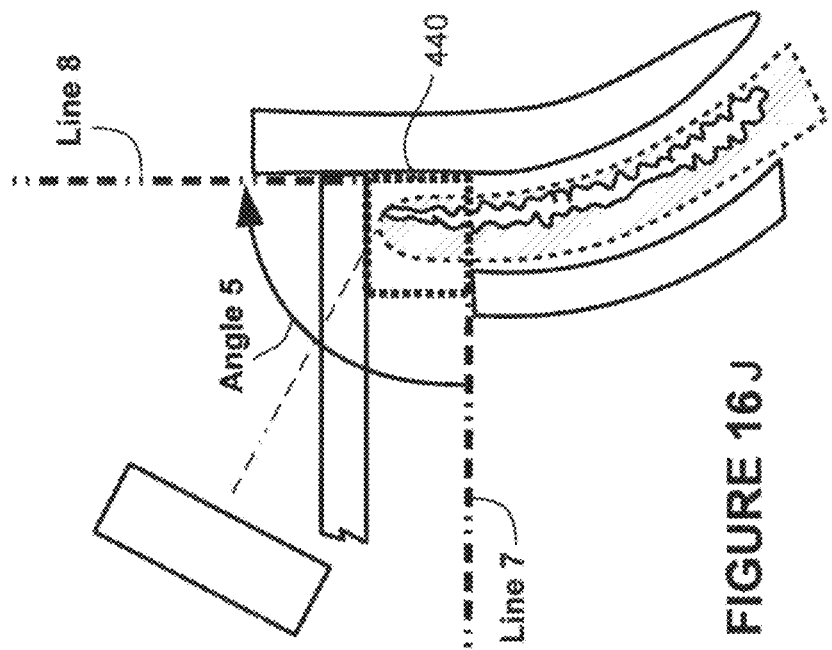
Figure 16:
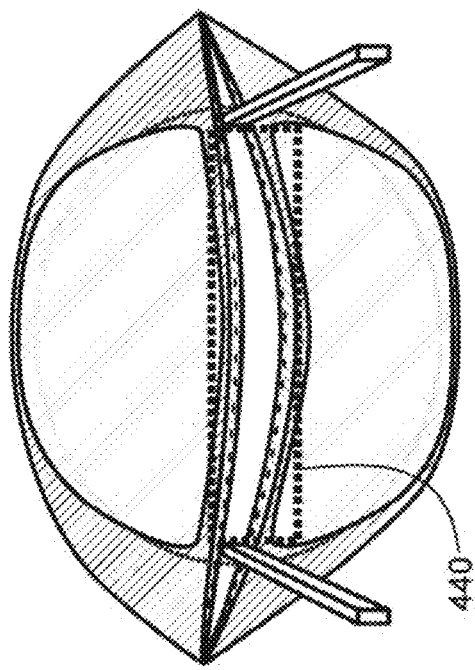

FIG. 16J depicts an embodiment similar to 16H, except energy transmission surface 140 is shorter than that shown in FIG. 16H, thereby exposing more of the upper part of eyelid 14 adjacent to eyelid margin 14a. In this embodiment, aperture 440 is larger, although the outer boundaries defined by lines 7 and 8 are parallel to those defined by Lines 1 and 2 in FIG. 16H, and Angle 5 between them is therefore also about 90 degrees.

FIG. 16K is similar to the embodiment shown in 16J, except scleral shield 300 extends behind both the upper and lower eyelid, and there are portions of energy transmission surface 140 that are adjacent to upper eyelid 12 as well as lower eyelid 14. In this embodiment, both the upper and lower eyelids are being heated and compressed instead of just the lower eyelid. As shown, support arm 262 is linked to scleral shield 300, and energy transmission surfaces 140 are configured so as to allow viewing of both the upper and lower eyelid margins through aperture 440. Lines 9 and 10 depict the approximate lower and upper limits of aperture 440, thereby defining Angle 6, which is preferably between about 10 and 150 degrees, and more preferably between about 20 and 120 degrees. It will be appreciated that many modifications to the embodiments herein disclosed are possible, some of which may alter the optical path and thereby change the angles associated with the aperture. For example, an image translator such as that shown in FIG. 2E may be employed, as may other means of reflecting, guiding or translating the image of the eyelid margin through an aperture to a clinician. Alternatively, the aperture may be an optically transmissive window through a structural element. For example, in FIG. 16K, energy transmission surface 140 may completely cover both the portions of the upper and lower eyelids being treated, and instead of there being an opening near the eyelid margin, at least a segment of energy transmission surface 140 may be transparent enough for a clinician to view the eyelid margin. Further, there could be an image sensor, fiberoptic bundle or light pipe mounted adjacent to, or directed at, the eyelid margin, and the image of the eyelid margin could be transmitted electronically or optically to a point outside the energy transmission surface 140. All of these alternate embodiments, and others apparent to those skilled in the art, are included within the scope of this disclosure.

Figure 16L:
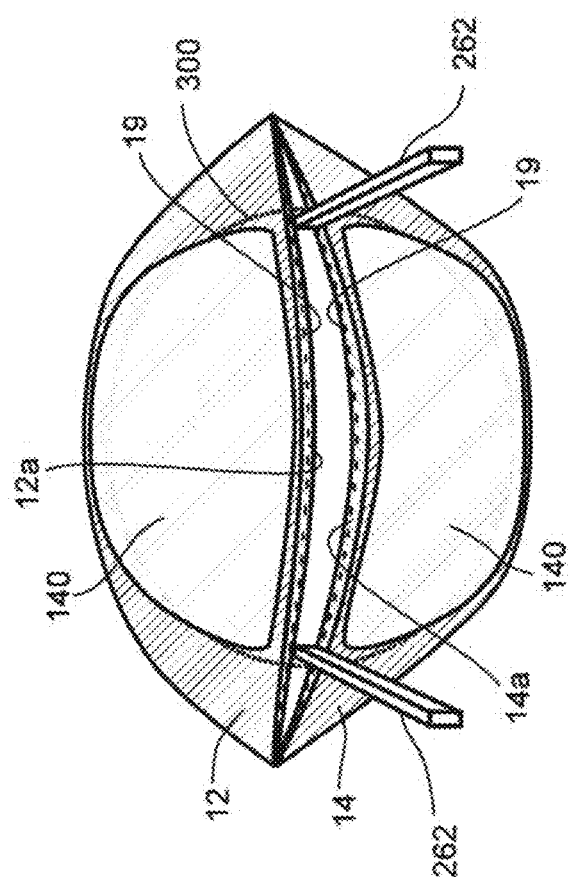

FIG. 16L shows the embodiment of FIG. 16K in a front perspective view. As shown, dual support arms 262 are linked to scleral shield 300, and dual energy transmission surfaces 140 are shown adjacent to the upper eyelid 12 and lower eyelid 14. As shown, the upper and lower eyelid margins, 12*a* and 14*a*, respectively, are visible, and meibomian ducts 19 are visible as well. FIG. 16M is the same as FIG. 16L, with aperture 440 generally defined by the bold dotted rectangle shown.

Figure 16N:
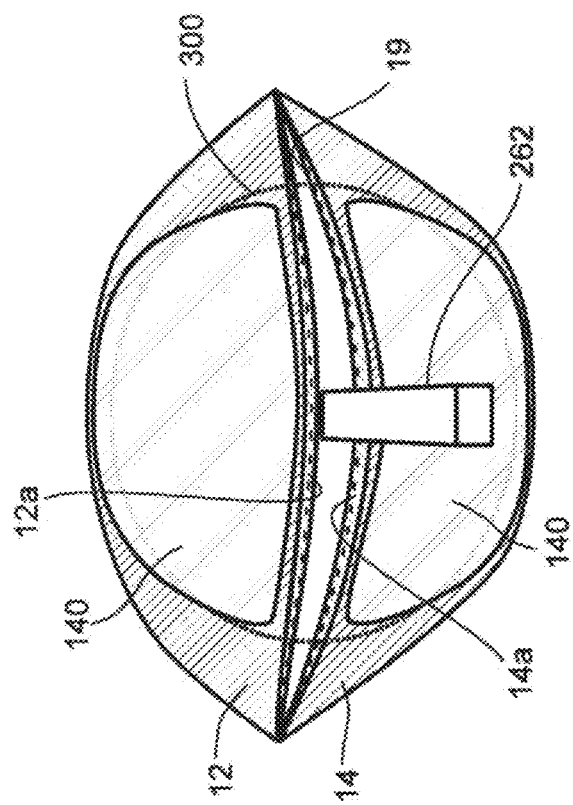
Figure 16O:
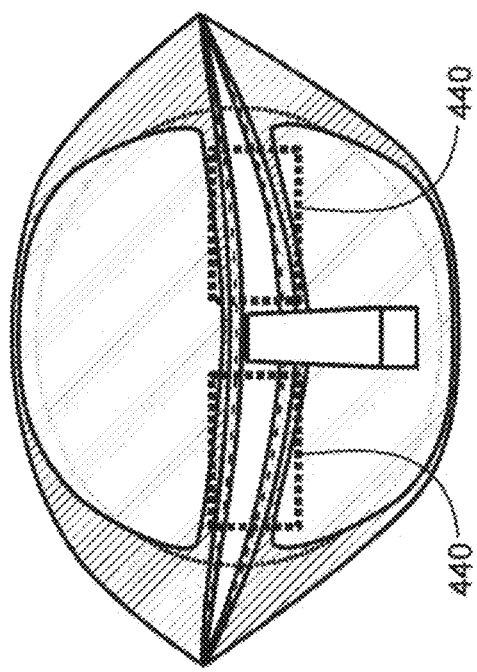

FIG. 16N is similar to the embodiment of FIG. 16L, but with a single support arm 262. FIG. 16O is the same as the embodiment of FIG. 16N but highlighting the two apertures 440 defined by the gaps between the upper and lower energy transmission surfaces 140, and to the right and left of central support arm 262. Other combinations of single or multiple support arms or other structures having single or multiple apertures may be contemplated by those skilled in the art.

It will be appreciated that FIGS. 16A-16O show the unique configuration of the energy transmission surfaces 140, the scleral shields 300 and support arms 262, which define an aperture 440 that allows viewing of one or both eyelid margins during the application of heat and compression to the portion of the eyelid being treated. Many other configurations are possible and only a few exemplary embodiments have been described herein to demonstrate the innovative concept.

Figure 17B:
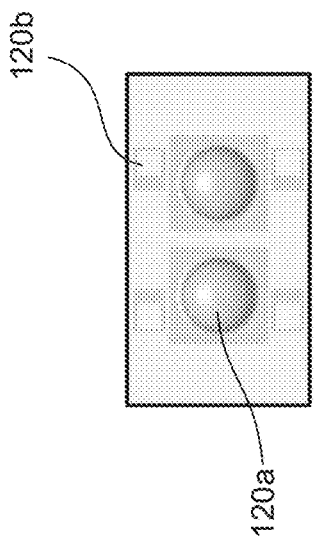
FIGS. 17A-C show an embodiment of an energy transducer module in combination with an energy waveguide module and energy transmission surface.
Figure 17A:
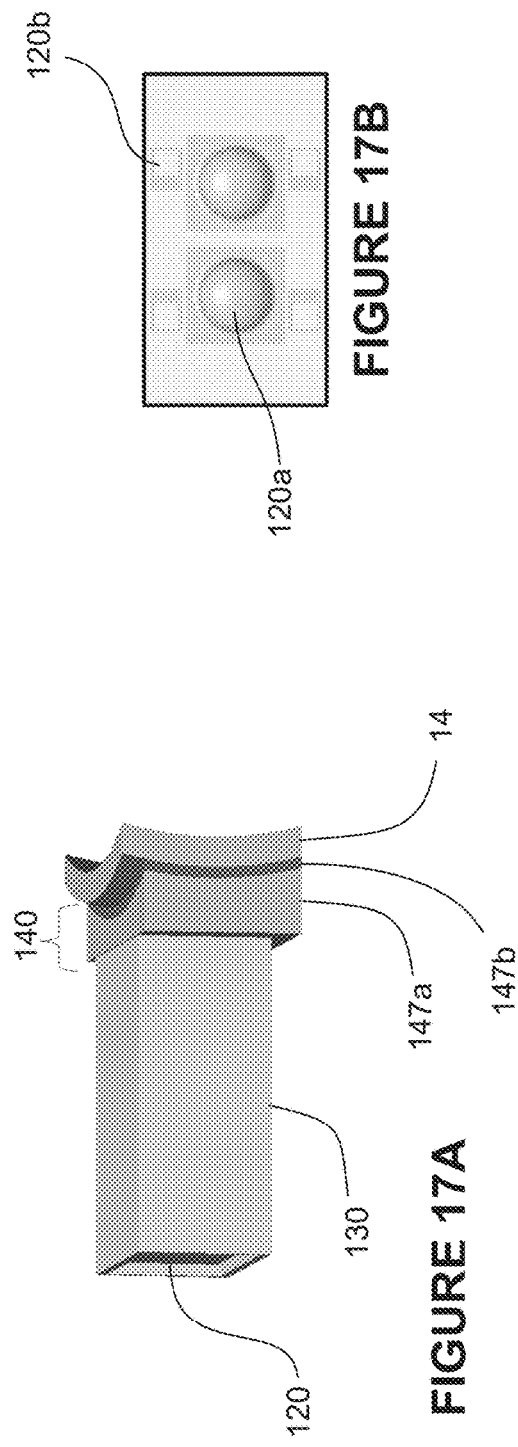
Figure 17C:
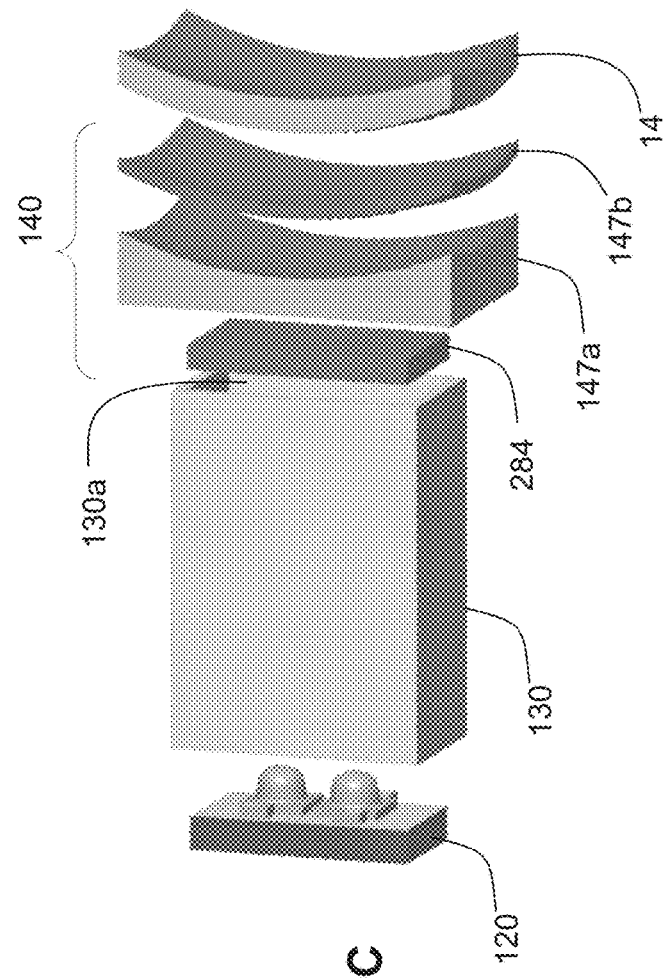

Referring now to FIG. 17A, an assembly is shown similar to portions of the embodiment shown in FIG. 3A. Energy transducer module 120 is positioned adjacent to the proximal end of energy waveguide module 130. The distal end of energy waveguide module 130 is adjacent to energy transmission surface 140, made up of face glass 284 (shown in FIG. 17C) and single-use cover element parts 147*a* and 147*b*. Part 147*b* abuts eyelid 14. FIG. 17B is a front view of energy transducer module 120, consisting of two infrared LEDs 120*a* and four lime emitting LEDs 120*b*, all mounted on a substrate. FIG. 17C is an exploded view of the same components described in FIGS. 17A-B, including a call-out 130*a* for the inside surface of energy waveguide module 130. In some embodiments, energy waveguide module 130 may be in a fixed relationship with energy transducer module 120, while in other embodiments, energy waveguide module 130 may slide with respect to energy transducer module 120, and in others energy transducer module 120 may slide with respect to 130. In a preferred embodiment, energy transducer module 120 is fixed and energy waveguide module 130 slides back and forth around energy transducer module 120. In such a preferred embodiment, when energy waveguide module 130 is fully advanced, it pushes energy transmission surface 140 against eyelid 14 (or 12, when treating an upper eyelid).

In order to maximize the efficiency of transmitting light energy from energy transducer module 120 to energy transmission surface 140, the inner surface of energy waveguide module 130 may be coated or lined with a material that is highly reflective to the wavelengths emitted by energy transducer module 120. By way of example, the inner surface of energy waveguide module 130 may be coated with a protected silver material, or it may be lined with films such as WRF-150 from Fusion Optix, or ESR film from 3M, all of which are designed to provide >97% reflection of the wavelengths between 500 nm and 900 nm.

In certain embodiments, single-use cover element part 147*a* may be fabricated from a plastic or glass material that transmits light energy in the 500-880 nm range. Acrylic is one example of an acceptable material for single-use cover element part 147*a*. Single-use cover element art 147*b* is preferably a low durometer material such as silicone in order to provide a soft surface to press against the surface of the eyelid. Since most silicones are not fully transparent to infrared energy, it is preferable to keep the thickness of single-use cover element 147*b* in the range of about 0.02-0.06 inches in order to minimize energy loss.

Figure 17D:
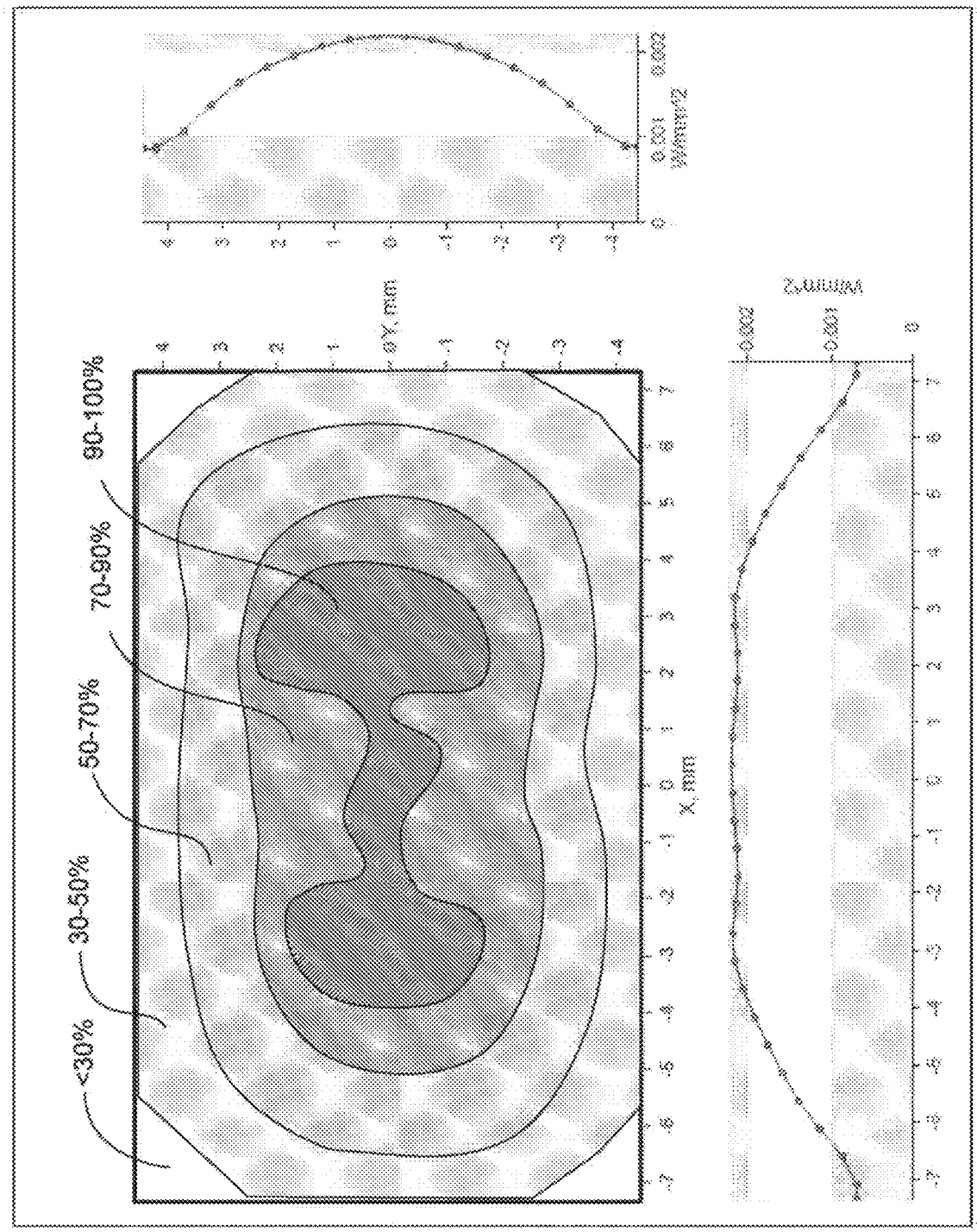
FIG. 17D shows a graphical representation of the irradiance distribution of infrared light through an eyelid for the embodiment of FIGS. 17A-C.

FIG. 17D shows the distribution of infrared energy transmitted through eyelid 14 when module is fully advanced (with its distal end about 0.5 inches from the highest point on the infrared LED lens). Referring to the graph shown in the upper left, the darker regions are the areas of highest irradiance (Watts per square millimeter), while the lighter regions are the lowest irradiance. As shown, the highest irradiance occurs near the middle, and the irradiance drops off sharply toward the edges. The asymmetrical distribution across the X axis is not ideal, since it is desirable to heat the eyelid tissue evenly across from one edge to the other. In the Y-axis direction, some asymmetry is desirable, since most of the blockages that occur in a meibomian gland are near the orifice or duct. In the case where a lower eyelid is being treated, and the top edge of the energy transmission surface 140 is aligned with the top edge of the lower eyelid, it would be preferable to have the irradiance profile (and therefore the tissue heating profile) be biased toward the top edge, while also warming the overall eyelid.

Figure 17F:
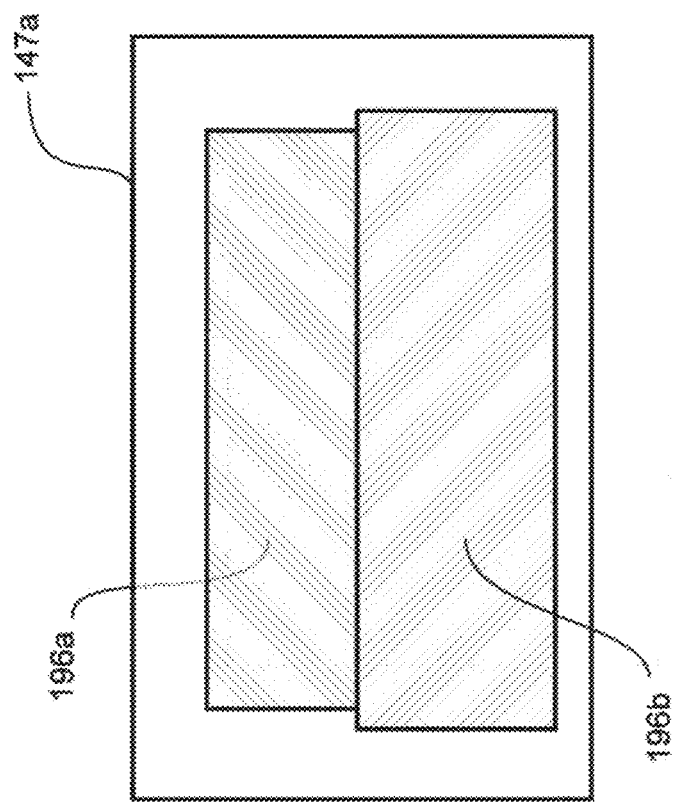
FIGS. 17E-F depict an element of an energy transmission surface having a certain coating.
Figure 17E:
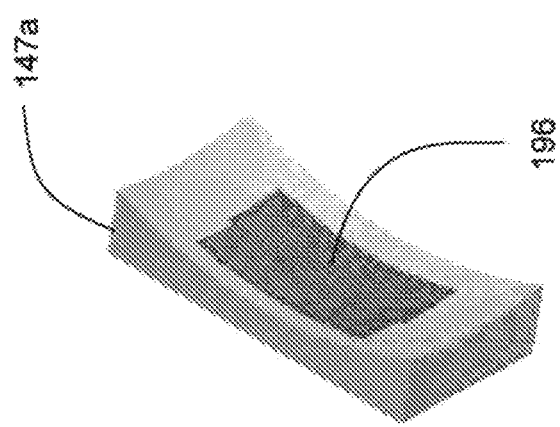
Figure 17G:
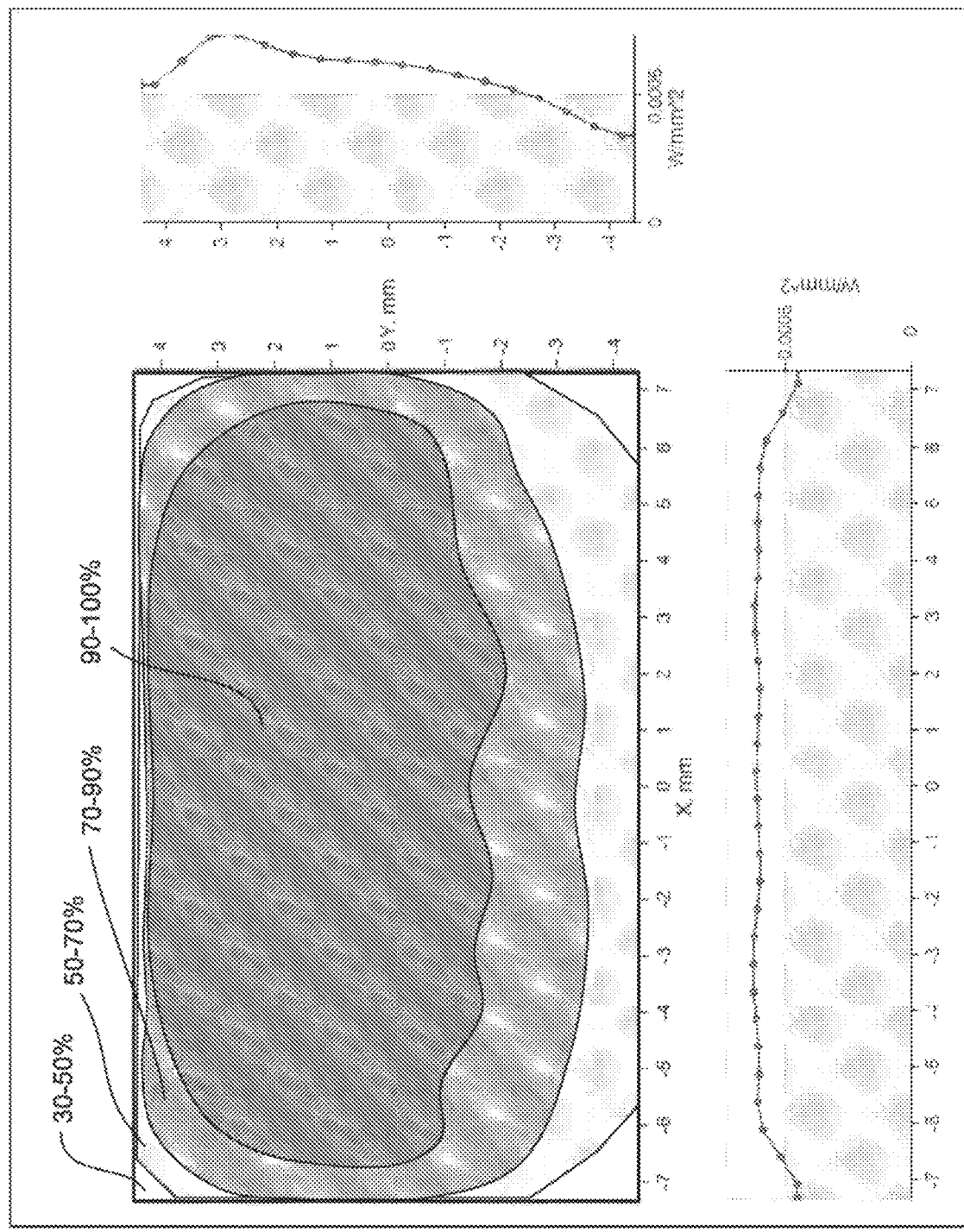
FIG. 17G is a graphical representation of the irradiance distribution of infrared light through an eyelid for an embodiment having a certain coating on a portion of the energy transmission surface.

In order to improve the distribution of irradiance of the infrared light, a partially reflective coating 196 may be applied to a surface of part single-use cover element part 147*a*, as shown in FIG. 17E. In one embodiment, this coating is an apodization coating which transmits about 33% and reflects about 67% of the energy in the 820-880 nm range. FIG. 17F shows a more detailed view of the coating pattern, with two zones 196 *a* and 196 *b* shown. FIG. 17G shows the resulting distribution of irradiance through the eyelid when the apodization coating is utilized. As shown, the highest irradiance zone is much wider and is skewed toward the top edge, and there is much less drop-off in irradiance toward the right and left ends along the top edge. As such, there will be preferential heating of tissue along the upper half of the eyelid (in the case of treating a lower eyelid), and the heating from left to right across the eyelid is more uniform.

If the apodization coating 196 is also reflective of wavelengths in the lime region (500-600 nm), then very little lime light will reach the desired parts of the eyelid, and there will therefore be less heating of the eyelid tissue through chromophore absorption of the lime light energy. To address this, in one embodiment, it is preferable for coating region 196 *a* to be partially reflective only for infrared only (67% reflective, 33% transmissive for 820-880 nm; >90% transmissive for lime 500-600 nm), and for coating region 196 *b* to be partially reflective (67% reflective, 33% transmissive) to both infrared (820-880 nm) and lime (500-600 nm).

Figure 17H:
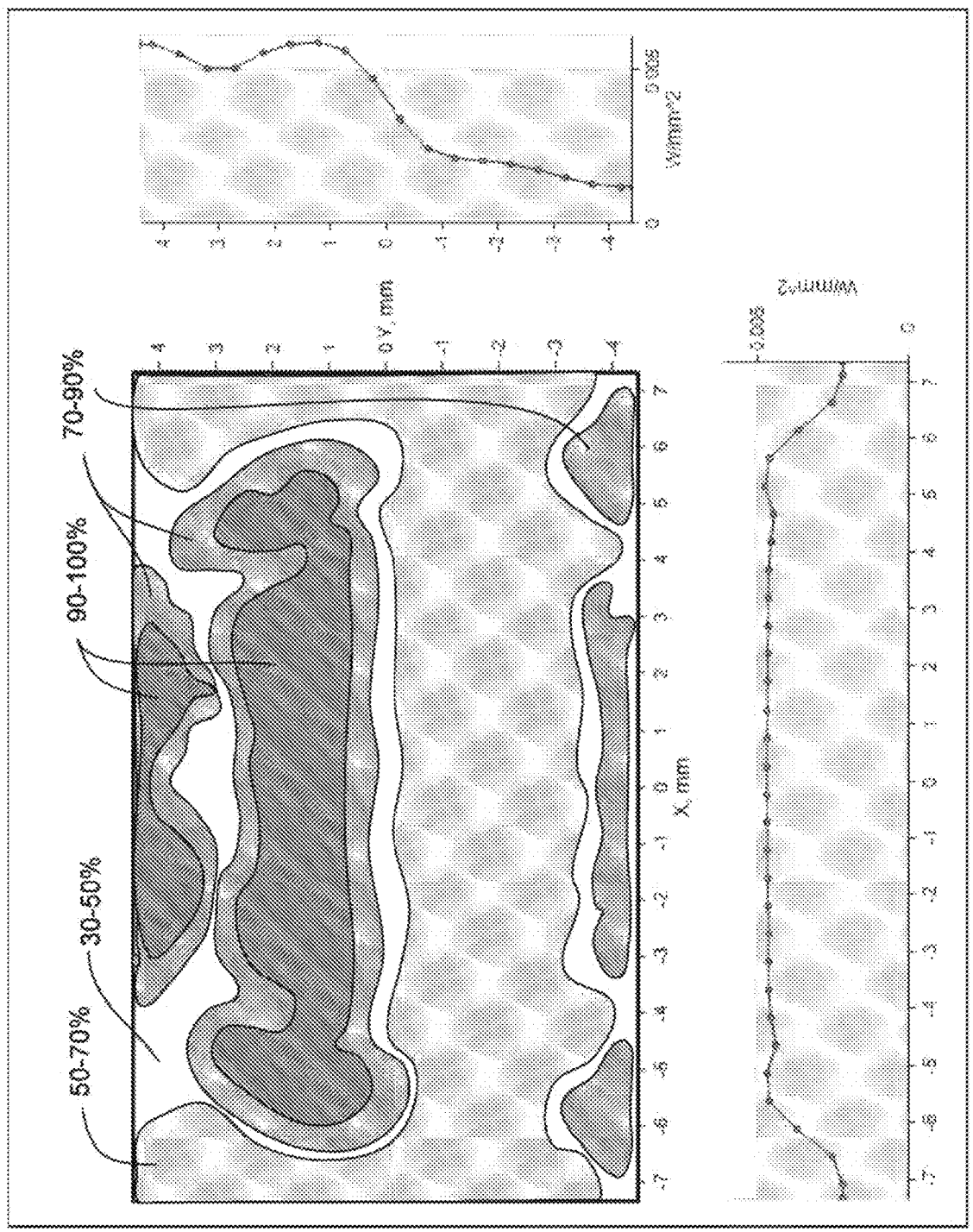
FIG. 17H shows the irradiance distribution of lime light on the outer surface of an eyelid for an embodiment having a certain coating on a portion of the energy transmission surface.

FIG. 17H shows a lime irradiance distribution plot on the surface of the eyelid for an embodiment having an apodization coating as described above (zone 196 *a* transmits lime and partially reflects infrared, and zone 196 *b* partially reflects both). As can be seen, the irradiance pattern is preferentially skewed to the upper half of the eyelid and is well distributed from the right to left end, without significant drop-off in irradiance.

It will be appreciated that the examples of coating types and deposition patterns disclosed herein are simple examples of demonstration and that alternate configurations may result in more even distribution of irradiance in the desired spectra. For example, another method of shaping the heating pattern of the eyelid is to modify the deposition pattern or properties of the energy absorbing surface 302 of scleral shield 300 (as shown in FIG. 3B). For example, in order to even out the heating of the scleral shield if the irradiance pattern is as shown in FIG. 17D, the right and left portions of the surface of scleral shield 300 may be more densely coated with energy-absorbing material than the central portions of scleral shield 300. Further, in order to skew the heating toward the upper portion of the eyelid, the upper portion of the surface of the scleral shield could be more densely coated with energy-absorbing material. Combinations of coatings on elements within the energy transmission path as well as alterations of the energy reflecting and absorbing properties of the surface of the scleral shield are all included within the scope of the disclosure.

Figure 18A:
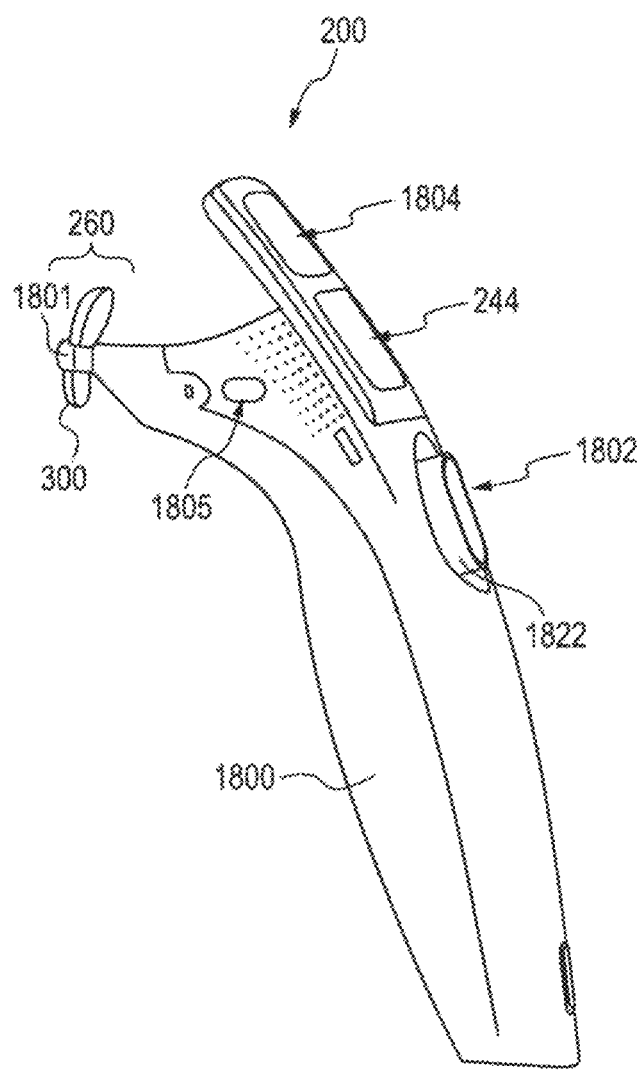
FIGS. 18A and 18B are front and side views of another embodiment of an eye treatment device.
Figure 18B:
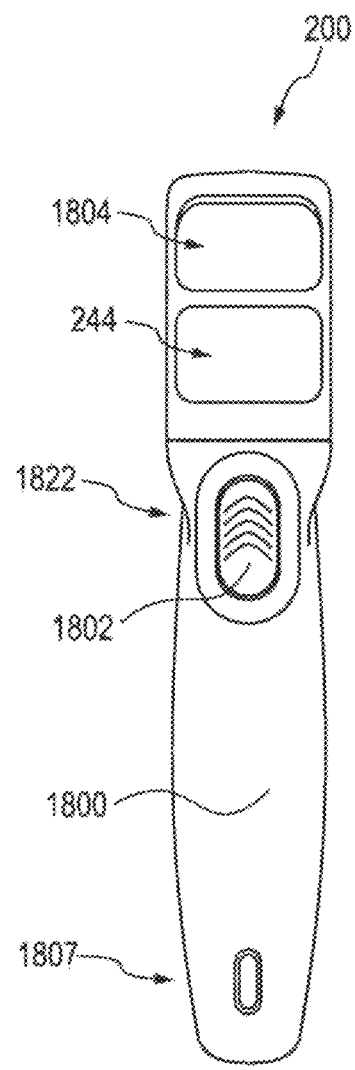

FIGS. 18A and 18B show another embodiment of an eye treatment device 200. In some embodiments, the eye treatment device 200 may be configured for use by an Eye Care Professional (ECP). For example, the eye treatment device 200 can allow an ECP to apply localized heat and pressure to the eyelids 12, 14 (not shown in FIGS. 18A-18B). In some embodiments, the system can include a handheld instrument 1800 configured to be coupled to a sterile disposable component 260 positioned behind the eyelids 12, 14. For example, the sterile disposable component 260 may be single-use, removable, or consumable. In some embodiments, the sterile disposable component 260 can be releasably attached to the handheld instrument 1800, and the handheld instrument 1800 can include a disposable release button 1805. In some embodiments, the handheld instrument 1800 also includes a power button 1807. In some embodiments, the eye treatment device 200 device can allow an ECP to view the eyelid margin through a visualization device or visualization means 160, such as an integrated camera. The eye treatment device 200 can then warm the eyelid tissue to a target temperature range, such as to melt the meibum blocking the orifices. In embodiments, the target temperature range is about 40° C. to about 42° C. The eye treatment device 200 can further apply compression to the eyelids 12, 14, such as to express the melted meibum through the orifices. In some embodiments, the amount of heat and pressure applied is under direct control of the ECP at all times, and the ECP may monitor the response of the glands and the comfort of the patient during treatment.

As shown in FIGS. 18A-18B, the eye treatment device 200 can include an electronic handheld instrument 1800. The handheld instrument 1800 can be used together with the sterile disposable component 260, for example, to apply heat and pressure to the eyelids 12, 14. The eye treatment device 200 can have the approximate dimensions of 8" (L)×1½" (W)×2¼" (H). The eye treatment device 200 may have other dimensions without departing from the scope of the present disclosure. In some embodiments, the sterile disposable component 260 can be secured to the handheld instrument 1800 by at least two latches 1801. The at least two latches 1801 may grasp at least one attachment tab 2203 (not shown). The sterile disposable component 260 may be released from the handheld instrument 1800 by pressing the disposable release button 1805. The eye treatment device 200 can include electronic circuits that read temperature sensors 310 in the inner eyelid pad 300 and the outer eyelid pad 147. The electronic circuits can be used to measure temperatures representative of inner and outer eyelid temperature. Warming can be accomplished using light energy emitted from LEDs in the handheld instrument 1800 A mechanism in the handheld instrument 1800 can allow the operator to apply pressure to the eyelid by controlling the movement of the outer eyelid pad 147 using finger pressure applied to a compression control button 1822. In some embodiments, the eye treatment device 200 can also include a graphic screen or display 244 configured to display information used to operate the handheld instrument 1800 such as during a treatment. In some embodiments, the eye treatment device 200 can include a visualization device or visualization means 160, configured to allows the operator to view the eyelid margin during treatment.

Eyelid temperature can be measured using sensors 310 in the sterile disposable component 260, including two sensors in the outer eyelid pad 147 and two sensors in the inner eyelid pad 300. For example these sensors can be mounted on a flexible printed circuit board (PCB) that may also have an array of contact pads. When the sterile disposable component 260 is attached to the handheld instrument 1800, spring loaded pins mounted below a shroud 2100 (not shown) can make an electrical connection to the outer eyelid pads 140 and the inner eyelid pads 300 in the sterile disposable component 260. In some embodiments, electronic circuitry in the handheld instrument 1800 can read the sensors and determine temperatures rapidly, for example more than 20 times a second. The accuracy of the temperature measurement system can be ±1° C. In some embodiments, the electronic circuitry performs self-test checks to ensure the sensors are operating properly. For example, if the electronic circuitry detects a failure, an error code may be displayed and the heat source may be disabled.

In some embodiments of the eye treatment device 200, pressure applied to the eyelid can be controlled by the ECP, such as by the ECP depressing the compression control button 1822 using their thumb or finger. This depression of the compression control button 1822 can cause the outer eyelid pad 147 to move towards the opposing inner eyelid pad 300. In some embodiments, when the sterile disposable component 260 is attached to the handheld instrument 1800 the outer eyelid pad 147 automatically attaches to the front of the shroud 2100. The shroud 2100 may be a component that may be movable, and which encloses the warming LEDs and guides light towards the eyelid. In some embodiments, the compression control button 1822 is connected to the shroud 2100, thereby enabling the clinician to advance the outer eyelid pad 147 using thumb or finger force. For example, the force applied can be measured by a sensor mounted in the mechanism of the compression control button 1822, and can be displayed on the display screen 244 as a relative number from 1 to 9. The displayed value may be a relative reference for the clinician. The actual force applied should be determined by clinical judgment, taking into consideration the condition and response of the eyelid being treated as well as patient sensitivity.

In some embodiments, the eyelid tissue can be warmed by light energy produced by LEDs in the handheld instrument 1800 and transmitted through the clear outer eyelid pad 300. The LEDs can be located behind a clear window on an open end of the shroud 2100. For example, two wavelengths of light can be used: lime-green and near-infrared. Chromophores in the eyelid can absorb the light energy and thereby heat the surrounding tissue.

In some embodiments, the top surface of the compression control button 1822 has a heater control switch 1802 that can be slid forward by the operator's thumb or forefinger, thereby turning on the warming LEDs. This heater control switch 1802 can have a spring-return feature, such that when it is released, or when the operator's thumb or forefinger is relaxed, the heater control switch 1802 returns to its normal "off" position.

In some embodiments, the eye treatment device 200 may be designed to protect the eye against unintended exposure to the light. For example, the inner eyelid pad 300 and an eye shield can block light 211 from directly shining into the eye during a treatment. In some embodiments, the handheld instrument 1800 can disable the warming of the LEDs if a valid sterile disposable component 260 is not attached to the handheld instrument 1800, or if the outer eyelid pad 147 is more than 6 mm from the inner eyelid pad 300.

Figure 19:
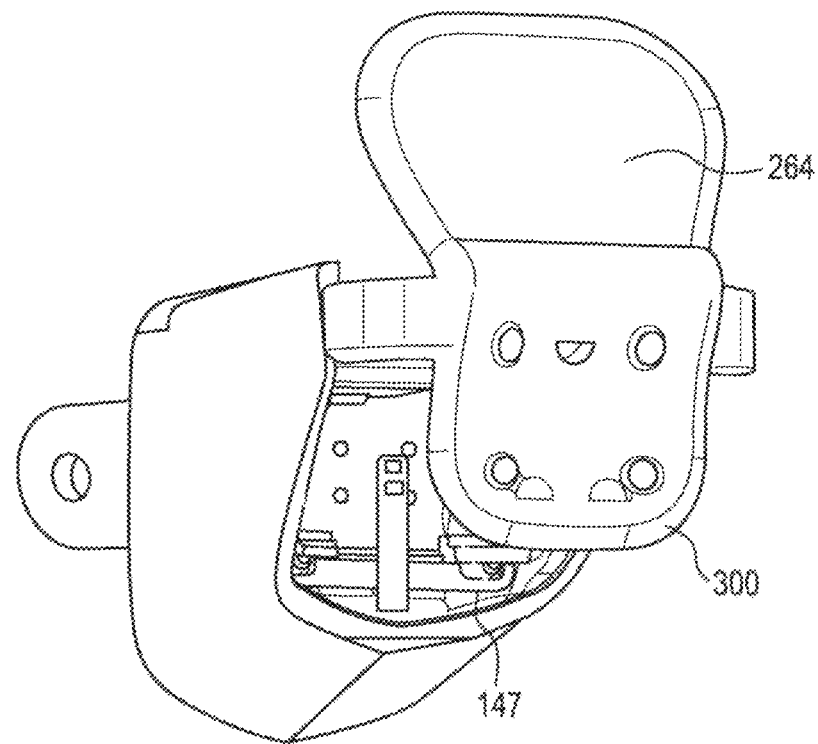
FIG. 19 is a view showing one embodiment of the frontplate of the disposable.

FIG. 19 shows an example of a frontplate or force pad used as the outer eyelid pad 147, which may be interposed between the eye treatment device 200 and the eyelids 12, 14 of the patient, such as to provide a barrier therebetween. In some embodiments, the outer eyelid pad 147 can be a transparent outer eyelid pad 147 that may act as a window through which the energy can be delivered to the eyelids 12, 14. For example, the transparent outer eyelid pad 147 may be fabricated from any suitable material such as glass, pyrex, quartz, mica, or polymers such as polycarbonate or other optically transparent materials, or a combination thereof, in order to obtain the desired structural and optical properties. In embodiments, the outer eyelid pad 147 can be configured to directly contact the eyelids 12, 14 of the patient. In other embodiments, the outer eyelid pad 147 can be configured to be spaced a small distance from the eyelids 12, 14, such as for example between 0.5 mm and 12 mm from the eyelid, during a treatment. Preferably, the exterior surface of the outer eyelid pad 147 is configured to be smooth and easily cleaned. For example the transparent outer eyelid pad 147 may be in a slidable relationship along movement path 145 with respect to either the energy transducer module 120 or scleral shield 300 or housing 202, so as to ensure the transparent outer eyelid pad 147 can be pressed up against the eyelids 12, 14. The pressure of the transparent outer eyelid pad 147 against the eyelids 12, 14 can serve to minimize photonic energy leakage during treatment and/or imaging, and if desired, to apply a compressive force to the eyelids 12, 14 during evaluation and/or expression of meibomian glands.

FIG. 19 shows an embodiment of an outer eyelid pad 147 that includes a set of temperature sensors 310 positioned toward the outer eyelid. In some embodiments, the set of temperature sensors 310 may be discrete elements (such as thermocouples made from very fine wire, miniature thermistors, etc.) embedded or positioned in the outer eyelid pad 147. Additionally and/or alternatively, the set of temperature sensors 310 may be thermocouples formed by depositing a thin film or films of appropriate metals onto intermediate layers of the outer eyelid pad 147. In some embodiments, the preferred types of materials for the outer eyelid pad 147 are soft, flexible, biocompatible materials such as silicone, polyurethane, and various hydrogels similar to those used in contact lenses.

In embodiments, the outer eyelid pad 147 may also include a plurality of bumps on the eyelid-facing surface, such as to create an airspace for the set of temperature sensors 310.

The set of temperature sensors 310 may be configured to sense the position of the eye treatment device 200 relative to the eyelids 12, 14 of a patient. The set of temperature sensors 310 may be temperature sensors that measure room temperature prior to placement of the eyelid in the device. As the set of temperature sensors 310 is positioned near the eyelid skin, the set of temperature sensors 310 will register a value closer to body temperature and therefore confirm proper positioning. If the set of temperature sensors 310 does not match, such as one sensor showing room temperature and the other sensor showing eyelid temperature, it may be an indication that the eyelid is not properly positioned in the eye treatment device 200 for treatment.

FIG. 19 shows an embodiment of a frontplate or outer eyelid pad 147 having sensors 310 designed the measure the eyelid temperature. When infrared light waves hit the skin, part of the light is reflected back toward the sensors 310 and may heat the sensors 310. This may cause the reading of the eyelid temperature to be incorrect. In some embodiments, to prevent unwanted photonic heating of the sensors 310, a reflective and/or white paint may be used to over the sensors 310.

Referring again to FIG. 19, when infrared light waves hit the skin, they are absorbed and the energy from the light is transferred into heat thereby warming the skin. In general, darker skin colors absorb more infrared light than lighter skin colors, which therefore means that darker skin becomes hotter faster as it is transforming more light into heat.

Using this knowledge, the eye treatment device 200 may be able to detect differences in skin pigmentation and adjust the treatment accordingly. For example, the eye treatment device 200 can have sensors 310 on the frontplate and stationary backplate to measure the inner eyelid surface temperature and the outer eyelid surface temperature during heating. If the outer eyelid surface warms quickly, it might be an indication of darker skin color, conversely if the outer skin surface warms slowly, it might indicate a lighter skin color.

In some embodiments, to compensate for this difference in warming rates for different levels of skin pigmentation, the eye treatment device 200 may adjust the light such that the inner and outer skin warm at the same rate. For example, the frequency of the light may be adjusted for the slow-warming surface, such as to increase the warming speed so that the inner and outer eyelids warm at the same rate. If the inner eyelid skin needs more warming, the eye treatment device 200 may turn up the green light and turn down the infrared light. In other embodiment, the light used may be multiple wavelengths to adjust between the plates and keep the warming the same.

Some embodiments of the eye treatment device 200 can include a first set of sensors that may be positioned on the surface of the transparent outer eyelid pad 147 and facing the outer eyelid to monitor the temperature of the outer eyelid surface, and a second set of sensors that may be coupled with the scleral shield 300 on the surface facing the inner eyelid to monitor the temperature of the eyelid surface. Such a placement can allow the thermocouples or thermistors to detect the temperature of the outer and/or inner surfaces of an eyelid. For example, the first set of sensors and the second set of sensors can be coupled to a controller 212, and the sensors can be configured to detect the temperature of the outer eyelid surface and/or inner eyelid surface and relay the temperature information to the controller 212. Monitoring the temperatures of such surfaces may help to ensure that a patient does not experience significant discomfort or injury from use of the eye treatment device 200.

In some embodiments, the first set of sensors and the second set of sensors may be safety sensors. The first set of sensors and the second set of sensors may preferably be non-contact sensors such as pyroelectric sensors (for example, IRA-E700ST0 from Murata) or thermopiles (for example, ST25T0-18 from Dexter Research, Dexter, Mich.) or conventional temperature monitoring devices such as a thermocouple, a thermistor, a fiberoptic thermal sensor, or a digital temperature sensor (such as a Dallas Semiconductor DS-18B20). In some embodiments, the first set of sensors and the second set of sensors may be discrete elements (such as, for example, thermocouples made from very fine wire, or miniature thermistors, etc.) embedded in the outer eyelid pad 147 (such as, for example, within a pocket) and/or the scleral shield 300. In some embodiments, the first set of sensors and the second set of sensors may be formed by depositing thin films of appropriate metals onto surface layers and/or intermediate layers of the outer eyelid pad 147 and/or the scleral shield 300.

In some embodiments, the eye treatment device 200 can include a current sense circuit to monitor LED function. The current sense circuit may be a circuit that is configured to sense current passing through the current sense circuit to the LED. For example, the current sense circuit may be configured to detect fault conditions such as a short circuit or open circuit in the current path, which may be due to connection problems and/or problems with the LED. In such current sense circuits, it is important to not only detect a condition, but also to ensure the safe operation of the detection circuitry itself. If a fault is detected, the system may shut-off the fault circuits and/or shut off the eye treatment device 200. In such instances, error codes may be displayed in the screen, to alert the user or clinician to the fault status.

In some embodiments, after temperature of the eyelids 12, 14 reaches a target temperature range, such as a treatment temperature, it may be desirable for the user or clinician to know how long the eyelid stays within the target temperature range. For example, the target temperature range can be between a minimum temperature required to treat the eye condition and a maximum temperature above which discomfort or thermal damage to the eye or eyelid may occur. In some such embodiments, the target temperature range is between about 40 and about 80 degrees Celsius. In some embodiments, the target temperature range is between 50 degrees Celsius and 80 degrees Celsius. In some embodiments, the target temperature range is between 60 degrees Celsius and 80 degrees Celsius. In some embodiments, the target temperature range is between 70 degrees Celsius and 80 degrees Celsius. In some embodiments, the target temperature range is between 40 degrees Celsius and 70 degrees Celsius. In some embodiments, the target temperature range is between 40 degrees Celsius and 60 degrees Celsius. In some embodiments, the target temperature range is between 40 degrees Celsius and 50 degrees Celsius. In some embodiments, the target temperature range is between 40 degrees Celsius and 45 degrees Celsius.

Figure 20:
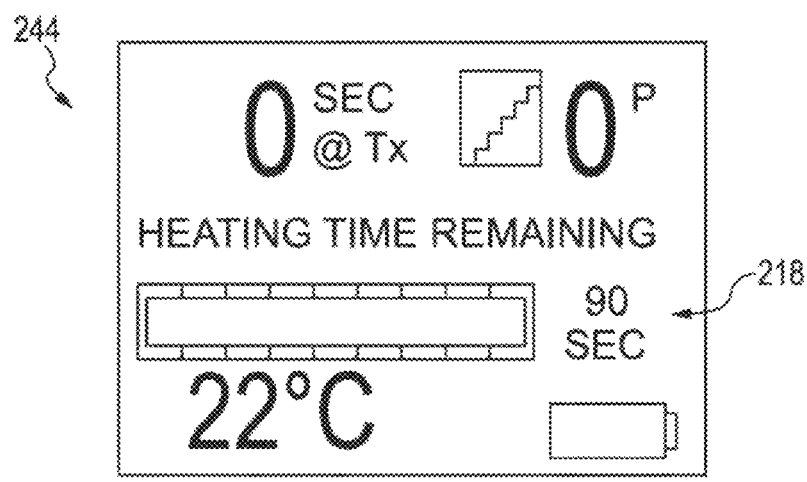
FIG. 20 shows one embodiment of the eye treatment device display showing details of the melt time.

As shown in FIG. 20, the eye treatment device 200 can include a melt time indicator, configured to count the time the eyelids 12, 14 are within the target temperature range. The melt time may be shown on the display 244 of the handheld device 1800. For example, the timer can start a counter once the eyelid temperature reaches a minimum temperature and can continue counting until the eyelid temperature falls below a minimum temperature. In some embodiments, the timer may use the actual measured temperature at a measurement time, while in other embodiments, the timer may use a preset time period.

FIG. 20 shows an embodiment of a dashboard 218 of the display screen 244, configured to display the status of the eye treatment device 200. For example, the dashboard 218 can include a temperature measurement device or means configured to measure various temperatures of the eyelid, such as inner and/or outer surface temperatures, a datalogger 214, a voice recorder 213, a battery configured to power the components of the dashboard, a battery charging means, a controller, printed circuit board, and/or communication circuitry between the scleral shield 300 and the energy transducer 205.

In some embodiments, the eye treatment device 200 may further include a display screen 244 configured to display the inner eyelid and outer eyelid temperatures. For example, the temperature display feature may display absolute temperatures, or may display relative temperatures versus a maximum. For example, the temperatures may be displayed in a bar graph format, or with one or more lights, etc.

In some embodiments, during use of the eye treatment device 200, the temperature of the inner and/or outer eyelid surface can be measured and displayed on the display screen 244 for the clinician. For example, the clinician can apply heating energy to the eyelid, and when the eyelid temperature reaches the treatment temperature, the clinician can apply a compressive force while visually monitoring the eyelid margin, such as to optimize the expression of meibum from clogged meibomian glands.

Figure 21A:
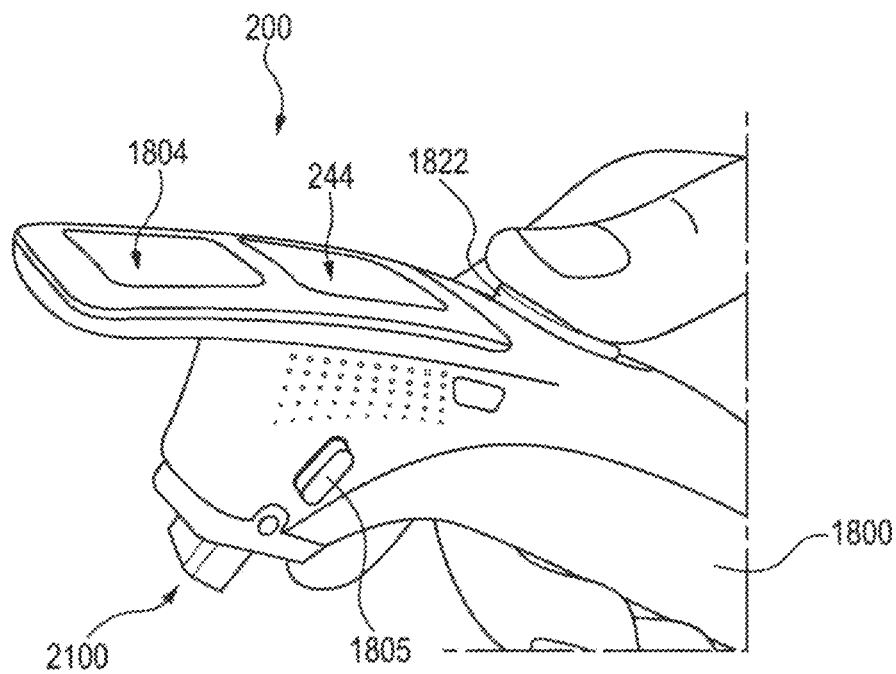
FIGS. 21A and 21B are views showing one embodiment of the eye treatment device having a movable light pipe.
Figure 21B:
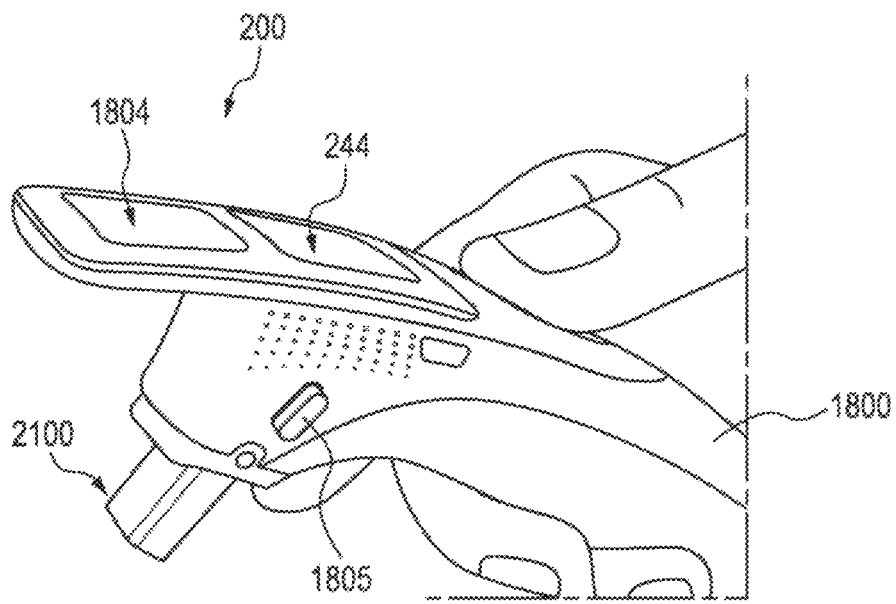

FIGS. 21A and 21B show another embodiment of an eye treatment device 200. FIG. 3A is a schematic side plan view of the embodiment of an eye treatment device 200 of FIGS. 21A-21B, wherein the eye treatment device 200 is operational and is transmitting light 211 to the eyeball 20 and the treatment tissue. In some embodiments, a movable light pipe or shroud 2100 having an internal reflective surface can be used to reflect or guide the light 211 towards the energy transmission surface 140, thereby improving the efficiency of the heating of the target tissue. FIG. 21A shows the shroud 2100 in a retracted position, and FIG. 21B shows the shroud 2100 in an advanced position. For example, the shroud 2100 may be used when the light 211 that is emitted from the energy transducer module 120 includes a portion of the light 211 initially radiated at an angle such that without correction the light 211 would not reach the energy transmission surface 140 for passage to the treatment tissue. The movable light pipe or shroud 2100 can be used to correct this and focus the light 211 toward the treatment tissue.

In some embodiments, the movable reflector, light pipe or shroud 2100 can be a sliding assembly that surrounds the heat source LEDs and guides light 211 towards the eyelid. For example, the user or clinician can control movement of the shroud 2100 by pressing a compression control button 1822 connected to the shroud 2100. In some embodiments, when a sterile disposable component 260 is attached to the handheld instrument 1800, the outer eyelid pad 147 can automatically attach to the front of the shroud 2100. When the clinician presses the compression control button 1822, the shroud 2100 and outer eyelid pad 147 can be advanced toward the eyelid. In some embodiments the outer eyelid pad 147 is positioned at the eyelid surface for heating the eyelid without compression. In other embodiments, the eyelid is compressed between the outer eyelid pad 147 and a stationary backplate. For example, when the clinician depresses the compression control button 1822 with their finger or thumb, the shroud 2100 and outer eyelid pad 147 advance toward the stationary backplate. The amount of heat and pressure applied may thus be under direct control of the clinician, who can monitor the response of the glands and the comfort of the patient.

In some embodiments, the inner wall surface of the shroud 2100 may be smooth and/or polished, such as to avoid or minimize light 211 scattering when experiencing reflection from the walls. For example, the walls can have a mirror-like surface such that reflection of the light 211 is kept within the shroud 2100, even when the light 211 hits the side walls. In embodiments, mirrored surfaces of the walls can be obtained by depositing a reflective layer or layers using any known means, such as, for example, silvering, aluminizing or laminating with a mirrored film, or other types of mirror finishing, to further enhance the ability of the shroud 2100 to conduct light 211.

Figure 22:
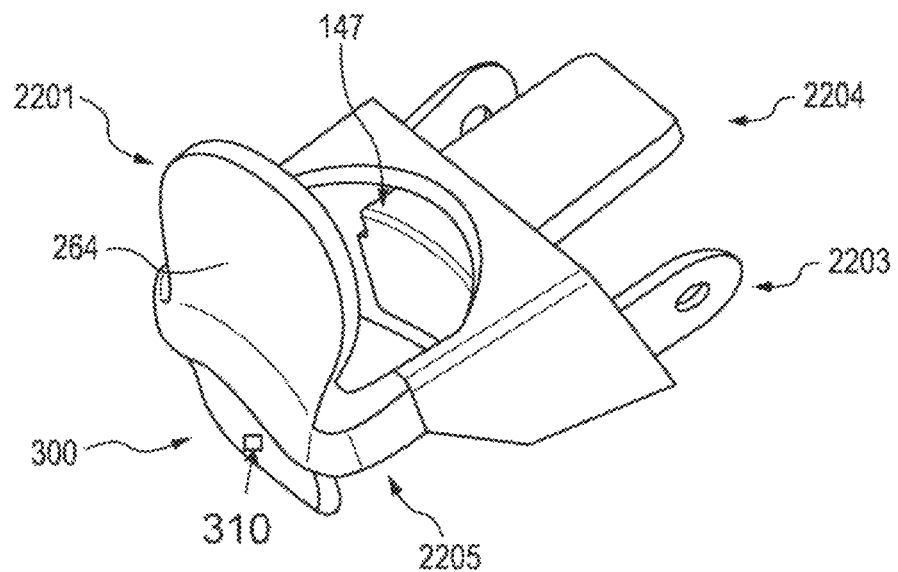
FIG. 22 shows more features of the disposable including the frontplate design elements.
Figure 23:
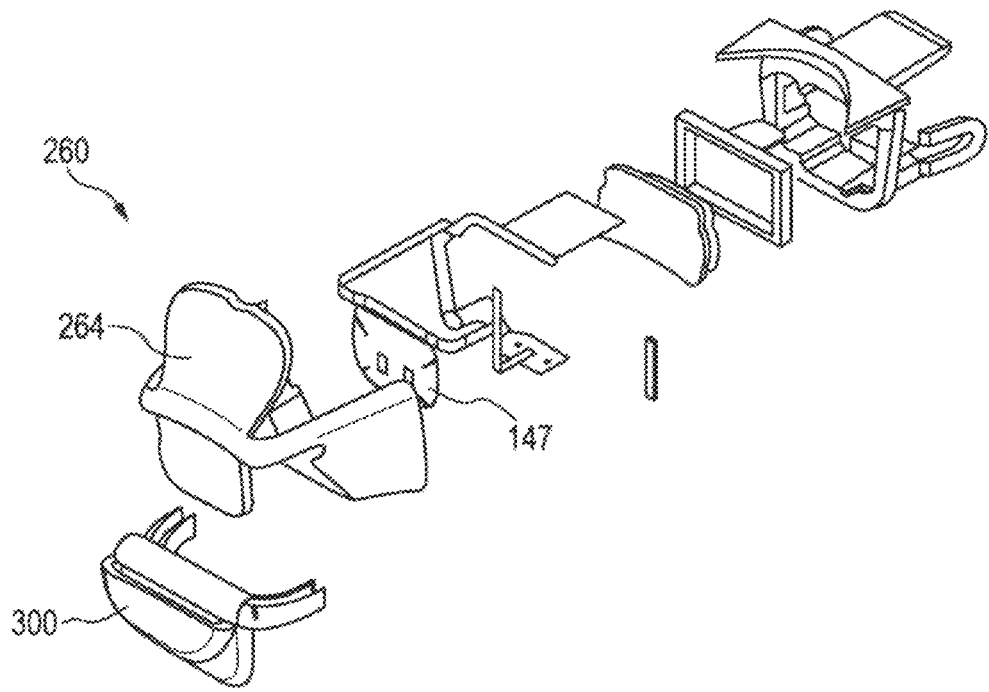
FIG. 23 is an exploded view of the disposable of FIG. 22.

FIGS. 22 and 23 show an embodiment of a front pad of an eye treatment device. For example, an outer eyelid pad 147 can be interposed between the light source of the eye treatment device 200 and the patient's outer eyelid. The outer eyelid pad 147 may be configured to engage the shroud 2100 when the shroud 2100 is extended for treatment. Because the shroud 2100 may become warm during treatment, the outer eyelid pad 147 may include a perimeter frame to engage the walls of the shroud 2100 such as to keep the outer eyelid pad 147 from warming.

In some embodiments, the outer eyelid pad 147 may not be used to shield the eye from heat energy, but may instead be used to measure temperatures. For example, the outer eyelid pad 147 may be made of materials that are substantially transparent to the energy emitted from the energy transducer. By way of specific example, if the energy transducer is a light source, the outer eyelid pad 147 may be made of a clear material that does not impede the wavelength(s) of light emitted by the energy transducer.

FIG. 22 shows embodiments of the sterile disposable component 260. In embodiments, the sterile disposable component 260 includes the following exemplary components: an inner eyelid pad 300, an outer eyelid pad 147, an eye shield 264, a silicone cover 2201, attachment tabs 2203, a guide 2204, and support arms 2205.

The inner eyelid pad 300 can be made of plastic that is configured to be heated by the light-based heat source in the handheld Instrument 1800. In embodiments, the plastic parts can be surrounded by a soft, biocompatible silicone cover 2201. In embodiments, there are two temperature sensors 310 located in the inner eyelid pad 300 that can measure the temperature of the inner surface of the eyelid. The inner eyelid pad 300 is also referred as the backplate.

The outer eyelid pad 147 can be configured as a clear, biocompatible silicone pad that is mounted on a plastic frame. In embodiments, the plastic frame has a minimum thickness of 0.010" at the location of the temperature sensors 310. In some embodiments, the outer eyelid pad 147 is in patient contact during the treatment. When the sterile disposable component 260 is attached to the handheld instrument 1800, the frame can attach to the shroud 2100 of the handheld instrument 1800. Light from the heat source in the handheld Instrument 1800 can shine through the outer eyelid pad 147 to heat the eyelid tissue. In some embodiments, there are two temperature sensors 310 located in the outer eyelid pad 147 that can measure the temperature of the outer surface of the eyelid.

The eye shield 264 can block light emitting from the handheld instrument 1800, and thereby protect portions of the eye that are not intended to be heated. In embodiments, the inner eyelid pad 300 and portions of the eye shield 264 can be covered with a soft, biocompatible silicone component or silicone cover 2201. For example, the silicone cover 2210 can have a minimum thickness of 0.010" at the location of the temperature sensors 310. In some embodiments, the silicone cover 2201 is in patient contact during the treatment.

The sterile disposable component 260 can be secured to the handheld instrument 1800 by the attachment tabs 2203. For example, when the sterile disposable component 260 is attached to the handheld device 1800, spring-loaded latches can mate with openings in each of the attachment tabs 2203, thereby securing the sterile disposable component 260 to the handheld instrument 1800. The guide 2204 can assist in aligning the sterile disposable component 260 to the handheld instrument 1800. The support arms 2205 can connect the inner eyelid pad 300 to the main body of the sterile disposable component 260. These support arms 2205 serve as a guide to the proper depth to insert the Inner Eyelid Pad 300 behind the eyelid.

FIG. 23 is an exploded view of the sterile disposable component 260, showing an embodiment of the temperature sensors 310 on the outer eyelid pad 147. Any of the pads shown in FIG. 23 can be formed of multiple pieces, or can be one monolithic piece. In embodiments, the temperature sensors 310 can be designed to measure the outside eyelid temperature. During use, light 211 can hit the rear of the set of temperature sensors 310. If this happens, the temperature sensors 310 may read the light temperature instead of the eyelid temperature. To prevent this, the rear of the temperature sensors 310 may be covered with a material that will not heat. For example, the rear of the temperature sensors 310 may be covered with a reflective coating to reflect the light 211 away from the temperature sensors 310 without heating the rear of the temperature sensors 310.

FIG. 23 shows an embodiment of a sterile disposable component 260 that is designed for single-use and should not be reused. In some embodiments, in order to keep track of the number of uses, the sterile disposable component 260 may include an on-board memory that contains custom treatment parameters. For example, the custom treatment parameters could include the number of uses available, such as for a single-use sterile disposable component 260, and conveys the information to the eye treatment device 200. Once the eye treatment device 200 is used for treatment, the custom treatment parameters will not all allow it to be used again. In some embodiments, once the sterile disposable component 260 is attached, the use information may also be displayed on the display 244, so the user knows that the sterile disposable component 260 may be used for single-use.

In some embodiments, the sterile disposable component 260 may be designed for multi-use. For example, the on-board memory may keep track of the number of uses, and once the maximum number of uses is reached, the eye treatment device 200 will not allow treatment with the sterile disposable component 260. This information may displayed on the display 244 when the sterile disposable component 260 is attached, showing the number of remaining uses available. Once the eye treatment device 200 is used for treatment to the maximum number of allowed uses, the custom treatment parameters will not all allow it to be used again.

Figure 24:
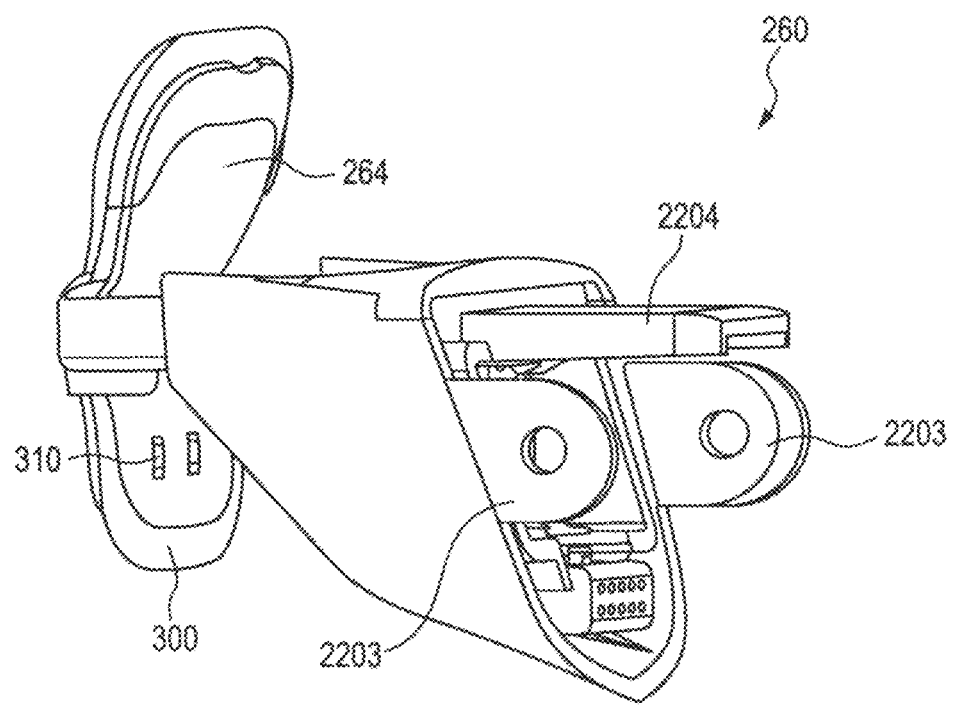
FIG. 24 shows more features of the disposable including the thermal isolation of the backplate sensors.

FIGS. 23 and 24 show an embodiment of a stationary backplate or stationary inner eyelid pad 300. In embodiments, the stationary inner eyelid pad 300 can be configured to be positioned between the eyelids 12, 14 and the eyeball 20, such as to cover the sensitive, anatomy of the eye system 10 and prevent light 211 from contacting the eyeball 20. For example, the stationary inner eyelid pad 300 can include a reflective surface configured to receive the light 211 and reflect the light 211 toward the inner eyelid surface for warming.

In some embodiments, the stationary inner eyelid pad 300 can include a set of temperature sensors 310 positioned toward the inner eyelid. For example. the set of temperature sensors 310 may be discrete elements (such as thermocouples made from very fine wire, miniature thermistors, etc.) embedded or positioned in the stationary inner eyelid pad 300. In some embodiments, the set of temperature sensors 310 may be thermocouples, formed by depositing thin films of appropriate metals onto intermediate layers of the stationary inner eyelid pad 300.

In embodiments, to prevent the stationary inner eyelid pad 300 from warming or heating the set of temperature sensors 310, the energy absorbing surface or reflective surface of the stationary inner eyelid pad 300 can include sensor windows for the set of temperature sensors 310 to extend through and thereby contact the inner eyelid surface directly.

FIGS. 19 and 24 are views showing details of embodiments of the frontplate or outer eyelid pad 147, and backplate or inner eyelid pad 300. In some embodiments, the sets of temperature sensors 310 are redundant sensors that are collocated for redundancy and improved accuracy. Each set of temperature sensors 310 can provide a primary and a secondary measure of the eyelid temperature. The secondary measure of eyelid temperature can be used in conjunction with primary eyelid temperature measurements for improved temperature sensing accuracy and reliability.

In some embodiments, obtaining two or more eyelid temperature readings facilitates redundancy. One aspect of the present disclosure includes the step of comparing the primary eyelid temperature reading and the secondary eyelid temperature reading, such as to determine whether both sensors of the set of temperature sensors 310 are operational.

The set of temperature sensors 310 can be subjected to mechanical and/or thermal stresses, and one of the set of temperature sensors 310 may stop working. Having a redundant set of temperature sensors 310 can allow the system to use the second set of temperature sensors 310 to provide the temperature information required to finish the procedure.

In some embodiments, the sets of inner and outer eyelid temperature sensors 310 may be redundant temperature sensors 310. For example, each set of temperature sensors 310 may measure the inner eyelid surface temperature or outer eyelid surface temperature. Both of the sets of temperature sensors 310 should read the same temperature. If the temperature provided by the sets of temperatures sensors 310 does not match, it might mean that treatment is not correctly positioned on eyelid, or that there is a problem and the system should be shut down.

FIGS. 23 and 24 show an embodiment of a sterile disposable component 260 that includes an identification (ID) chip. The ID chip may protect against counterfeit disposables by ensuring that genuine sterile disposable components 260 are used in treatment. The ID chip may also provide automated treatment tracking, by tracking the usage of sterile disposable components 260 and adherence to disposable guidelines for the maximum number of uses. Additionally, the ID chip may help to maintain inventory visibility by managing supplies and inventories in real-time, for direct purchase and consignment.

In some embodiments, the eye treatment device 200 may use authentication methods and/or protocols to determine whether the sterile disposable component 260 is counterfeit. For example, the eye treatment device 200 may include a communications protocol configured to provide the ability to distinguish between an authorized sterile disposable component 260 and an unauthorized clone. The communications protocol may be further configured to allow the eye treatment device 200 to reject the sterile disposable component 260 if it is determined to be an unauthorized clone. In some embodiments, the eye treatment device 200 may also include a mechanism to limit usage and/or count the number of uses of the sterile disposable component 260, and allow the eye treatment device 200 to reject the sterile disposable component 260 if it exceeds the maximum allowed usage and/or number of uses.

In some embodiments, the sterile disposable component 260 includes an on-board memory that contains custom treatment parameters, specific to the type of sterile disposable component 260 that is being used. For example, when the sterile disposable component 260 is attached to the eye treatment device 200, the eye treatment device 200 can read the treatment parameters and adjust the treatment to match the custom parameters.

In some embodiments, different sterile disposable components 260 are used during treatment of the eye. Therefore, the custom treatment parameters might include light settings for each different sterile disposable component 260. For example, some of the sterile disposable components 260 may have different backplate designs and may therefore require different treatment settings. In some embodiments, the backplate can include an energy absorbing portion that warms, and then transfers the heat to the inner eyelid. In other embodiments, the backplate can have a reflective surface that reflects the light energy back onto the eyelid for heating.

In some embodiments, the sterile disposable component 260 may be used for taking pictures of the eyelid, and the custom parameters can include a light lock-out feature configured to ensure that the light does not shine.

In some embodiments, the sterile disposable component 260 may be used for both treatment and video. For example, the treatment parameter may include the interleaving of the video clips and light-based heating such that the video is not washed out.

FIGS. 19, 22, 23, and 24 are embodiments showing a sterile disposable component 260 that is a sterile, single-use component and that includes all of the parts intended to contact the patient's eyelid. The sterile disposable component 260 is removed from packaging prior to use and attached to the handheld instrument 1800.

The handheld instrument 1800 is a hand-held eye treatment device 200 that allows the ECP to view, heat and compress the portion of the eyelid that is in contact with the sterile disposable component 260. The source of heating is optical radiation produced by lime-green and infrared LEDs in the handheld instrument 1800.

In some embodiments, an internal rechargeable lithium ion battery provides power to operate the handheld instrument 1800. For example, the battery can be recharged by placing the handheld instrument 1800 in a separate charging stand that is powered by an AC Power Supply.

The main parts of the sterile disposable component 260 are shown in FIG. 22. In some embodiments, the sterile disposable component 260 can have the approximate dimensions of 1½" (L)×1" (W)×1" (H). The sterile disposable component 260 may have different dimensions without departing from the scope of this disclosure. In embodiments, the sterile disposable component 260 can be a sterile component, used for a single patient treatment and then disposed of. For example, during a treatment, the inner eyelid pad 300 can be inserted behind the eyelid in the fornix, and may be intended to contact the inner mucosal lining (i.e., the palpebral conjunctiva). The outer eyelid pad 147, which opposes the inner eyelid pad 300, can contact the skin on the outer surface of the eyelid. Light 211 produced by the handheld instrument 1800 can be transmitted through the clear outer eyelid pad 147 to warm the eyelid tissue. The outer eyelid pad 147 can be used to apply pressure to the eyelid by moving towards the inner eyelid pad 300 by means of a mechanism in the handheld instrument 1800. Temperature sensors 310 in the outer eyelid pad 147 and inner eyelid pad 300 can monitor eyelid temperature during a treatment.

The embodiment of the sterile disposable component 260 shown in FIGS. 19, 23, and 24 may further include drug-eluting front and/or rear pads that can contact the eyelid and transfer the drug to the outer and/or inner eyelid surface. The drugs may treat a number of conditions. For example, the drug-eluting pads may include one or more of the following: a numbing agent, such as to block the nerves in the eyelid from feeling pain or discomfort during treatment; an antibiotic, such as for the treatment of blepharitis, to decrease inflammation and more quickly diminish symptoms; and/or a steroid, such as for treatment of inflammatory skin conditions including atopic dermatitis, psoriasis, seborrhea, contact dermatitis, and the like. There are some treatment drugs that may need to additional help to permeate the eyelid skin, such as via iontophoresis.

Iontophoresis is a method of non-invasive transdermal drug delivery to the eyelid skin, based on the transfer of charged molecules using a low-intensity electric current. In some embodiments, the eye treatment device 200 may deliver the drugs via iontophoresis-mediated drug infusion to the eyelid. For example, the disposable pads can include the drug, and the iontophoresis-mediated drug infusion can use a weak electrical current to stimulate drug-carrying ions to pass through the eyelid skin. The electrical current may be provided by the sterile disposable component 260 or the handheld instrument 1800. In some cases, local anesthesia may be required for the eyelid treatment for patients that fear the pain. For these cases, lidocaine can be delivered to the eyelid using iontophoresis-mediated drug infusion.

In some embodiments, the eye treatment device 200 may be configured to treat hordeolum and/or chalazion. Chalazia and hordeola (styes) are sudden-onset, localized swellings of the eyelid. A chalazion is caused by noninfectious meibomian gland occlusion, whereas a hordeolum usually is caused by infection. Both conditions initially cause eyelid hyperemia and edema, swelling, and pain.

To treat hordeolum, the inner eyelid pad 300 and/or outer eyelid pad 147 may include features to focus pressure on the sty or pimple, to squeeze the eyelid and drain the hordeolum. To treat chalazion, the inner eyelid pad 300 and/or outer eyelid pad 147 may have features to focus pressure on the occluded meibomian gland, to open the gland.

In some embodiments, the eye treatment device 200 can include an integrated camera as a visualization means 160. For example, the integrated camera or integrated visualization means 160 can allow the user to determine how treatment is progressing either before, during, or after treatment. In some embodiments, the integrated visualization means 160 may include fixed optics, adaptive optics, and/or active optics to view different areas of the eyelid, including the front surface, rear surface and eyelid margin. For example, adaptive and active optics can be configured for focusing and/or zooming onto the image or target area. When viewing the eyelid margins, the integrated visualization means 160 can view the expression of the glands. When viewing the rear of the eyelid with light shining on the front of the eyelid, the integrated visualization means 160 may view the internal gland structure of the eyelid.

In some embodiments, the integrated visualization means 160 may provide video and/or still images of the eyelid. The integrated visualization means 160 may further be coupled to electronics, such as to record and/or transmit images to an external device. In some embodiments, the integrated visualization means 160 can include the electronics. In some embodiments, the integrated visualization means 160 can be coupled to the device controller, with the controller being capable of storing and/or transmitting the still images and/or videos.

The mammalian eyelid is curved, and this curvature is not a serious detriment to direct visual observation by viewing, due to the natural ability of the eye to accommodate (refocus) the curvature. However, when using a photographic camera, the field curvature induces defocus error, which can be significant. One way to correct for field curvature is by placing a single thin lens just in front of the final focus. With the proper choice of parameters, the thin lens flattens the field while inducing very low aberrations. In some embodiments, a field flattener may be used to flatten the curved image. For example, the field flattener can provide more focus throughout the field.

In some embodiments, the eye treatment device 200 may have the capability for an on-board video display. In some embodiments, the video may be recorded to memory within the device, or the video may be recorded to a portable drive, such as a microSD. Once the procedure is complete, the portable drive may be removed and replaced with a blank one for the next procedure.

Figure 25:
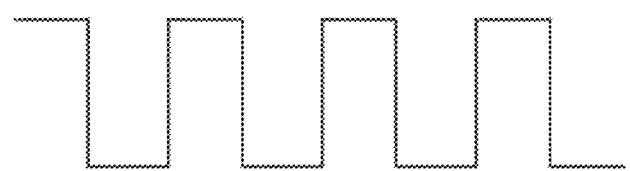
FIG. 25 shows a graph of pulsing or interleaving the light source and camera.
Figure 25:
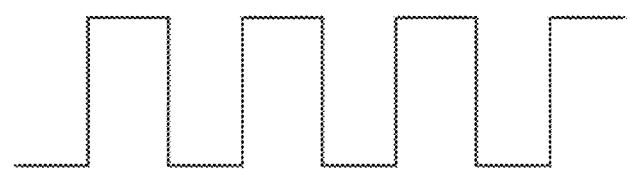

When the integrated visualization means 160 takes a video during treatment, the light 211 used for heating may wash out the video or pictures taken. One solution is to interleave the video and the light-based heating. FIG. 25 shows the pulsing of the light source and the integrated visualization means 160, for example when the light is off the camera is on and when the light comes on the camera turns off. This can allow the video to be taken without disruption from the light 211.

In some embodiments, the eye treatment device 200 may include a special photo disposable, such as for taking photos of the eyelid before and after treatment. For example, the photo disposable can be similar to the sterile disposable component 260 but may use a spacer in place of a stationary backplate 300, to position the eyelid at the proper position. The special photo disposable does not include a backplate 300 because the light 211 is not turned on and is not shining toward the eye. During use, the photo disposable may initially be used for photos prior to treatment. The photo disposable can then be replaced by the sterile disposable component 260. When treatment is complete, the sterile disposable component 260 can be removed and replaced by the photo disposable.

In some embodiments, the photo disposable may include a memory having parameters to customize the camera settings. For example, the photo disposable may be configured to control the type of light used, depending on the photo settings. For example, one of the settings may direct the eye treatment device 200 to shine white light on the eyelid for visualization, while another setting may include the use of infrared light for photo.

In some embodiments, the photo disposable may include a diffractive surface to after the light path. Refraction occurs as light changes angle traveling through the surface. The diffractive surface may narrow the light beam, widen the light beam, or scatter the light beam. In some embodiments, it may be desirable to diffract the light into a narrow beam to focus on a desired treatment area on the eyelid. In some embodiments, it may be desirable to widen the light beam to widen the treatment area on the eyelid. In some cases, it may be desirable to diffract the light for more uniform coverage of the treatment area.

In some embodiments, the eye treatment device 200 may be configured to stream video using the integrated visualization means 160. For example, the integrated visualization means 160 and/or the eye treatment device 200 may include a wireless link to send the video to an external device, such as an external monitor for viewing, or to stream the video to another external device, such as a computer. In some embodiments, metadata may be added to the video live stream, to relay more treatment information on the monitor. For example, the metadata may include sensor readings, such as information relating to inner and/or outer eyelid temperatures, pressure and/or force applied to the eyelid, light intensity, light frequencies, etc. Other data may also be included, such as the date and time, the patient's name or medical record number, clinician's name, or other information related to the treatment.

Meibography is a technique that yields information on the morphological characteristics of meibomian glands by observing their silhouette via transillumination of the eyelids 12, 14. One type of meibography is a non-contact infrared meibography technique that allows for non-contact observation of the structure of the meibomian gland with no discomfort to the patient. Meibography incorporates an infrared LED light to capture an image of the meibomian glands of the upper and lower eyelids. It provides a detailed picture of meibomian gland structure, including those glands that have increased tortuosity or have stopped functioning, resulting in meibomian gland dropout. A non-contact meibography system may include an integrated visualization means 160, an external monitor, and/or a recording device. Images may be obtained using an infrared light source. Such a meibography system can allow for easy observation of the meibomian gland structures in both the upper and lower eyelids without causing patient discomfort.

Transillumination can be used to image the meibomian glands in one of several ways. In one variation, illuminating light can be directed at the outer surface of the eyelid at an angle, with imaging also taking place from the outer surface of the eyelid. This is referred to as oblique illumination. In a second variation, light can be directed from behind the eyelid through the eyelid with imaging taking place through the outer surface of the eyelid. In a third variation, the surface is illuminated from the front in a manner such that the light source partially blocks the image being recorded, with averaging, adding or otherwise combining of multiple images being used to produce a complete image. In each instance, the meibomian gland is illuminated in order to visually examine the gland using light transmitted through the eyelid tissue. The eyelid can then be imaged using still or moving photography (visible light, NIR or IR, or other suitable light wavelength) in a manner similar to that described above.

One method of viewing the glands is via transillumination of the lid and observation with the integrated visualization means 160. For example, the light can be positioned on one side of the eyelid and the silhouette of the meibomian glands can then be observed on the other side of the eyelid, using the integrated visualization means 160. This method can provide information about the morphology and physical characteristics of the meibomian glands. Some of the information that can be measured may include the number of glands and the degree of gland dropout, or area of meibomian gland loss, etc.

In some embodiments, the eye treatment device 200 may be used to assess the severity of dry eye by observing the tear film break-up time. Tear film break-up time is a method for determining the stability of the tear film and checking for evaporative dry eye. Tear film break-up time can be helpful in assessing the stability of the tear film and therefore the severity of meibomian gland dysfunction. In testing for tear film break-up time, fluorescein dye is added to the eye and the eyelid is held open. The tear film is observed using a magnifier while the patient avoids blinking until tiny dry spots develop, i.e. tear film break-up. The tear film break-up time is then measured. In some embodiments, the eye treatment device 200 may have a timing feature, configured to record a tear film break-up time measurement. A short tear film break-up time is a sign of a poor tear film, and a longer tear film break-up time indicates a more stable tear film. For example, >10 seconds is thought to be a normal tear film break-up time, 5 to 10 seconds is considered marginal, and <5 seconds is considered low.

In some embodiments, the eye treatment device 200 may be used for skin pigmentation measurement, and may be adjusted to tailor treatment parameters based on the pigmentation. For example, the integrated visualization means 160 may view and/or record the skin as the light is reflected from the skin. Differences in reflection occurs between different skin types. Using this knowledge, the eye treatment device 200 may tailor treatment parameters based on the skin pigmentation indicated by the light reflection measurement. In general, darker skins colors absorb more infrared light than lighter skin colors, therefore the skin becomes hotter faster as more light is transformed into heat. The eye treatment device 200 may thus be configured to tailor treatment parameters by adjusting the light frequency based on the pigmentation measurement.

The pigmentation of skin is related to the amount of melanin in the keratinocytes of the epidermis. The various contents of melanin produce the wide spectrum of human skin color observed. When light hits the skin, part of the light is reflected by melanin, and this reflection may be used to detect the pigmentation level of the skin.

In some embodiments, the eye treatment device 200 can shine the light 211 on the skin and the integrated visualization means 160 can view and/or record the skin as the light 211 is reflected from the skin. Because reflection differences occur between different skin types or skin pigmentations, the integrated visualization means 160 can be used to detect pigmentation.

Spectroscopy is the study of how substances absorb, transmit, or reflect light. Spectroscopy may be used to detect skin pigmentation. Because different skin pigmentations have unique reflectance characteristics, we can determine the skin pigmentation by analyzing the light reflectance characteristics.

In some embodiments, the eye treatment device 200 is configured to detect whether the eyelid is properly captured in the correct position for treatment. In some embodiments, the detection of proper eyelid capture may be achieved by visual means, such as using the magnifier 1804 or integrated visualization means 160. In some embodiments, the detection of proper eyelid capture may be done using one or more contact sensors 238. The integrated visualization means 160 may be used for direct visualization of the eyelid and may be used to determine whether the eyelid is properly positioned for the desired treatment or procedure. In addition, the eye treatment device 200 may include an image recognition feature that may use the image from the integrated visualization means 160 to determine whether the eyelid is in the proper position. The contact sensors 238 may be configured to shut off the eye treatment device 200, and/or the eye treatment device 200 may signal the user or ECP to stop treatment using lights, beeps or other notification means. For example, the contact sensors 238 may be configured to provide information to a user or ECP using signals from one or more outputs. The outputs may be configured to display light in one or more colors, or sound in one or more tones. The outputs can be configured to display different light patterns or sound patterns, configured to vary the intensity of a light or a sound, configured to provide light and sound combinations, or otherwise configured to indicate different statuses or modes of eyelid capture. In embodiments, the contact sensors 238 may be configured to communicate eyelid capture information to other medical devices and/or communication devices.

Figure 26A:
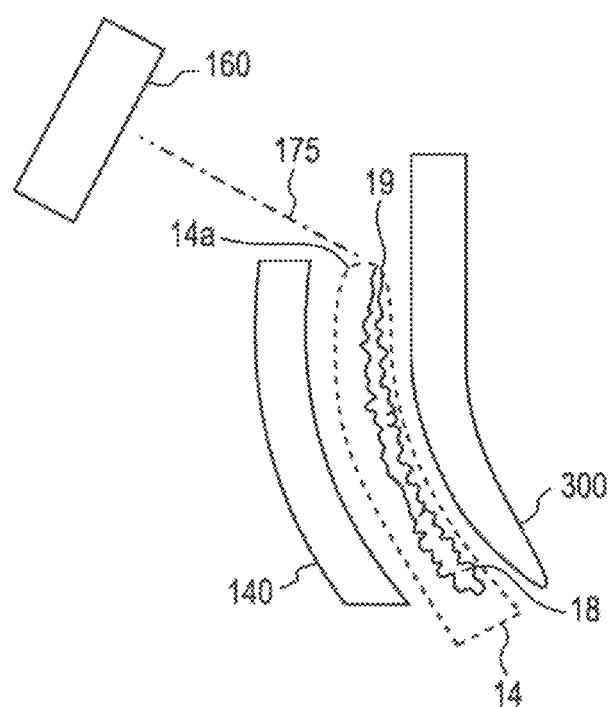
FIGS. 26A and 26B show embodiments of a camera used to view and/or to photograph the surface of the eyelid and the margin to detect blocked meibomian glands.

FIG. 26A shows an embodiment of an integrated visualization means 160 used to photograph the surface of the eyelid and the eyelid margin, to detect blocked meibomian glands. There are several factors to be considered when assessing the meibomian glands. These factors include the percentage of partial glands, the presence of chalazia, and the number of glands present within the eyelid margin.

Photographs may be used for meibomian scoring (MG scoring) which may correspond proportionally to the area of destruction. Scoring may range from 0 to 3, with 0 indicating that the eyelid margin has no partial or missing glands, 1 indicating that less than 33% of the eyelid margin area is involved, 2 indicating that the area of the eyelid margin involved encompasses between 33% and 66, or 3 indicating that the involved area encompasses more than 66% of the eyelid margin. The numerical values obtained for the upper and lower eyelids are summed together to obtain a score ranging from 0 to 6.

In some embodiments, the integrated visualization means 160 may also be used during treatment to record the meibum expression from the glands as they are heated and squeezed by the eye treatment device 200. The expressed meibum may be graded as follows: 0 indicates clear meibum expressed easily; 1 indicates cloudy meibum expressed gently; 2 indicates cloudy meibum that can be expressed with more than moderate pressure; and 3 indicates that no meibum can be expressed even with hard pressure. The expressed meibum material may be used to diagnose other conditions, such as blepharitis, abnormal lid margin, lid margin irregularity, lid margin thickening, partial glands, and/or gland dropout, etc.

In some embodiments, the integrated visualization means 160 may also use IR light to locate the Meibomian glands and determine whether the glands are filled with material which may have a different NIR response than the tissue around it. For example, using a sophisticated High Resolution NIR camera should be sufficient to differentiate between areas of tissue and areas of glands. The wavelength and optics used for the NIR camera should be selected to provide suitable imaging of the meibomian glands, and can be optimized by experimentation. Additionally, it may be advantageous to digitally process the resulting images to enhance the contrast level and/or assign coloration to distinguish between the NIR responses of the various tissues.

Image enhancement techniques have been widely used in many applications of image processing where the subjective quality of images is important for human interpretation. Contrast is an important factor in any subjective evaluation of image quality. Contrast is created by the difference in luminance reflected from two adjacent surfaces. In other words, contrast is the difference in visual properties that makes an object distinguishable from other objects and the background. In visual perception, contrast is determined by the difference in the color and brightness of the object with other objects. Many algorithms for accomplishing contrast enhancement have been developed and applied to problems in image processing. One is a stretch algorithm that may be used to increase the image contrast, and may also improve the lightness.

When the eyelid is inverted for viewing, it has a curved surface. When taking a picture of the curved surface, some of the areas are in focus, while other portions are out of focus. One option is to physically flatten the curved eyelid surface. Another option is to use different photographing techniques for curve surfaces. To physically flatten the eyelid, a clear flat element, such a glass, may be used. Once the eyelid is inverted, the clear flat element can be pressed against the eyelid surface to flatten it for the camera. One method of taking pictures of everted eyelid curved surfaces is focus stacking. Focus stacking is a digital image processing technique which combines multiple images taken at different focus distances, to give a resulting image with a greater depth of field (DOF) than any of the individual source images. The starting point for focus stacking is a series of images captured at different focal depths. In each image, different areas of the everted eyelid will be in focus. While none of these images has the sample entirely in focus, they collectively contain all of the data required to generate an image which has all parts of the eyelid in focus. In-focus regions of each image may be detected automatically, for example via edge detection or Fourier analysis, or may be selected manually. The in-focus patches are then blended together to generate the final image of the eyelid.

A common technique of image interpretation as a part of the medical diagnostic process is visual interpretation. Visual interpretation makes the process depend on the observer. Human visual perception of images depends on a small set of image characteristics: brightness, contrast, sharpness, saturation, and dynamics. To improve the readability of images and to reduce the factors influencing information extraction and perception, the images are enhanced. Image enhancement refers to a technique that improves or modifies digital images, such that the resulting image is better suited than the original for a particular application. During the image enhancement process, one or more attributes of the image are modified. The set of modified attributes, the modification method, and the range of possible attribute values are specific to a given task. One technique for image enhancement is High Dynamic Range (HDR) imaging. HDR imaging methods compensate for detail loss by taking multiple pictures at different exposure levels and stitching them together, to create an image which presents the greatest number of details in both dark and bright areas. Another technique for image enhancement is pseudo-color. The purpose of pseudo-coloring is to harness the perceptual capabilities of the human visual system in order to extract more information from an image, for example an image of an eyelid. The term "pseudo-color" or "false color" is used to differentiate the process of assigning colors to monochrome images from the process associated with true color images. The pseudo-color process can significantly improve the detectability of weak features, structures, and patterns in an image by providing image details that otherwise would not be noticed.

Figure 26B:
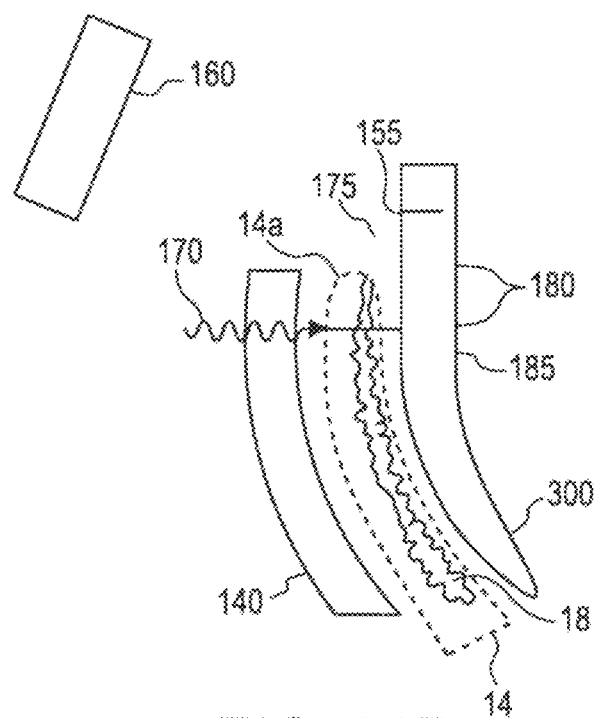

FIG. 26B shows one embodiment of a stationary inner eyelid pad 300 that allows viewing of the inner side of the eyelid 14 and transillumination of the meibomian glands from behind the eyelid 14. In some embodiments, the reflective surface of the stationary inner eyelid pad 300 may also be configured to view the inner surface of the eyelid 14 with the visualization means 160. In some embodiments, viewing the inner surface of the eyelid 14 includes transillumination of the eyelid 14 and meibomian glands. The image translator 155 allows viewing of the inner side of the eyelid 14 and transillumination of the meibomian glands from behind the eyelid 14.

Illumination energy 170, which may be visible or infrared light, for example, is passed through the eyelid 14 and therefore through meibomian glands 18 as it reflects off of reflective surface of the stationary inner eyelid pad 300, eventually exiting above the eyelid margin 14a. In this manner, the reflective surface allows viewing of a transilluminated image 190 of the inner side of the eyelid 14 under direct visualization or with the aid of a magnifying element or camera, shown collectively as a visualization device or visualization means 160, without having to evert the eyelid 14. FIG. 2F is a front view of the embodiment shown in FIG. 26B, showing transilluminated images 190 of the meibomian glands.

Some medical devices may carry bacteria which can lead to infections or cross-contamination. Antibacterial coatings on the eye treatment devices 200, such as antibiotics or silver particles, can lower the risk of infections. In some embodiments the eye treatment device 200 and/or sterile disposable component 260 includes one or more antibacterial coatings to prevent cross-contamination or the spread of bacteria.

In some embodiments, the sterile disposable component 260 is used to treat both eyes of a patent. Between eyes, the sterile disposable component 260 should be treated with a disinfectant to prevent cross-contamination between the eyes. Wiping the sterile disposable component 260 between eyes also cleans any fluids or eyelid expression from the sterile disposable component 260.

In some embodiments, the device includes a capacitance sensor or contact sensor 238, or other proximity sensor, to sense the position of the eye treatment device 200 relative to the eyeball 20 or eyelid 14 of a patient. In some embodiments, the contact sensor 238 may include one or more electrodes configured to sense a capacitance and/or a change in capacitance as the contact sensor 238 touches the eyeball 20 or eyelid 14. In some embodiments, the contact sensor 238 may include microswitches or force or pressure contact sensors 238, all of which produce a change in signal characteristics when it touches the eyeball 20 or skin of the eyelid 14. Thus, contact sensors 238 can be used to help determine the placement of the eye treatment device 200.

For treatment of the inner eyelid, the inner eyelid pad 300 should be in contact with the inner eyelid surface. To detect this, some embodiments of the eye treatment device 200 include a capacitance sensor or contact sensor 238 to detect if the inner eyelid pad 300 is touching the inner eyelid or the eyeball. If the contact sensor 238 detects the eyeball or is too close to the eyeball, the eye treatment device 200 may signal the user to pull further outward toward the eyelid. If the contact sensor 238 detects touching the eyelid, the eye treatment device 200 is in the correct position for treatment.

In some such embodiments, the controller is programmed to prevent activation of the eye treatment device 200 until the controller detects, through signals from the contact sensors 238 that the eye treatment device 200 is properly placed adjacent to an inner eyelid. Additionally, in some embodiments, the controller is programmed to shut off the energy if signals received from the contact sensors 238 indicate that the eye treatment device 200 is no longer placed properly against the eyelid.

For insertion of the stationary inner eyelid pad 300 behind the eyelid, many people pull the eyelashes to lift the eyelid away from the eyeball for insertion of the inner eyelid pad 300. Many times, this method pulls out the eyelashes and causes pain.

In some embodiments, a suction device can be attached to the outer surface of the eyelid and can pull the eyelid up to make room for the inner eyelid pad 300. Once the inner eyelid pad 300 is in place, the suction device can be detached and removed. For example, lifting the eyelid with the suction device can include: placing a suction portion of the suction device on the outer eyelid, creating a suction to engage the outer eyelid skin, pulling the eyelid away from the eyeball, and once the inner eyelid pad 300 is inserted behind the eyelid, releasing the suction and removing the suction device.

In some embodiments, a pulling device having a curved or hook tip can be slid behind the eyelid and can pull the eyelid way from the eyeball to make room for the inner eyelid pad 300. Once the inner eyelid pad 300 is in place, the pulling device can be removed.

In some embodiments, the sterile disposable component 260 or the inner eyelid pad 300 may have lifting feature, such as a curved tip, hook, or other similar feature to lift the eyelid away from the eyeball. The lifting feature could be incorporated in the design of the inner eyelid pad 300, or may be an add-on part. Lifting the eyelid with the lifting device can include: sliding a lifting feature on a distal end of the lifting device behind the eyelid, lifting the eyelid away from the eyeball, and once the inner eyelid pad 300 is inserted behind the eyelid, removing the lifting device.

In some embodiments, the sterile disposable component 260 or the inner eyelid pad 300 may include a light source for viewing the eyelid, for example, for transillumination or meibography. For transillumination, for example, a light feature on the sterile disposable component can shine light on one side of the eyelid, such as the inner eyelid, such that the user is able to view the glands within the eyelid. In some embodiments, infrared light is projected onto or through the everted lid, and an IR-sensitive camera is used to view the meibomian glands. For meibography, the sterile disposable component 260 can include an infrared LED light source that shines on the eyelid such that the image is captured on a camera. The meibography provides a view of all of the meibomian glands in the eyelid. In some embodiments, the light source emits blue or violet light in the range of 400-450 nm to reduce and/or eliminate bacteria.

Figure 27:
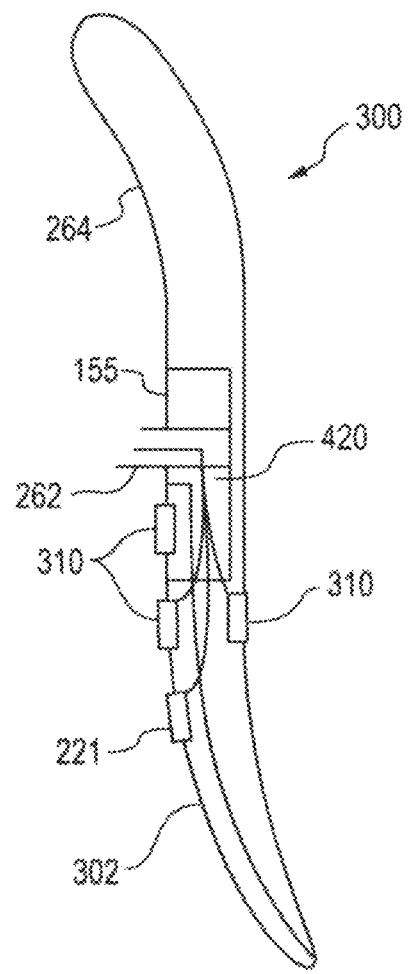
FIG. 27 shows another embodiment of backplate having a heating portion to warm the eyelid.

FIG. 27 shows one embodiment of a reflective inner eyelid pad 300 that can be positioned between the eyelid 14 and eyeball 20 to cover sensitive anatomy of the eye system 10 to prevent light from contacting the eye. The inner eyelid pad 300 is designed to receive the light energy that is transmitted through the eyelid 14 and reflect it back to the eyelid inner surface for warming.

The reflective inner eyelid pad 300 may include a set of temperature sensors 310 positioned toward the inner eyelid. The sensors may be discrete elements (such as thermocouples made from very fine wire, or miniature thermistors) embedded or positioned in the inner eyelid pad 300, or they may be thermocouples formed by depositing thin films of appropriate metals onto intermediate layers of the inner eyelid pad 300.

To prevent the reflective inner eyelid pad 300 from warming or heating the sensors, the energy reflective surface includes sensor windows for the sensors to extend through and contact the inner eyelid surface directly.

In some embodiments the reflective inner eyelid pad 300 may act as a mirror to allow viewing of the inner side of the eyelid 14 with the visualization means. and transillumination of the meibomian glands from behind the eyelid. In some embodiments, the reflected light from the reflective surface of the inner eyelid pad 300 may be used for transillumination of the eyelid and meibomian glands.

FIG. 27 also shows a portion of a sterile disposable component 260 having an inner eyelid pad 300 that may include an energy absorbing front face 302 to warm the inner eyelid. The energy absorbing front face 302 may include a light source for heating. In some embodiments, the light source can be on the inner eyelid pad 300 and directed to the inner eyelid to warm the glands. For example, the light source can emit wavelengths in the range of about 500 nm to about 600 nm, such as to achieve the highest absorption of light rays in tissue.

In some embodiments, the energy absorbing front face 302 can include a light pipe and/or other refractive elements, configured to direct the heating light toward the inner eyelid pad 300 and shine the light on the inner eyelid to heat the meibomian glands behind the eyelid.

In some cases, the meibomian glands may be inflamed or dysfunctional, so it may be desirable to obtain a sample of the meibum to analyze. For example, the meibomian glands may become inflamed due to production of meibum with an increased composition of omega-6 essential fatty acids. Additionally and/or alternatively, bacteria may be in the meibomian glands and may cause inflammation. For these cases, the eye treatment device 200 or sterile disposable component 260 can include a sample receiving portion, configured to obtain a meibum sample as it is being expressed. For example. the sample receiving part may be a meibum reservoir in the sterile disposable component 260 that receives the meibum. In some embodiments, there may be multiple sample receiving parts, such as one for each eyelid. Once obtained, the meibum sample can be tested. In embodiments, the testing may include contacting the meibum with a color sensitive marker that uses color to indicate the presence of bacteria. If there is bacteria present, the ECP may prescribe a treatment plan. Additionally and/or alternatively, a camera may be helpful in obtaining the meibum sample. For example, the camera can view the meibum as it is expressed, either taking pictures or video, to document the capture of the meibum sample.

Eyes and eyelids come in a variety of sizes, from child to adult. To accommodate this, the disposable inner eyelid pad 300 may be made in different sizes. For example, there may be a child size, a small adult size, a medium adult size, and large adult size.

Figure 28A:
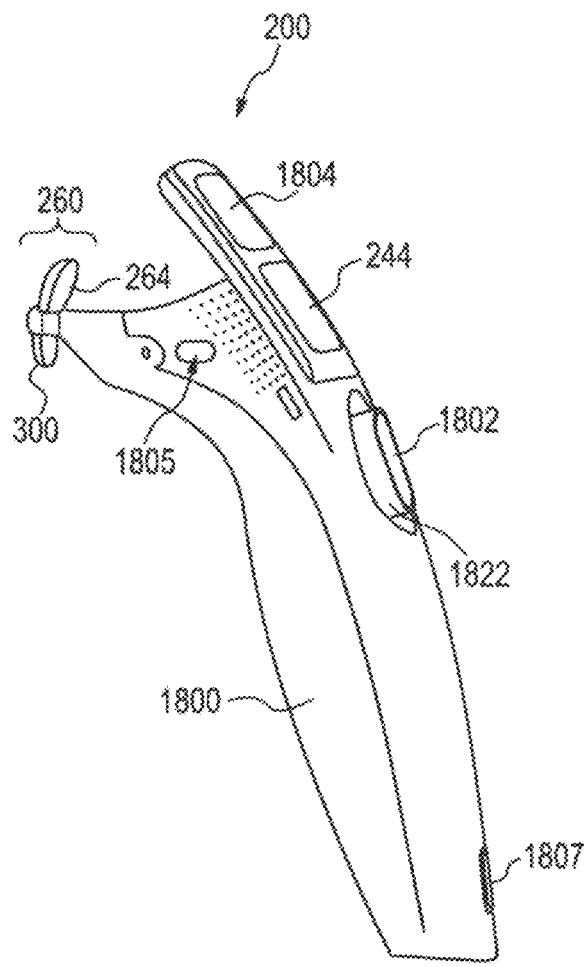
FIGS. 28A and 28B are front and side views of another embodiment of an eye treatment device in which the disposable may be rotated between treatment of the top and bottom eyelids
Figure 28B:
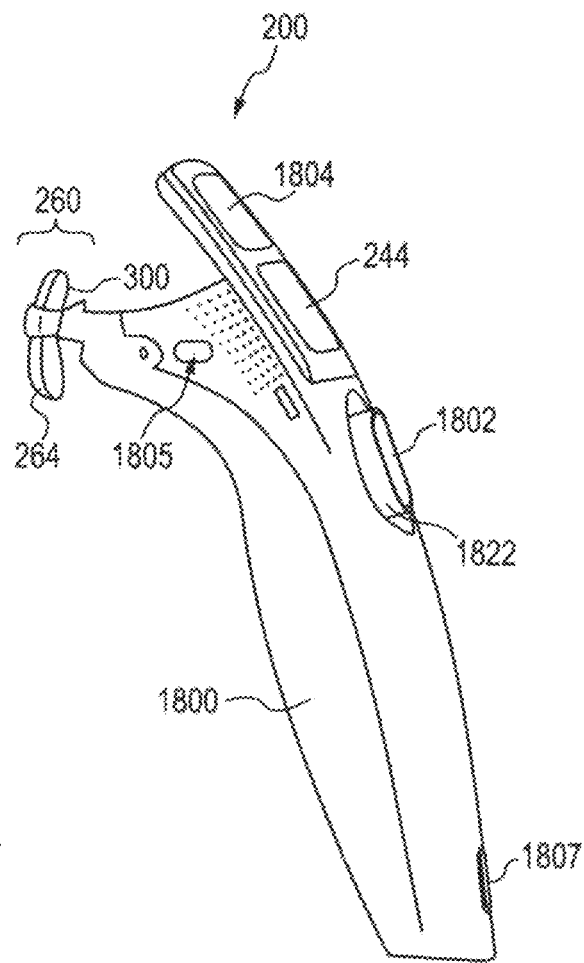

FIGS. 28A and 28B illustrate another embodiment of an eye treatment device 200. In some embodiments, both the eye treatment device 200 and sterile disposable component 260 can be rotated 180 degrees between treatment of the lower eyelid and upper eyelid. Along with this, all of the controls on the eye treatment device 200 would also be rotated, such that, when treating the upper eyelid, the controls are upside down. This may be an issue for some users. As shown in FIGS. 28A and 28B, one option to avoid this potential issue is to rotate the sterile disposable component 260 by 180 degrees while the handheld instrument 1800 remains stationary, such that the eye treatment device 200 is in one position while the sterile disposable component 260 can be in two positions.

In some embodiments, it may be desirable to warm or heat the meibomian glands without squeezing the eyelid. For example, the eye treatment device 200 can be designed as a non-contact infrared heating device, using IR LEDs, and can be configured to heat the meibomian glands within the eyelid without squeezing the eyelid For purposes of summarizing the disclosure, certain aspects, advantages and features have been described herein. It is to be understood that not necessarily all such advantages may be achieved in accordance with any particular embodiment. Thus, the disclosed devices and methods may be embodied or carried out in a manner that achieves or optimizes one advantage or group of advantages as taught herein without necessarily achieving other advantages as may be taught or suggested herein.

While this disclosure has been described in connection with what are presently considered to be practical embodiments, it will be appreciated by those skilled in the art that various modifications and changes may be made without departing from the scope of the present disclosure. It will also be appreciated by those of skill in the art that parts mixed with one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

While the present disclosure has described certain exemplary embodiments, it is to be understood that the disclosure is not limited to the disclosed embodiments, but, on the contrary, is intended to cover various modifications and equivalent arrangements included within the scope of the appended claims, and equivalents thereof.

What is claimed is:

1. A system for treating a mammalian eye having an eyelid, comprising:
 a handheld device having:
  an instrument body with an attachment latch and an electrical coupling pin;
  a control switch that controls an energy transducer having a device that emits light energy at multiple wavelengths, including a first wavelength selected to pass through the eyelid and a second wavelength selected to be absorbed by the eyelid for warming; and
  an actuator controlled by a compression control button to move a movable shroud to extend away from the instrument body, the movable shroud configured to contain and deliver the light energy through the movable shroud;
 an attachable component having:
  an attachment tab configured to couple with the attachment latch of the instrument body;
  an outer eyelid pad frontplate positionable in front of or on proximate an outer surface of the eyelid, the frontplate outer eyelid pad made of a clear material that passes the light energy delivered by the movable shroud wavelengths of light emitted by the energy transducer, the frontplate further comprising sensors configured to provide information regarding a position of the eyelid relative to the frontplate; and
 a backplate positionable behind or on proximate an inner surface of the eyelid, the backplate being made of or coated with an energy-reflecting material configured to receive the first wavelength of light energy transmitted through the eyelid and reflect it back to the eyelid;

the backplate further comprising sensors configured to provide information regarding a position of the eyelid relative to the frontplate;

wherein, when the eyelid is positioned between the outer eyelid pad and the backplate, the light energy from the energy transducer heats a target tissue region of the eyelid sufficiently to melt meibum within a region of meibomian glands located within or adjacent to the target tissue region, and wherein, when the movable shroud extends away from the instrument body, the movable shroud causes the outer eyelid pad to advance toward the backplate and squeeze the eyelid to express the meibomian glands.

2. The system of claim 1, wherein the energy transducer is further configured to provide light energy at a third wavelength selected to treat bacteria.

3. The system of claim 1, further comprising a visualization device for viewing the eyelid during treatment.

4. The system of claim 1, wherein the energy transducer comprises at least one of an LED, laser, incandescent lamp, xenon lamp, halogen lamp, luminescent lamp, high intensity discharge lamp, and gas discharge lamp.

5. The system of claim 1, further comprising one or more components selected from the group consisting of:

a display or dashboard configured to display the device status;

a temperature measurement device configured to measure various temperatures of the eyelid, including inner and/or outer eyelid surface temperatures;

a datalogger;

a voice recorder;

a battery configured to power the device components;

battery charging means;

a controller;

a printed circuit board; and communication circuitry between the backplate and the energy transducer.

6. The system of claim 1, further comprising:

a temperature sensor configured to provide information regarding a temperature of the eyelid, wherein the energy transducer is communicatively coupled with the temperature sensor and configured to detect when the temperature of the eyelid reaches a first predetermined threshold temperature, reduce the intensity of the light emitted by the energy transducer from a first intensity to a second intensity when the temperature of the eyelid reaches the first predetermined threshold temperature, detect when the temperature of the eye reaches a second predetermined threshold temperature selected based on patient safety and continued therapeutic efficiency, and allow the intensity of light to increase to the first intensity when the second predetermined threshold temperature is detected.

* * * * *